US011752290B2

(12) United States Patent
Karlsson et al.

(10) Patent No.: US 11,752,290 B2
(45) Date of Patent: *Sep. 12, 2023

(54) ENDOTRACHEAL TUBE-INSERTING DEVICE

(71) Applicant: Turmidas AB, Stockholm (SE)

(72) Inventors: Annette Arnsäter Karlsson, Tenhult (SE); Måns Collner, Gränna (SE); Hannes Daniel Ulvegard, Jönköping (SE); Ronny Brakhya, Huskvarna (SE)

(73) Assignee: Turmidas AB, Stockholm (SE)

( * ) Notice: Subject to any disclaimer, the term of this patent is extended or adjusted under 35 U.S.C. 154(b) by 881 days.

This patent is subject to a terminal disclaimer.

(21) Appl. No.: 16/469,109

(22) PCT Filed: Dec. 13, 2017

(86) PCT No.: PCT/EP2017/082658
§ 371 (c)(1),
(2) Date: Jun. 12, 2019

(87) PCT Pub. No.: WO2018/109022
PCT Pub. Date: Jun. 21, 2018

(65) Prior Publication Data
US 2019/0307979 A1    Oct. 10, 2019

(30) Foreign Application Priority Data
Dec. 14, 2016  (EP) .................................... 16204104

(51) Int. Cl.
*A61M 16/04*  (2006.01)
*A61B 1/005*  (2006.01)
(Continued)

(52) U.S. Cl.
CPC ....... *A61M 16/0488* (2013.01); *A61B 1/0052* (2013.01); *A61B 1/00066* (2013.01);
(Continued)

(58) Field of Classification Search
CPC .......... A61M 16/0488; A61M 25/0102; A61B 1/00066; A61B 1/0052; A61B 1/267
See application file for complete search history.

(56) References Cited

U.S. PATENT DOCUMENTS 4,921,484 A * 5/1990 Hillstead ............... A61M 25/10
606/159
5,016,614 A * 5/1991 MacAllister ...... A61M 16/0429
128/207.14

(Continued)

FOREIGN PATENT DOCUMENTS

CN  202505930 U  * 10/2012
CN  208709847 U  *  4/2019
(Continued)

OTHER PUBLICATIONS

International Search Report and Written Opinion, Appl. No. PCT/EP2017/082658, dated Apr. 5, 2018.
(Continued)

*Primary Examiner* — Kathryn E Ditmer
(74) *Attorney, Agent, or Firm* — Fox Rothschild LLP

(57) ABSTRACT

An endotracheal tube inserting device (1;1') of the kind comprising a stylet part (3; 3'), a handle part (2;2'), and an endotracheal tube (1) on the stylet part (3), and a tube ejecting mechanism (65; 65') to advance the endotracheal tube off the stylet part (3; 3') once inserted in the correct position inside the patient's airways.

34 Claims, 21 Drawing Sheets

Figure 1:
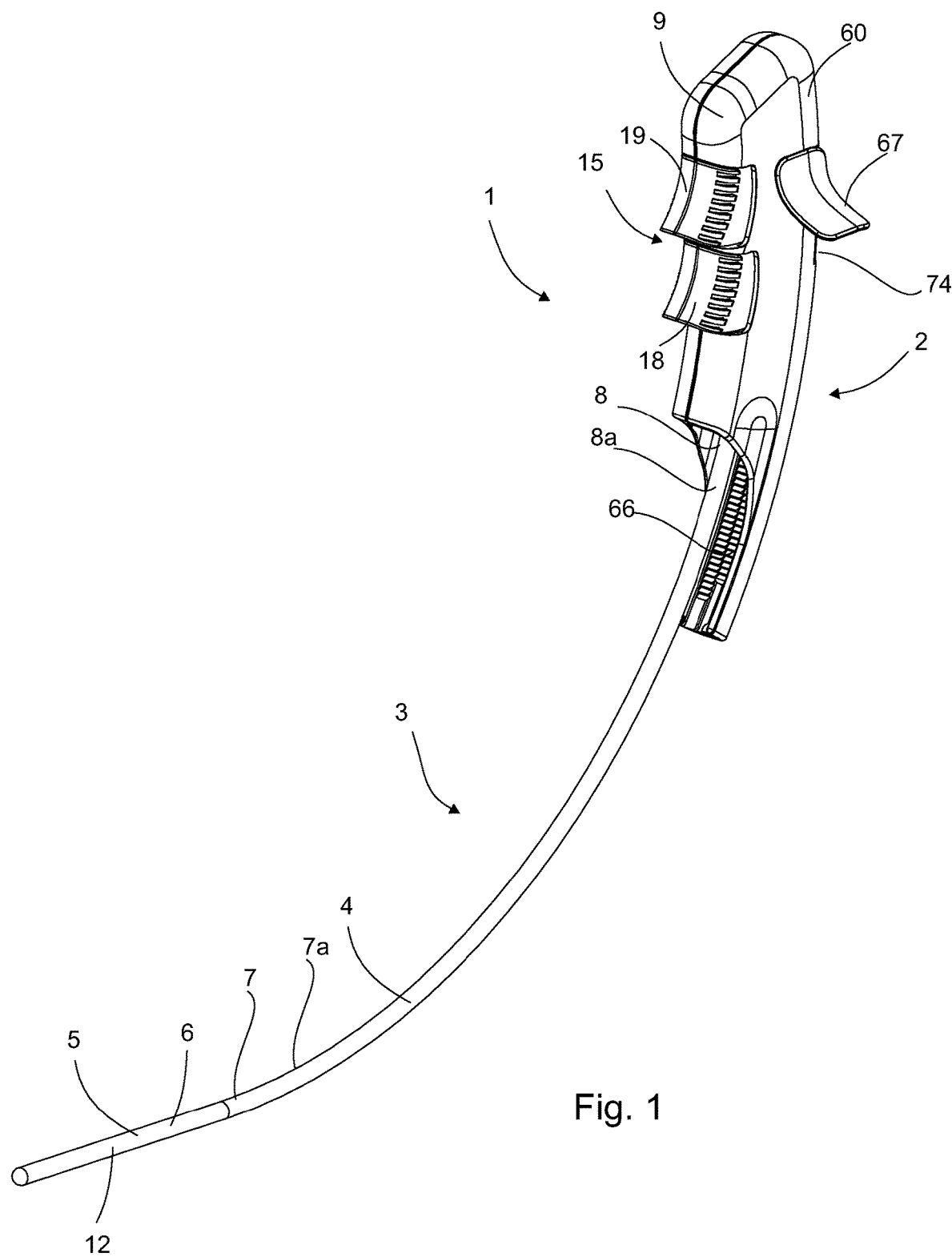

(51) Int. Cl.
*A61B 1/267* (2006.01)
*A61B 1/00* (2006.01)
*A61M 25/01* (2006.01)

(52) U.S. Cl.
CPC ......... *A61B 1/267* (2013.01); *A61M 16/0418* (2014.02); *A61M 25/0102* (2013.01)

(56) References Cited

U.S. PATENT DOCUMENTS

| | | | | |
|---|---|---|---|---|
| 5,327,881 | A * | 7/1994 | Greene | A61B 1/2676 600/120 |
| 6,539,942 | B2 | 4/2003 | Schwartz et al. | |
| 7,341,574 | B2 * | 3/2008 | Schreijag | A61D 1/025 604/209 |
| 8,382,665 | B1 | 2/2013 | Fam | |
| 9,283,342 | B1 * | 3/2016 | Gardner | A61B 1/00154 |
| 2002/0177750 | A1 | 11/2002 | Pilvisto | |
| 2003/0024532 | A1 * | 2/2003 | Sniadach | A61B 13/00 128/205.13 |
| 2004/0064136 | A1 * | 4/2004 | Papineau | A61B 18/148 606/41 |
| 2011/0295068 | A1 * | 12/2011 | Petersen | A61B 1/0014 600/131 |
| 2013/0035548 | A1 * | 2/2013 | Ianchulev | A61B 1/00052 128/200.26 |
| 2013/0220345 | A1 * | 8/2013 | Allphin | A61M 16/0495 128/860 |
| 2013/0245372 | A1 | 9/2013 | Lo | |
| 2013/0255671 | A1 * | 10/2013 | Furman | A61M 16/0488 128/200.26 |
| 2014/0180286 | A1 * | 6/2014 | Marczyk | A61B 17/2909 606/49 |
| 2015/0096556 | A1 | 4/2015 | Marks | |
| 2015/0297071 | A1 * | 10/2015 | Hung | A61B 90/30 600/120 |
| 2017/0000990 | A1 * | 1/2017 | Gerrans | A61M 29/00 |
| 2017/0367846 | A1 * | 12/2017 | Greenhalgh | A61B 17/1659 |
| 2018/0250484 | A1 * | 9/2018 | McCormick | A61B 1/2733 |
| 2020/0054849 | A1 * | 2/2020 | Venticinque | A61M 29/02 |

FOREIGN PATENT DOCUMENTS

| | | | |
|---|---|---|---|
| CN | 215504968 | U * | 1/2022 |
| EP | 1224904 | A2 | 7/2002 |
| EP | 1803481 | A2 | 7/2007 |
| JP | 2011062459 | A * | 3/2011 |
| WO | WO2009026095 | A1 | 2/2009 |
| WO | WO2011025297 | A2 | 3/2011 |
| WO | WO2011119521 | A1 | 9/2011 |

OTHER PUBLICATIONS

M. Chandler, Apparatus, "Tracheal Intubation And Sore Throat: a Mechanical Explanation", Anaesthesia, 2002, 57, pp. 155-161 (Year 2002).

Rose DK, Cohen et al., The Airway Problems and Predictions in 18,500 Patients, Can Journal of Anaesthesia, 1994, 41 ( 5 ), pp. 372-383, (year 1994).

C.M . Burket et al., Airway Management After Failure To Intubate By Direct Laryngoscopy: Outcomes In A Large Teaching Hospital, Can Journal of Anaesthesia., 2005, 52 (6), pp. 634-640 (Year 2005).

* cited by examiner

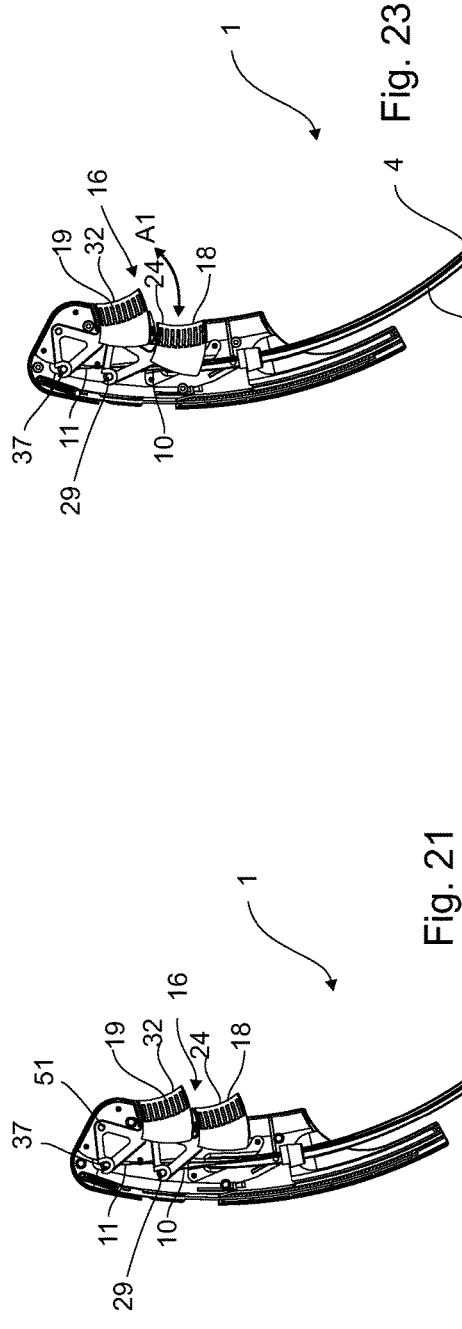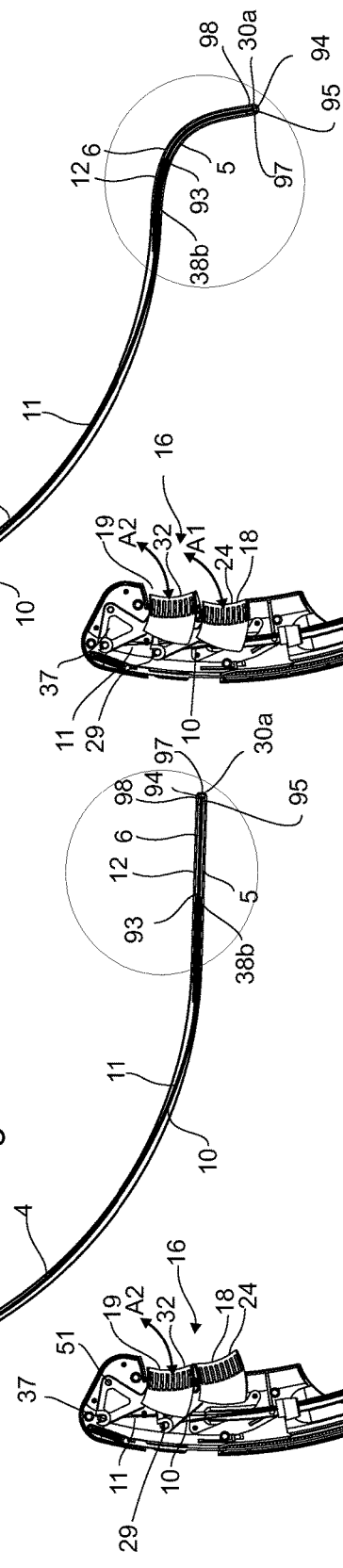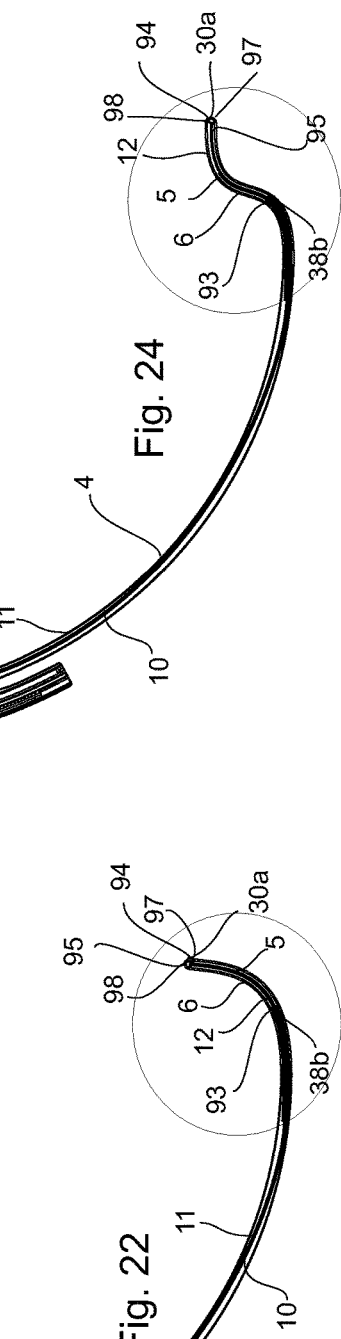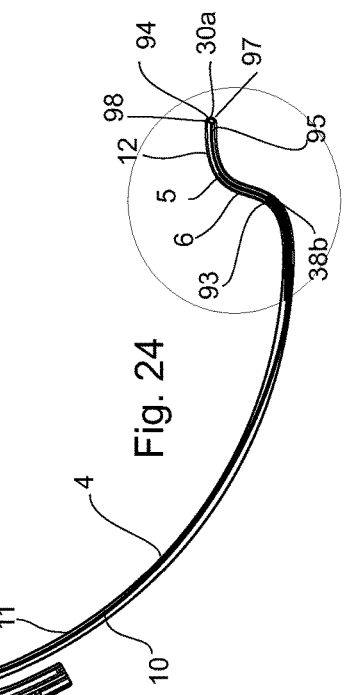

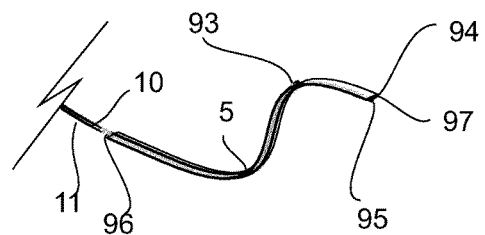
Fig. 25
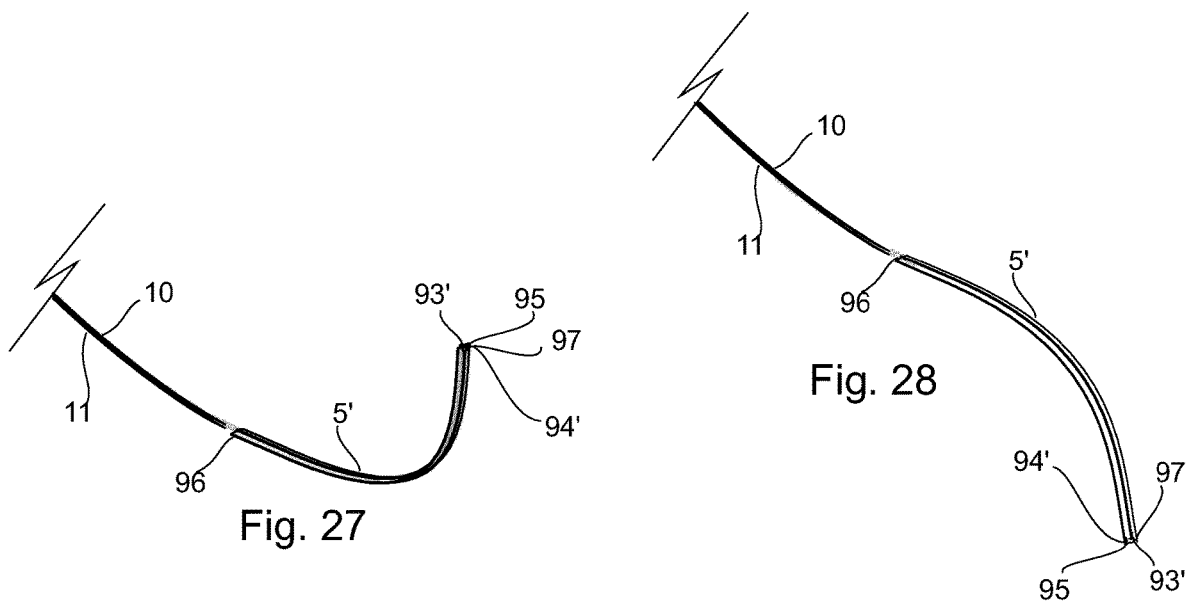
Fig. 27
Fig. 28
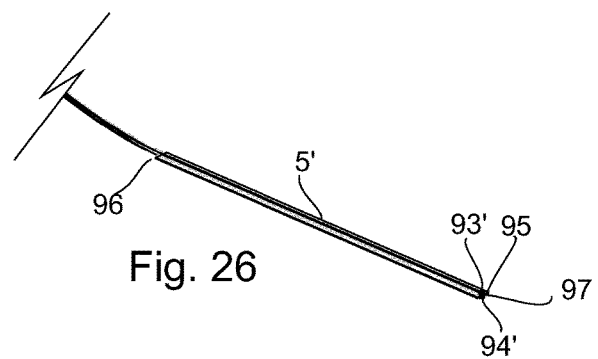
Fig. 26

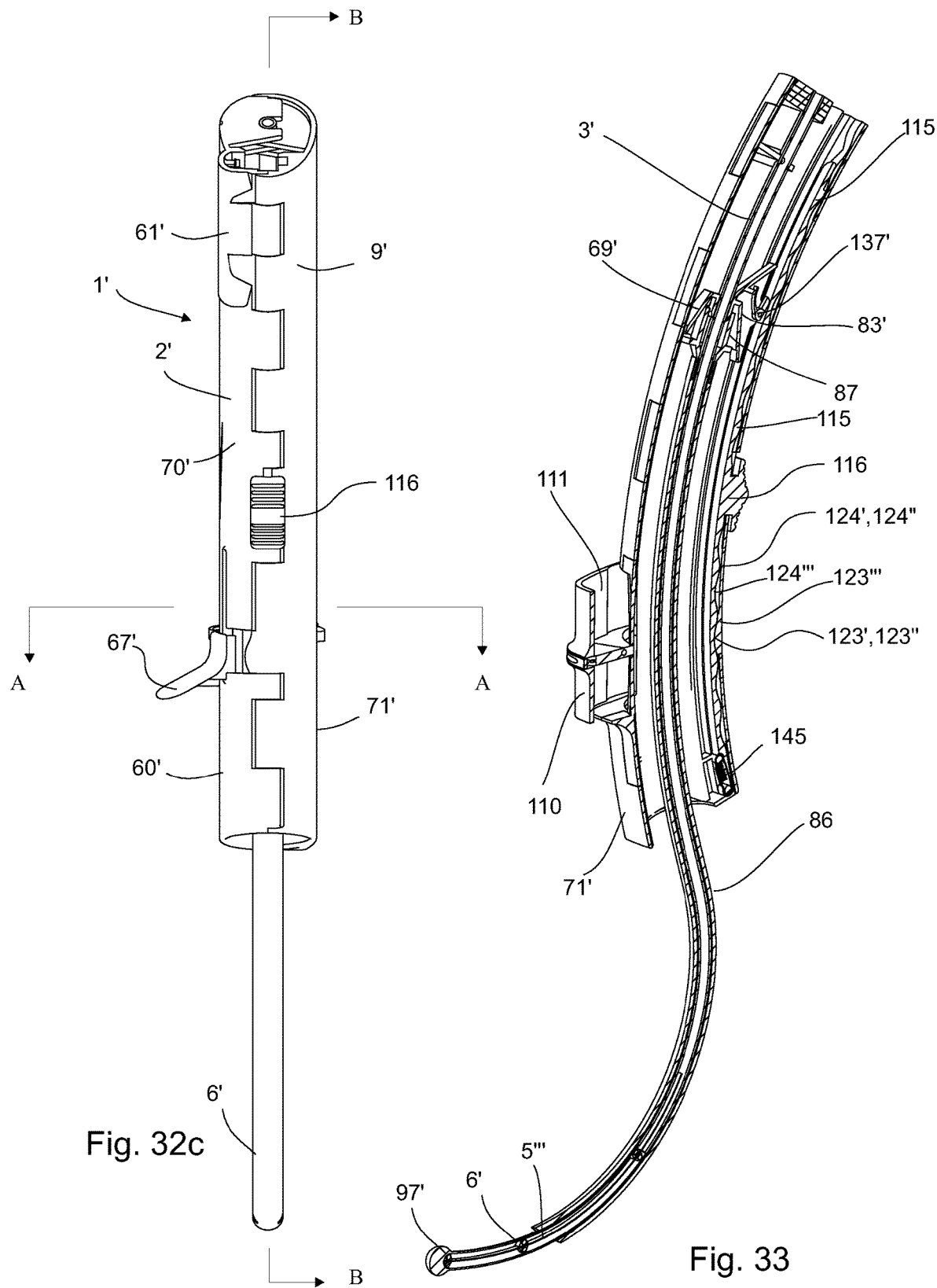

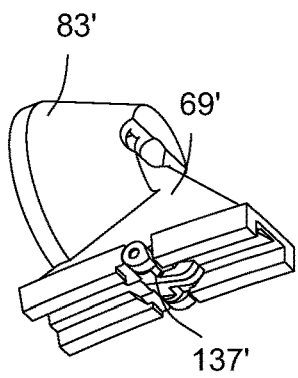
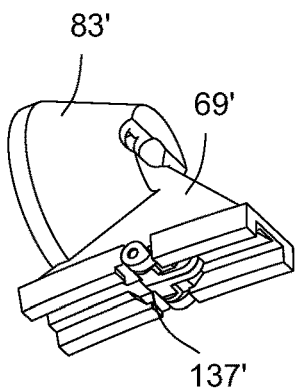
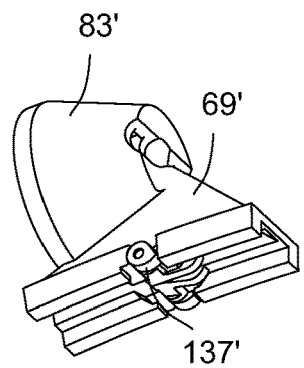
Fig. 39a    Fig. 39c    Fig. 39e
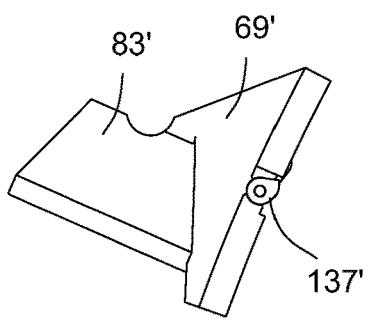
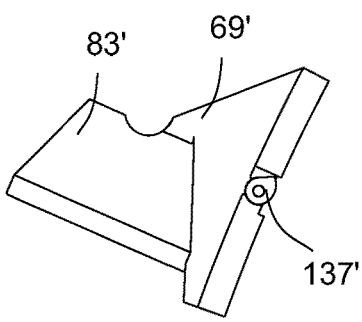
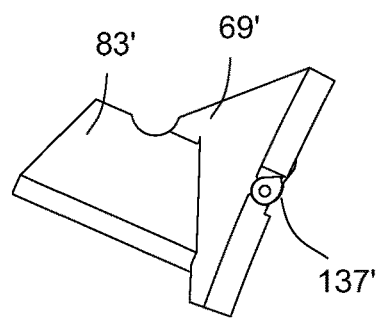
Fig. 39b    Fig. 39d    Fig. 39f
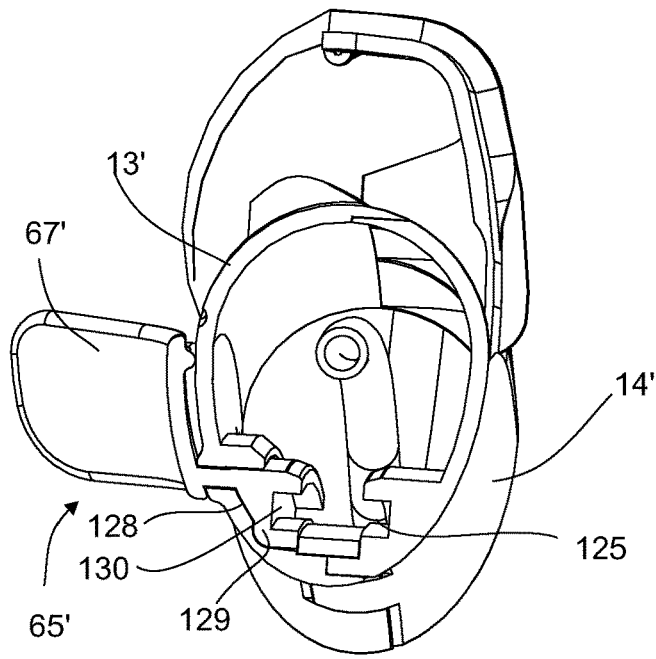
Fig. 42

ENDOTRACHEAL TUBE-INSERTING DEVICE

The present invention relates to an endotracheal tube inserting device of the kind comprising a stylet part, which has a proximal stylet end part with a proximal stylet end and an opposite distal stylet end part with a distal stylet end, and a handle part, wherein the stylet part is stationary in relation to the handle part, and an endotracheal tube on the stylet part of the endotracheal tube inserting device.

In particular the present invention relates to endotracheal intubation, and apparatuses and methods useful in the positioning of an endotracheal tube within the airways of a patient.

The term "endotracheal tube-inserting device" used in the context of the present application means a device adapted for inserting an endotracheal tube into trachea. The "endotracheal tube-inserting device" is an intubator, thus a device for controlling, directing, and placing an intubation tube within the trachea.

Unsuccessful direct laryngoscopy for orotracheal intubation occurs in particularly for patients having a "difficult airway". Failure incidence has been reported to be as high as 0.3% to 0.43% in the studies of Rose D K, Cohen M M. The airway: problems and predictions in 18,500 patients. *Can J Anaesth*. 1994; 41(5):372-383. doi: 10.1007/BF03009858, and of Burkle C M, Walsh M T, Harrison B A, Curry T B, Rose S H. Airway management after failure to intubate by direct laryngoscopy: outcomes in a large teaching hospital. *Can J Anaesth*. 2005; 52(6):634-640. doi: 10.1007/BF03015776.

Various kinds of blades and stylets are known in the art to improve the visuality of the airways when intubating a patient.

Even though it may still be a huge challenge to help guide the tube into and along the patient's trachea, including lifting vallecula out of the way, trapping epiglottis to better expose the glottis and vocal cords.

Laryngoscopes are therefore often used to obtain a view of the glottis or the larynx, or to manipulate the tongue, glottis or larynx in order to facilitate insertion of an endotracheal tube or other instruments, such as endoscopes.

Even though airway related complications associated with intubation procedures still occur. Examples of such complications include but are not limited to abrasion, hematoma, lacerations to lips, tongue, palate, pharynx, hypopharynx, larynx, and esophagus, injuries to lingual and/or hypoglossal nerve.

So despite the availability of various stylets and other implements, the insertion of endotracheal tubes can be difficult even for skilled physicians, particularly in patient's having anterior trachea and other conditions that make it challenging to guide the distal end of the endotracheal tube past the vocal cords and into the trachea.

As a tool to remedy at least some of the above side effects today widespread use is made of a video laryngoscope, such as a GlideScope® (Verathon, Inc., Bothell, Wash.), for real-time viewing a patient's airways during the intubation. This procedure has improved visuality of the airways significantly. Video laryngoscopes are however today used with rigid stylets, e.g. the GlideScope® is used with the GlideRite® Rigid Stylet that has a preformed curvature. Other rigid stylets can be bend to a given preformed curvature but the tip has no individual maneuverability.

A typical conventional stylet contains a single flexible wire with a PVC coating and a uni-directional end cap that prevents the stylet from moving forward during the intubation process to lower the risk of unnecessary trauma to the patient. The stylet is inserted into the endotracheal tube so that the tube connector engages the uni-directional end cap.

US patent application no. 2013/255671 discloses an articulating stylet device having the ability to bend an endotracheal tube in more than one direction while the tube is being positioned in a patient's airway. This known articulating stylet is comprised of a plurality of beads arranged in sequential series. Each series is composed of differently configured beads having adjacent angled or beveled end surfaces. This known stylet is given sufficient rigidity to keep elongate but bendable shape by keeping the beads intimately together on metal wires, and has special tensioning means for that purpose. However it is a challenge to arrange the bead correctly on the metal wires and a challenge to tension the wires correctly after all beads have been arranged as intended.

A further major disadvantage of this known stylet is that the beads inevitably become slightly dislocated if tensioning of a wire is unsuccessful, or if the wire is too slack. The angled or beveled end surfaces of two adjacent beads need to be arranged in intimate contact to prevent jamming of the beads. If tensioning is lost the string of beads get too slack and cannot keep required dimensional shape to constitute a stylet for inserting an endotracheal tube, and if just a single bead becomes slightly offset or dislocated the string of bead cannot be bend as intended. A further huge disadvantage is that the gap between two adjacent beads may accidentally pinch and injure the endotracheal tube on the bead stylet, and dislocation of beads may increase stylet diameter and prevent its retraction from the endotracheal tube.

U.S. Pat. No. 8,382,665 B1 discloses an endotracheal tube placement system including a placement-assistive handle, an oral anchor, a straight mechanized advancer, and an integrated video viewing system. The motorized or mechanical mechanized advancer is operational to advance a stylet and an endotracheal tube carried by the stylet as a combined unit. The mechanized advancer is directly attached to an endotracheal tube lock.

An endotracheal tube stabilizer is configured as a hollow tube-like supportive sheath, sized to allow the endotracheal tube manipulator that carries the endotracheal tube progress through it, upon engagement of an advancer trigger by the clinician. The advancer trigger is operative to prompt the mechanized advancer to propel forward through the tube stabilizer and forward of the oral anchor the combined endotracheal tube lock and endotracheal tube manipulator while it carries the endotracheal tube. The mechanized advancer that propels the endotracheal tube lock, endotracheal tube manipulator, and the endotracheal tube forward together until the endotracheal tube is in the proper position is not a tube ejecting mechanism. Once the proper position is reached the endotracheal tube and oral anchor remain in position while the endotracheal tube lock and endotracheal tube manipulator are removed.

International patent application no. WO2011/119521 discloses an intubating device that mechanically can deploy an endotracheal tube into the trachea while eliminating the need for the operator to remove a hand from the device in order to manually advance the endotracheal tube along the stylet and into the trachea, while attempting to maintain a steady position of the device with the other hand. The stylet is a multi-lumen stylet that is so flexible that it can form loose coils or folds within a cavity of a corresponding housing. In use an endotracheal tube is disposed on the distal end of a support member around the housing for the coiled or folded stylet so as to surround and be coaxial with the stylet. A support member driver assembly, which supports the support member on the outer surface of the housing, is configured to advance the support member together with the endotracheal tube along the stylet in a direction away from the housing upon actuation of a trigger disposed on a handle. In, addition, the support member driver assembly is configured to automatically release the endotracheal tube from its attachment to the connector portion upon movement of the support member in a direction towards the handle portion. This known device has no means to displace the endotracheal tube along the stylet.

International patent application no. WO2009/026095 discloses an apparatus for intubating an airway of a patient with an endotracheal tube. The apparatus includes a housing and a motive mechanism, that is supported by the housing and provides a user interface structure. A tube coupler is operatively coupled to the motive mechanism and is connectable to the proximal end of the endotracheal tube. A stylet coupler is operatively coupled to the motive mechanism and is connectable to a proximal end of an intubation stylet for motion relative to the housing. The motive mechanism is operable to move the tube coupler in a first direction relative to the housing and to simultaneously move the stylet coupler in a second opposite direction relative to the housing in response to actuation of the user interface structure. The tube coupler cannot be moved without also moving the stylet coupler to withdraw the stylet from said endotracheal tube. The tip of the endotracheal tube is impossible to place and keep in the exact position of use. Instead this exact position of use must be predetermined, calculated and/or guessed because when the stylet is withdrawn the endotracheal tube automatically moves forward and vice versa.

A problem with these prior are devices is to get the endotracheal tube off the stylet part once the endotracheal tube inserting device with the endotracheal tube sheathed on the stylet part is in the desired position inside the patients airways, and at the same time ensure that the endotracheal tube does not get off the stylet part too early, ends up having ventilation holes at a deficient position for ventilation, bellows on the stylet part, or comes along when the stylet part is withdrawn.

It is a main aspect of the present invention to provide an alternative endotracheal tube inserting device of the kind mentioned in the opening paragraph, in particular for endotracheal intubation.

It is yet an aspect of the present invention to provide an endotracheal tube inserting device of the kind mentioned in the opening paragraph by means of which an endotracheal tube can easier be positioned in a patient with a challenging anatomy than hitherto known.

It is yet an aspect of the present invention to provide an endotracheal tube inserting device of the kind mentioned in the opening paragraph for facilitated displacement of the endotracheal tube off the stylet part.

It is yet an aspect of the present invention to provide an endotracheal tube inserting device of the kind mentioned in the opening paragraph for preventing unintended displacement of an endotracheal tube sheathed on the stylet part during the endotracheal insertion procedure.

It is yet an aspect of the present invention to provide an endotracheal tube inserting device of the kind mentioned in the opening paragraph for use together with a video laryngoscope.

It is yet an aspect of the present invention to provide an endotracheal tube inserting device of the kind mentioned in the opening paragraph wherein the stylet part is disposable.

It is yet an aspect of the present invention to provide an endotracheal tube inserting device of the kind mentioned in the opening paragraph by means of which the risk of accidental insertion of an endotracheal tube in the esophagus is reduced significantly.

It is yet an aspect of the present invention to provide an endotracheal tube inserting device of the kind mentioned in the opening paragraph by means of which the risk of accidental injuring the patient's airways during intubation is reduced.

It is yet an aspect of the present invention to provide an endotracheal tube inserting device of the kind mentioned in the opening paragraph for use in an endotracheal procedure that is fast, efficient, and safe to the patient.

It is yet an aspect of the present invention to provide an endotracheal tube inserting device of the kind mentioned in the opening paragraph wherein the stylet part is stationary secured to the handle and the endotracheal tube is displaceable on the stylet part.

It is yet an aspect of the present invention to provide an endotracheal tube inserting device of the kind mentioned in the opening paragraph which is smooth and ergonomic to operate.

It is yet an aspect of the present invention to provide an endotracheal tube inserting device of the kind mentioned in the opening paragraph that has means to retract the endotracheal tube towards the proximal stylet end if the attempt to eject the endotracheal tube was unsuccessful when attempting to position the endotracheal tube.

The novel and unique whereby these and other aspects are achieved according to the present invention consist in that the endotracheal tube inserting device has a tube ejecting mechanism adapted for displacing the endotracheal tube along the elongate stylet part in a direction towards the distal stylet end of the elongate stylet part to facilitate getting the endotracheal tube off the stylet part.

Within the context of the present application the term "proximal" is used to indicate a position nearest to the handle part and the term "distal" is used to indicate a position nearest the bendable tip part. The term "housing" is used for a receptacle that is hollow to accommodate at least some of the mechanisms to operate the endotracheal tube inserting device. The term "support" in context of the present application means that the elongate guide member "supports" the string members, which means that the string members run close to the major part of the elongate guide member to guide said string members.

The stylet part provides stiffness to the endotracheal tube to facilitate advancement of the endotracheal tube into the patient's airways without the endotracheal tube puckers or otherwise has its use-configuration damaged or altered.

The tube ejecting mechanism facilitates a displacing of the endotracheal tube along the stylet part until a smooth and gentle ejecting of the endotracheal tube off the stylet part is conducted to the benefit of both the structural integrity and shape of the endotracheal tube as well as to the comfort of the patient. The tube ejecting mechanism pushes the endotracheal tube at least partly off the stylet part, thereby reducing area of endotracheal tube in contact with stylet part and avoiding that said endotracheal tube clings to the stylet part during retraction of said stylet part, thereby also ensuring that the tip of the endotracheal tube is left in the exact intended position needed for assisted ventilation of the patient. So instead of starting to pull the stylet part free of the endotracheal tube as in conventional endotracheal procedures, or simultaneously advancing the endotracheal tube and retracting the stylet part from said tube, the first separation step between endotracheal tube and stylet part is a displacing step in which the endotracheal tube is started to be moved free of the stylet part. Thus due to the tube ejecting mechanism the risk is highly reduced or even eliminated that the endotracheal tube comes along when retracting the stylet part, because frictional contact is also reduced.

A tube ejecting mechanism suited for use with the endotracheal tube inserting device of the present invention may comprise different kinds of ratchet mechanisms to facilitate ejection of the endotracheal tube at least partly off the stylet part, and to keep the endotracheal tube in gradually advanced positions in relation to the stylet part during ejecting.

The ratchet mechanism may advantageously comprise a rack part extending along at least a length of the handle part and being arranged opposite a wedge part associated with the stylet part in order to engage the rack part to drive the endotracheal tube off the stylet part. Optionally the wedge part can protrude from a tube connector associated with the stylet part.

Within the context of the present invention the term "tube ejecting mechanism" is to be understood as a mechanical means able of moving the endotracheal tube along the stylet part towards its distal stylet end as a reaction on a physical force, thereby moving the endotracheal tube forward on the stylet part. Optionally the tube ejecting mechanism can also set the endotracheal tube free of the tube connector and/or the wedge part once its distal tip is in intended position. Alternatively, the endotracheal tube and the tube connector are decoupled manually using the fingers.

Within the context of the present invention the term "ratchet mechanism" is to be understood as a mechanism that has spaced apart protrusions between which another object can engage. The protrusions can e.g. be inclined teeth to engage inclined teeth on the other object, such as teeth on the wedge part. In the alternative the protrusions can be crests of a waveform to engage a corresponding waveform on the other object, e.g. the wedge part, a component associated with the wedge part, or the moveable fourth rack part described below.

A reciprocating third actuator may advantageously serve for operating the ratchet mechanism to stepwise move a tube connector, and thus the endotracheal tube sheathed on the stylet part, along the elongate stylet part towards the distal stylet end of the stylet part. The third actuator is preferably provided protruding from the handle part to be accessible from outside said handle part.

The tube connector can expediently be configured to mate an airway connector of the endotracheal tube and if the tube connector is being slidingly arranged in association with the stylet part the endotracheal tube can be firmly secured to the stylet part, and be given an exact position on and in relation to the stylet part both prior to and during displacing and ejecting since all of the length of the endotracheal tube, the length of the stylet part, and the length of a stroke of the third actuator are well-known factors. By application of a certain number of strokes of the third actuator the operator knows how far the endotracheal tube is ejected from the stylet part at all times. The number of strokes can be one.

If the tube connector is a conical tube connector it fits together with different diameters of airway tube connectors, so that one endotracheal tube inserting device of the present invention can be used with many different endotracheal tubes having lengths suited for the length of the respective stylet part.

The rack part may in a preferred first embodiment of a tube ejecting mechanism include a first stationary rack part, a second stationary rack part, and a moveable third rack part arranged lengthwise between the first stationary rack part and the second stationary rack part. Preferably said rack parts are elongate, optionally said rack parts can follow the curvature of a housing of the handle part.

The handle part may advantageously comprise the housing for accommodating and protecting components of the endotracheal tube-inserting device, such as at least some of a proximal stylet end part, a proximal end of the string members, at least a part of the tube ejecting mechanism, and at least a part of the actuation means. The housing may have various shapes depending on the configuration of said components. An ergonomic, easy graspable and maneuverable shape of the handle part may be preferred.

The third actuator can be part of, integral with or solid with the moveable third rack part and protrudes outside the handle part to be operated e.g. by the thumb of the operator who grasps on the handle part. So the moveable third rack part may have the third actuator arranged to protrude from the handle part, e.g. from the housing of the handle part, so as to be accessible for a user in a reciprocating manner from outside the handle part, e.g. from outside the housing as described in more details later.

The rack parts can advantageously be elongate structures having lengths substantially larger than width, e.g. the width is just between 5-15% of the length. Furthermore, the stationary rack parts may be integrally formed with the handle part, e.g. with a housing of the handle part.

In some embodiments the moveable third rack part can advantageously move the endotracheal tube stepwise off the stylet part due to the moveable third rack parts engagement with the wedge part, and the stationary rack parts advantageously serves to maintain the endotracheal tube in the advanced position.

In some embodiments of a tube ejecting mechanisms the moveable third rack part and/or a feeder component configured to displace the wedge part towards the distal stylet end can return to a starting position due to a rack end of the moveable third rack part and/or the feeder component being suspended inside the handle part, e.g. to an interior part of the handle part, to an interior face of the housing or any other structure associated with the handle part, by means of a retraction means or a resilient means, such as e.g. a respective spring member. A spring member can be stretched when the third actuator is moved lengthwise along the handle part in order to displace the moveable third rack part lengthwise between the length of the first stationary rack part and the length of the second stationary rack part or displacing the feeder component along the length of the first stationary rack part and the length of the second stationary rack part.

Due to the inertia applied to the stretched spring, the spring automatically returns to a more relaxed starting position once the force applied to the third actuator is relieved, thereby pulling the third actuator and the moveable third rack part or the feeder component with the third actuator back to the starting position, and thereby allowing repetition of a similar actuation of the moveable third actuator to perform a new stroke if needed, and thus to displace the tube connector further towards the distal stylet end, thereby also moving the endotracheal tube along and off the stylet part.

Other kinds of tensioning and retractions means than springs are within the scope of the present invention. Any means having shape-memory and being able to reassume a relaxed state and be deformed into another shape can be used instead of the spring, such as elastic means or compressible means.

For the wedge part to engage the rack parts, on the one hand to advance and displace the endotracheal tube along the stylet part during a downwards stroke of the third actuator, and on the other hand to keep this advanced position during the third actuator's, and thus the moveable third rack part's returning to the starting position at the proximal end of the housing, can the proximal end of the wedge part be provided with opposite lateral wedge parts and with a center wedge part located between said lateral wedge parts. Optionally the tube connector can be provided at the opposite distal end of the wedge part.

The first stationary rack part may have first teeth, the second stationary rack part may have second teeth, and the moveable third rack part may have third teeth, so that the center wedge part can engage the moveable third rack part. In one embodiment the center wedge part can engage between the teeth of the moveable third rack part, and the opposite lateral wedge parts of the wedge part can engage the first teeth and the second teeth.

In the context of the present invention the term "opposite lateral wedge parts" means that the two lateral wedge parts are provided on opposite sides of the "center wedge part". In connection with the terms "lateral wedge part" and "center wedge part" the term "wedge part" a component that can be driven against another object to secure against said object. A "lateral wedge part" and a "center wedge part" have a free end that can be secured between two other objects or parts, or attack on another object to secure a "lateral wedge part" or the "center wedge part" in relation to said other object. Optionally any of a "lateral wedge part" and a "center wedge part" may have a tapering free end.

In the above embodiment of a ratchet mechanism the lateral wedge parts can thus engage the teeth of the first stationary rack part and second stationary rack part to keep the wedge part and the tube connector in the lengthwise forwarded and advanced position while the moveable third rack part returns to its starting position to be able to repeat the step of a stroke by actuating the moveable third actuator to move the wedge part and the tube connector further forward towards the distal stylet end. So the engagement between the lateral wedge parts and the teeth of the stationary rack keeps the tube connector in the moved-forward position wherefrom backwards movement is impossible due to the lateral wedge parts being trapped between the teeth of the stationary rack parts. The third teeth of the moveable third rack part may however serve as the tool for every further forward movement of the wedge part until the third teeth and center wedge part engage again closer to the distal stylet end until the endotracheal tube is moved so far down the trachea that the stylet part can be withdrawn without the endotracheal tube comes along. Preferably the third teeth are forward angled.

So in this embodiment both the moveable third rack part, the first stationary rack part, and the second stationary rack part may have a plurality of teeth alternating with a plurality of grooves and extending crosswise the length of the respective rack part to catch an opposite facing part of a wedge part thereby, on the one hand preventing the wedge part from returning towards the housing of the handle part, and on the other hand facilitating further forward movement of the wedge part. The teeth of at least the stationary rack parts may conveniently be angled towards the proximal stylet end, and the grooves between adjacent teeth be designed to mate with the lateral wedge parts of the wedge part, while the central wedge part mate with the third teeth. To ensure good engagement the lateral and center wedge parts may taper to a thin edge towards the multiplicity of teeth to lock between these teeth.

Alternative designs, positions, angles and/or inclinations of the respective teeth on the rack parts in order for the rack parts to properly engage any of the lateral wedge parts and the center wedge part are within the scope of the present invention if such are suitable to ensure the engagement between teeth, wedge parts and rack parts.

The tube ejecting mechanism of an endotracheal tube inserting device according to the present invention may be provided with other kinds of ratchet mechanisms than the above-described for facilitating ejection of the endotracheal tube and for keeping the endotracheal tube in gradually advanced positions. Within the scope of the present invention various arrangements, designs and positions of the rack parts, the center wedge part and the opposite lateral wedge part of the ratchet mechanism are foreseen and possible.

For example can the lateral wedge parts and the center wedge part be provided at the wedge part between the proximal end of the wedge part and the distal end of the wedge part, thereby allowing the opposite lateral wedge parts to engage the first teeth and the second teeth. Optionally the tube connector can be provided at the proximal end of the wedge part.

Good and reliable engagement can take place if any of the first teeth, second teeth, and third teeth are tapered, such as pointed, blunt, or crest-shaped.

In an alternative embodiment of a ratchet mechanism of the present invention, said ratchet mechanism may comprise that
- the feeder component is configured with the third actuator for moving the wedge part towards the distal stylet end, the wedge part is slidable received by the feeder component and slidable mounted on the stylet part,
- the wedge part may have a shaft bearing that extends crosswise a first wedge face facing the stationary rack parts and an opposite second wedge face,
- the shaft bearing can be configured for pivotably receiving a pivoting pawl member,
- which pivoting pawl member may have means to engage at least the feeder component to drive the wedge part towards the distal stylet end.

The above alternative embodiment of a ratchet mechanism differs amongst others from the first embodiment in that it is not the moveable third rack part that moves the wedge part down along the stylet part. Instead the third actuator can be provided on a feeder component and protrude from the housing to be accessible from outside said housing in the same manner as described for the first embodiment of an endotracheal tube inserting device. The means for displacing the wedge part towards the distal stylet end may advantageously be the pivotable pawl member that, due to being pivotable suspended in the shaft bearing, may be able to attack at least the feeder component to drive the wedge part at least a part of a stroke in the direction along the stylet part towards the distal stylet end of said stylet part. The endotracheal tube inserting device may also be configured to allow the feeder component to repeat a stroke, e.g. in a manner similar to elongate movable third rack part of the first embodiment of an endotracheal tube inserting device due to spring means. The feeder component can return towards the proximal stylet end when the actuation force on the third actuator on the feeder component is relieved thereby also relieving the attack on the feeder component and leaving the wedge part in the advanced position.

To allow the wedge part to slide in relation to the housing the interior of the housing may be configured with a first internal track for slidingly receiving a first sliding flange of the wedge part, and a second internal track for slidingly receiving the feeder component, which feeder component may have a third internal track for receiving a second sliding flange of the wedge part.

The first sliding flange can slide in the first internal track along the length of the housing, and the second sliding flange can slide in the third internal track. The third actuator on the feeder component may protrude through a feeder slot in the housing of the handle part; the length of said feeder slot may define the maximum length of a stroke by the third actuator. The feeder component may advantageously be slidingly arranged in the second internal track opposite the first internal track, so that when no pressure or force are applied to the third actuator the feeder component can return towards the proximal end of the housing by sliding inside the second internal track to be repositioned for a new stroke by actuating the third actuator again.

The pivoting pawl member may be suspended on a shaft body that is positioned to allow a main body of the pawl member to slide inside the third internal track and/or the first internal track.

The pivoting pawl member may in an alternative advantageous embodiment include that the first lateral wedge part is provided as a first lateral pawl member, which is pivotable and slidable arranged in the first internal track, and the opposite second lateral wedge part is provided as a second lateral pawl member, which is pivotable and slidable arranged in the third internal track.

Advantageously the pivoting pawl member can be located in the shaft bearing that traverses the first surface of the wedge part to conveniently be suspended on a shaft that has the first lateral pawl member located to protrude inside the first internal track and the second lateral pawl member located to protrude inside the second internal track thereby allowing the pivoting pawl member to pivot, e.g. an angle of between 6-12° towards and away from the first surface of the wedge part.

For example the opposite first and second lateral pawl members may be independently pivotable, preferably be separate members, but within the scope of the present invention the pawl member can be a single unit.

Instead of protruding in lengthwise extension of the wedge part the opposite lateral wedge parts in form of opposite first and second lateral pawl members may in this embodiment protrude from the respective opposite free ends of the main body of the pawl member substantially perpendicular to the axis of said main body.

The center pawl member may protrude substantially perpendicular to the axis of the main body between said first and second lateral pawl members and angularly displaced on the main body from said first and second lateral pawl members so that said center pawl member can operate free of the lateral wed parts.

In on embodiment the center pawl member can have a first center pawl member integral with the first lateral pawl members and a second lateral pawl member integral with the second lateral pawl member, thus being able to pivot as separate units and be subjected to individual forces when sliding inside an internal track.

Sometimes the first attempt of ejecting the endotracheal tube off the stylet part is unsuccessful and reposition needed. Instead of needing to start the whole intubation procedure from scratch, the present invention has means for returning the misplaced endotracheal tube from its forward displaced position towards the distal stylet end back in the direction towards the proximal stylet end to start again. The stylet part need not be withdrawn but can stay in situ and it is possible to conduct one or more further attempts to place the ventilation openings and the cuff of the endotracheal tube in the correct position.

A means for returning an endotracheal tube that has been displaced towards the distal stylet end back in the direction towards the proximal stylet end may include that the first teeth of the first stationary rack part and the second teeth of the second stationary rack part together can define an elongate rack part groove for receiving and engaging fourth teeth of an elongate moveable fourth rack part that faces the combined first teeth and second teeth, which moveable fourth rack part optionally can have a fourth actuator protruding outside the housing for, upon actuation, returning the wedge part with the endotracheal tube towards the proximal stylet end. The first and second center pawl members can apply same or different level of force on the back side of the elongate moveable fourth rack part to move the moveable fourth rack part free of engagement with elongate rack part groove thereby lifting the lateral wedge parts free to slide towards the proximal stylet end inside the respective first and third internal tracks.

The center pawl member can be pivotable and slidable arranged on the main body between the opposite first and second lateral pawl members above a back side of the moveable fourth rack part located in said elongate rack part groove, which back side of the elongate moveable fourth rack part is the side opposite the fourth teeth.

The first and second lateral pawl members may have a tapered or pointed free part or be substantially wedge-shaped, thereby being asymmetrical around the shaft. The tapered shape of the second lateral pawl member of the wedge part allows said second lateral pawl members to take hold of the feeder component inside the third internal track when the third actuator is actuated by e.g. the thumb. The second lateral pawl member can thus almost hook up with the feeder component thereby moving the wedge part with the attached endotracheal tube along the stylet part towards the distal stylet end. And at the same time the first lateral pawl member slides inside the first internal track and the center pawl member slides smoothly on or is free of contact with the moveable fourth rack part. The first lateral pawl member of the wedge part may serve to slide inside the first internal track to guide and control the wedge part when it moves forward.

The first face of the wedge part may further have an indent or stop associated with the main bearing part, which indent or stop is adapted for accommodating and restraining a spring arm protruding from the main body of the pivoting pawl member, which spring arm protrudes angularly displaced from both the first and the second lateral pawl members and from the center pawl member in an angular direction opposite to the center pawl member, optionally in substantially the same plane as the center pawl member. Thus angularly displaced from the first and second lateral pawl member, and from the center pawl member, in an angular direction opposite to the center pawl member. When the pivoting pawl member pivots in response to actuation of the third actuator on the feeder component, the spring arm is pressed inside the indent or hits the stop thereby being tensioned to increase grip between third internal track of the feeder component and second lateral pawl member. The tensioning of the spring arm may contribute in controlling the pressure from the second lateral pawl member on the third internal track of the feeder component. Optionally the spring arm may be composed of a first spring arm member on the first lateral pawl member and a second spring arm member on the second lateral pawl member whereby different forces can be applied to different lateral pawl members and to the first and second center wedge member. Optionally the spring arm may protrude in substantially the same plane as the center pawl member.

The indent may just be a recess, cavity, groove or similar, cut-out branching from the shaft bearing, preferably from a main bearing part of said shaft bearing, which indent can be suitable dimensioned to receive and tension the spring arm. The stop can be a pin of tab that the spring arm can hit on when pressed inside the wedge part when the feeder component makes a stroke forward and/or backwards.

The fourth teeth of the moveable fourth rack part may thus face the first teeth of the first stationary rack part and the second teeth of the second stationary rack part, thus face and engage the elongate rack part groove during operating the feeder component. Only when the endotracheal tube shall be repositioned to start from the top position again for repeating ejecting of the endotracheal tube the fourth actuator and the fourth moveable rack part may come into operation.

When pressing on the fourth actuator the fourth teeth can be moved free of engagement with the first and second teeth thereby lifting the moveable fourth rack part and tensioning the spring arm so that the center pawl member can become in frictional engagement with the back side of the moveable third rack part to stepwise move the wedge part back to its initial position. The first teeth, second teeth and the fourth teeth may be mating crests of opposite waveform so that when the peaks of opposite facing crests are just on top of each other the moveable fourth rack part is lifted maximum.

The reciprocation of the fourth actuator is limited by the length of a reciprocator slot, which is adjusted to move the moveable fourth rack part a distance corresponding to the distance between the peak of a crest and the deepest of a through between two adjacent crests.

Advantageously the shaft bearing can be a groove, track or recess dimensioned to allow the main body to pivot without substantial frictional wear, preferably without the main body drops out during pivoting when the third actuator reciprocates the feeder component along the length of the handle part to drive the tube connector and the wedge part forward. Optionally the shaft bearing can include a slot crosswise the wedge part and having an access opening for the main body along the length of said slot. The slot may have at least a section having a cylindrical cross-section adapted to receive the main body, and a width of the access opening can be slightly smaller than the diameter of the main body. The main body can then be snap-fitted into the shaft bearing and be kept pivotable arranged inside the slot without dropping out. Optionally the diameter of the main body may be slightly larger than the diameter of the shaft bearing to allow the main body to pivot smoothly. The angular width of the access opening, and optionally the length of one or more of the protruding pawl members and the protruding spring arm, the depth of the indent or distance to the stop, and the clearance between main body and shaft bearing may also determine the maximum angle that the main body is able to pivot about its axis inside the shaft bearing, and to determine the contact force of the lateral pawl members against respective internal tracks and/or force of the center pawl member against the back side of the moveable third rack part to drive the moveable third rack part.

At least one of the opposite lateral pawl members can be provided with friction increasing pads to increase friction when the lateral pawl members moves in the first internal track and the third internal track of the housing and of the feeder component respectively, thereby increasing gripping force and avoid unintended skating of the lateral pawl members inside an internal track, so that the wedge part is not brought along by the feeder component, as well as avoiding unintended wear of the lateral pawl members.

In a preferred embodiment the first teeth and the second teeth are formed integral with the handle part on an interior face of the handle part.

The endotracheal tube inserting device according to the present invention may further comprise one or more of
 the proximal stylet end is situated at the handle part, and the distal stylet end has an extension in form of a bendable tip part with a free distal end,
 a tip part operating member includes at least a first string member and a second string member arranged along the length of at least a length of the stylet part,
 the handle part has an actuator means for operating at least the tip part operating member,
 the first string member has a first proximal string end connected to a first string operating member of the actuator means and an opposite first distal string end secured at a first string-securing location at the bendable tip part,
 the second string member has a second proximal string end connected to a second string operating member of the actuator means and an opposite second distal string end secured at a second string-securing location at the bendable tip part, which second string-securing location is different from the first string-securing location, and
 the stylet part comprises an elongate guide member that extends into the bendable tip part, which elongate guide member and bendable tip part lengthwise can encase, support or guide at least a part of the first string member and at least a part of the second string member.

To conduct a laryngoscopic, orotracheal procedure the patient is first positioned so that the axial planes of the oral, pharyngeal and tracheal axes are aligned. The operator holds the laryngoscope, preferably a video laryngoscope, in his/her left hand. A cricoid pressure may be maintained, typically by another person assisting the operator, until the end of the procedure where the endotracheal tube is in correct place and the cuff has been inflated. The tip of the video laryngoscope is inserted into the right side of the patient's mouth and the blade is advanced to the base of the center wedge part, which is moved to the side, and the blade is moved forward. A straight blade is moved beneath the epiglottis and a curved blade is placed into the vallecula above the epiglottis keeping attention to keep the curved blade in midline and not applying traction along the axis of the laryngoscope handle as the laryngoscope lifts the center wedge part upwards away from the larynx to reveal the glottic opening and visualize the vocal cords. The endotracheal tube is then inserted through the vocal cords holding the stylet with the endotracheal tube with the right hand. An angled stylet may interfere with the passage of the endotracheal tube into the trachea and may cause difficult manipulation to pass through the vocal cords. Once the tip of endotracheal tube is past the vocal cords the stylet is removed, optionally the position of the endotracheal tube is corrected, the laryngoscope is removed, the cuff is inflated and safe insertion confirmed, e.g. by monitoring or observing end-tidal CO, listening using a stethoscope, observing condensation in the exterior length of the endotracheal tube, X-ray, etc. The skilled person knows these medical procedures.

Known stylets for use in the above intubation procedures either has a predetermined curvature or is bendable to be curved into the overall desired shape rather than bending just the bendable tip part.

For the present invention two separate string members, a first string member and a second string member, respectively, are secured at two different securing locations inside the bendable tip part to arbitrarily move the bendable tip part at least lengthwise. When a string member of the tip part operating member is operated independent of the other string member of the tip part operating member, via the actuator means of the handle part, either by a string member being tensioned of by relaxing tensioning of a string member, the respective string-securing locations are moved in relation to the distal end of the elongate guide member, thus where said elongate guide member extends distally into the bendable tip part. Because the string members can be operated separately almost any imaginable shape of the distally arranged bendable tip part can be given to it simply by pulling the two string members more or less. One string member can be operated or both string members can be operated at the same time. Same or different levels of tensioning can be applied to the first string member and the second string member.

In the operating state of the endotracheal tube inserting device the operator grasps around the handle part to operate the tip part operating member to almost arbitrarily move the first string member and/or the second string member lengthwise inside the elongate hollow guide member to bend the bendable tip part at the distal stylet end. The free end of the bendable tip part can e.g. be moved below or above the elongate hollow guide member, when seen in the operative orientation of the endotracheal tube inserting device, be given an S-shaped, be given a C-shape, an L-shape, of combination of any of these shapes. If the first string-securing location and the second string-securing location are radially different along the same or different circumference or outline of the bendable tip part, e.g. opposite each other the bendable tip part can also move to the side. Combinations of lateral offset and lengthwise offset first string-securing location and second string-securing location are within the scope of the present invention.

The elongate guide member and the bendable tip part safely sheath, support, guide and/or confine the first string member and the second string member so that the patient's tissue never can get in direct contact with any of the string members. Should the unimaginable accident occur that the first distal string end of the first string member disconnects from the first string-securing location and/or the second distal string end of the second string member disconnects from the second string-securing location such a detached end of a string member can never spring back to come in contact with patient's tissue and injure the patient. If the same happens for the beaded wire of the prior art stylet disclosed in US patent application no. 2013/255671 one or more beads could drop off the wire when the stylet is retracted from the endotracheal tube. Loose beads can in the best-case scenario be trapped inside the endotracheal tube, so that ejecting of the endotracheal tube is obstructed, in which case the procedure must be repeated, or worse, beads can be trapped inside the airways, which could be fatal to the patient and require surgery.

In one embodiment the elongate guide member is a curved pipe. Thus the elongate guide member can be hollow and the string members run inside it.

In an embodiment of the present invention the elongate guide member can be a C-shaped profile or any other profile that guides the string members towards the bendable tip part.

The bendable tip part may advantageously include a tubular cover that accommodates a tip-shaping member to which the first distal string end and the second distal string end are individually attached at respective first string-securing location and second string-securing location. The tip-shaping member may be part of the tip part operating member.

Preferably the elongate guide member can have a curvature following a sector of a circle or have curved sections of different curvatures. E.g. the proximal end part of the elongate guide member may be defined by a first sector of a circle having a large first radius. This proximal end part may extend via an intermediate part defined by a second sector of a circle having a second radius smaller than the first radius, which intermediate part then again may extend into the distal end part of the elongate guide member, which distal end part can have a third radius smaller than the second radius. This design is just given as an example of a suitable curvature design of the elongate guide member and variations are indeed feasible within the scope of the present invention. The preferred curvature of the elongate guide member is the curvature of the endotracheal tube that conforms at least to some extent to the shape of the airway with the patient's head held in the neutral position, a curvature often referred to as the "the Magill Curve". "A Magill Curve" having a radius of curvature of 140 mm±20 mm is found to be about optimum for the average airway, [Tracheal intubation and sore throat: A mechanical explanation; M. Chandler; *Anaesthesia*, 2002, 57, pages 155-161], and suited for the present invention, although various curvatures may work better for various target patients.

The elongate guide member can e.g. be made of aluminium or similar lightweight material. Alternatively the elongate guide member can be made of plastic. The elongate guide member may be form-stable, thus not malleable, although malleable elongate guide members are not excluded within the scope of the present invention.

The tubular cover can e.g. be a soft plastic tube, e.g. of polyethylene or polyethylene vinyl chloride, but any material can be used that allows the tubular cover to yield and allows the tip-shaping member to bend inside the tubular cover without any noticeable increase in the overall diameter of the bendable tip part in response to pulling the string members. If the plastic tube is transparent the operator can even visually follow how the tip-shaping member reacts in response to the operator operating the actuator means thereby providing the operator with a huge advantage of learning and obtaining knowledge of the induced impact on the tip-shaping member in response to such operating of the actuator means, and thus learn how to manipulate the tip-shaping member to assume any desired shape of the bendable tip part. Transparency is however in no way mandatory and same experience of shaping the tip-shaping member can be obtained irrespective of transparency by testing the actuator means.

The first string-securing location and the second string-securing location can be situated lengthwise offset to facilitate bending of the bendable tip part in a more or less distinct S-shape, L-shape or C-shape to assume a shape that can navigate the least obstructed into trachea and be made straight again when desired and needed for retracting the stylet part, e.g. retracting the stylet part from an endotracheal tube that was sheathed on the stylet part prior to the introduction of the endotracheal tube inserting device into trachea and now is left as introduced for ventilation of the patient.

Bending and relaxing the bendable tip part can take place both during inserting this tip part with or without an endotracheal tube sheathed on the stylet part as well as when the endotracheal tube inserting device is retracted.

Emphasis is made that for some patients it may suffice that just one of the first string member and the second string member are operated for the bendable tip part to assume a shape suited for easy passing the endotracheal tube inserting device past the glottis and between the vocal cords.

For difficult airways it is however highly beneficial that the endotracheal tube inserting device of the present invention is provided with the ability to arbitrarily control and customize the shape and curvature of the bendable tip part to a shape specific for the airway anatomy of a certain patient, which significantly eases the insertion of both the stylet part and an endotracheal tube sheathed on the stylet part, as well as the subsequent ejection of the endotracheal tube.

If the first string-securing location and the second string-securing location are radially or laterally offset the bendable tip part can also be moved slightly from side to side.

In one embodiment the first string-securing location and the second string-securing location may be both radially/laterally and lengthwise offset so that both bending the bendable tip part lengthwise and moving a securing location slightly to the side are possible.

The above-mentioned improved and very versatile in situ and real time ability to change the shape of the bendable tip part both outside and inside the patient's body provides an endotracheal tube inserting device that is very fast and convenient to operate, insert correct, and retract without injuring or otherwise harming the patient. The string-securing locations can be moved into a plurality of different positions so that the shape of the bendable tip can be adapted for use with even the most difficult airways thereby making the endotracheal tube inserting device of the present invention not only user-friendly but also patient-friendly.

The tip-shaping member may have a first end secured to the free end of the bendable tip part, and an opposite second end secured to or at the vicinity of the distal stylet end of the elongate hollow guide member so that the tip-shaping member is kept from coiling inside its accommodation in the tubular cover of the bendable tip part, and so that when the first string location and the second string location is tensioned and/or relaxed the first end and the second end of the tip-shaping member are firmly attached at the respective securing points associated with the bendable tip part and/or the stylet part. The handle part incorporates, includes or accommodates the actuator means adapted to operate the tip part operating member to bend the bendable tip part of the stylet part.

In an advantageous embodiment the first string operating member of the actuator means may include a first lever body pivotably arranged about a first pivot axis, which preferably is located inside the handle part, and the second string operating member may include a second lever body pivotably arranged about a second pivot axis, which preferably also is located inside the handle part, said first lever body may have at least one first actuator lever arm extending from the first pivot axis to a first actuator, and an at least one opposite first string operating lever arm to which the first proximal string end is operatively connected to change the position of the first distal string end relative to at least the distal stylet end in response to actuating the first actuator, said second lever body may have at least one second actuator lever arm extending from the second pivot axis to a second actuator, and at least one opposite second string operating lever arm to which the second proximal string end is secured to change the position of the second distal string end relative to at least the distal stylet end in response to actuating the second actuator.

Depressing the first actuator then makes the at least one first actuator lever arm to pivot about the first pivot axis whereby the first string operating lever arm pulls the first proximal string end away from the proximal stylet end inside the housing and bends the bendable tip part by retracting the first distal string end towards the distal stylet end. Similarly, depressing the second actuator makes the at least one second actuator lever arm to pivot about the second pivot axis whereby the second string operating lever arm pulls the second proximal string end away from the proximal stylet end and bends the bendable tip part by retracting the second distal string end towards the distal stylet end inside the housing. A first fulcrum is defined at the first pivot axis and a second fulcrum is defined at the second pivot axis.

The at least one first actuator lever arm extends as the effort arm and the first string operating lever arm extends as the resistance arm on opposite sides of the first fulcrum. Upon application of a force to the first actuator at the free end of the first actuator lever arm the first string operating lever arm pivots about the first pivot axis of the first fulcrum whereby the first string member is pulled backwards away from the proximal stylet end thereby also pulling the first distal string end closer to the proximal stylet end. When the force on the first actuator is relieved the first lever body returns to its starting position, but can be in any pivoted position between the starting position and the ultimate pivoted position depending amongst other on an adjustment of the level of force applied to the first actuator.

Similarly the at least one second actuator lever arm extends as the effort arm and the second string operating lever arm extends as the resistance arm on opposite sides of the second fulcrum. Upon application of a force to the second actuator at the free end of the second actuator lever arm the second string operating lever arm pivots about the second pivot axis of the second fulcrum whereby the second string member is pulled backwards away from the proximal stylet end thereby also pulling the second distal string end closer to the proximal stylet end. When the force on the second actuator is relieved the second lever body returns to its starting position, but can be in any pivoted position between the starting position and the ultimate pivoted position depending on an adjustment of the level of force applied to the second actuator.

In an embodiment wherein the second string-securing location is different from the first string-securing location, such as lengthwise offset, application of various levels of force to one or both of the first actuator and the second actuator of the actuator means will induce bending of the bendable tip part in response to operating the first actuator and the second actuator.

The handle part may comprise the housing for accommodating at least the first lever body and the second lever body, which housing has a first opening for making the first actuator accessible to pivot the first lever body from outside the housing, and a second opening for making the second actuator accessible to pivot the second lever body from outside the housing. The housing can expediently also accommodate at least a part of the tube ejecting mechanism and be open distally to allow the moveable third rack part and the wedge part with the tube connector to move along the length of the handle part.

The pivoting of the first lever body and the second lever body may reach their respective ultimate position when hitting a stop provided at the handle part, e.g. inside the housing of the handle part, optionally simply hitting the inside of the housing, or any other structural component provided for that purpose. The first actuator and the second actuator are both accessible for the operator via such a housing, e.g. via the respective first opening and the second opening in the housing above the respective pivot axes when the handle part is grasped by a hand in the operation position. Preferably the first actuator and the second actuator protrude from the respective first opening and second opening.

Preferably the first lever body may be pivotably suspended to move a first string-securing member of the housing, and the second lever body may be pivotably suspended to move a second string-securing member of the housing, and wherein the first string-securing member may be arranged spaced from the first pivot axis to allow the first lever body to pivot and pull at the first string member. Similarly the second string-securing member may be arranged spaced from the second pivot axis to allow the second lever body to pivot and pull at the second string member. A string-securing member can be any kind of structure that can be secured to the corresponding lever body to pivot said lever body about its pivot axis. An example of a string-securing member includes but are not limited to a pin fitting into a cavity provided at the free end of a string operating lever arm opposite the associated pivot axis or being hooked to this location, and where the string member is secured to the pin e.g. by being wound on the pin to be firmly secured.

Other examples are other female securing means provided in or at the free end of a string operating lever arm, e.g. a hole, an eye or a ring for tying the string member at the proximal string end.

Accordingly in one embodiment the endotracheal tube inserting device may further include that
- a suspension body are arranged inside the housing and being configured with the first pivot axis and the second pivot axis for pivotally suspending the first lever body and the second lever body, respectively,
- that the first proximal string end is operatively connected to the end of the first string operating lever arm opposite the first pivot axis to displace the first string member along the elongate hollow member,
- that the second proximal string end is operatively connected to the end of the second string operating lever arm opposite the second pivot axis to displace the second string member along the elongate hollow member,
- and wherein
- the first string-securing member and the second string-securing member are arranged below the suspension body opposite the respective first actuator and second actuator.

Because an actuator is located remote from a string-securing member this design and suspension of lever bodies provide for maximum force application at minimum depression of the corresponding actuator. The first lever body and the second lever body are operated individually by spaced apart respective first and second actuators, whereby, the first lever body can be operated and pivoted unobstructed of the pivoting of the second lever body when this second lever body is operated.

In an embodiment of the present invention the first lever body can be a first bifurcated lever body having opposite first legs joined by the first actuator, which opposite first legs extends from the first actuator into opposite first actuator lever arms that extends further via the first pivot axis into opposite first string operating lever arms, and the second lever body can be a second bifurcated lever body having opposite second legs joined by the second actuator, which opposite second legs extends from the second actuator into opposite second actuator lever arms that extends further via the second pivot axis into opposite second string operating lever arms.

The first bifurcated lever body thereby defines, in-between the opposite first legs, a first gap for receiving a first part of the suspension body and for pivotably suspending the first lever body to the first pivot axis. A force on the first actuator can then pivot the first lever body between its ultimate depressed position, wherein the first actuator, that bridges the opposite first legs, hits on the suspension body to stop further pivoting, and a relaxed start position, wherein there is a gap between the bridging first actuator and the suspension body to allow depression of the first actuator.

Similarly, the second bifurcated lever body thereby defines, in-between the opposite second legs, a second gap for receiving a second part of the suspension body and for pivotably suspending the second lever body to the second pivot axis. A force on the second actuator can then pivot the second lever body between its ultimate depressed position, wherein the second actuator, that bridges the opposite second legs, hits on the suspension body to stop further pivoting, and a relaxed start position, wherein there is a gap between the bridging second actuator and the suspension body to allow depression of the second actuator.

The ultimate depressed positions of an actuator can also be when the legs hits a component of the housing or the housing itself, in which cases the bridging part of an actuator may even not be able to move into contact with the suspension body.

The first part of the suspension body may e.g. be the part of the suspension body closest to the proximal stylet end and the second part of the suspension body may e.g. be the part of the suspension body farthest from the proximal stylet end.

In an alternative embodiment of the present invention the first string-operating member and the second string-operating member can be hinged to an tubular exterior wall of a curved tubular body that defines a housing to pivot between a relaxed position wherein any of the first string-operating member and the second string-operating member protrude spaced from the tubular exterior wall and an actuated position wherein the first string-operating member and the second string-operating member are closer to the tubular exterior wall than in the relaxed position. The tubular body is convenient to grasp to operate the first string-operating member and the second string-operating member, which first string-operating member and the second string-operating member expediently may be arranged adjacent each other to be operated by adjacent fingers of the hand used to grasp on the tubular body that is part of the handle part.

The first string-operating member and the second string-operating member can for example simply be pivotable flaps, such as a pivotable first flap to which the first proximal string end of the first string member is secured, and a pivotable second flap to which the second proximal string end of the second string member is secured.

Said flaps may preferably be curved flaps having same center of curvature as a cross-section as the exterior tubular wall, however other curvatures are within the scope of the present invention. The curved flaps can for example be provided by a cross-sectional segment of the exterior tubular wall, in which embodiment the curved flaps extends pivotably by its attachment of a single flap edge at the joining to the exterior tubular wall, the edge being the hinge, as an integral part of said tubular wall. The hinge may have e.g. a weakening, indent of similar feature that facilitates and promotes the pivoting of the flap. The flaps can also be hinged to the exterior tubular wall by means of another kind of hinge, such as a leaf hinge. Other kinds of flaps, curved or straight, can be secured to the exterior tubular wall as separate objects. In the relaxed condition of the string members, said string members can either pass into the interior of the tubular body via a respective string hole made for this entry purpose, or span the somewhat larger hole left when the flaps are excised form the exterior tubular wall and run outside the exterior tubular wall before they enter the lumen of the tubular body at the vicinity of the proximal stylet end. So the string members can be guided on the outside of tubular exterior wall and be secured to the respective pivotable flaps.

In yet an embodiment of string-operating members the first string-operating member and the second string-operating member may be constituted of opposite lever arms of a rocker having its fulcrum at the tubular exterior wall and the string members respectively secured to said lever arms. Combinations of the afore-mentioned features amongst and within the embodiments are within the scope of the present invention. In particular the invention foresees the combination of different kinds of tip-shaping members with different kinds of string-operating members, different hinges of string-operating members and/or different pivots and pivoting of flaps and actuators, and different extensions and moving of the string members, including how the string members extends in relation to the handle part, and in particular in relation to the tubular body.

Irrespective of the string-operating members are actuator button, flaps, or rockers they preferably are connected to the respective string members in a manner that makes the string-operating members automatically jump back into a relaxed position once any force applied to said string-operating members are relieved. Thus the string-operating members may have an inherent springiness provided, amongst others, by the way the string-operating members are connected to the housing combined with the length and locations of the string members, but the provision of a spring for promoting return to its relaxed condition of a string-operating member that has been subjected to a force is not excluded by the present invention.

The curvature of the endotracheal tube provided on the stylet part may advantageously be of the kind that conforms to or has the same curvature as the curvature of the elongate hollow guide member of the stylet part, thereby also conforming to the shape of the airways as in when the patient's head is held in the neutral position, as described above.

The endotracheal tube suited for the present endotracheal tube inserting device may have a standardized airway connector of internal diameters of e.g. 15 mm and 22 mm, thus conforming to ISO standard no. 5356-1, so that it by way of its standardization can be connected to all other airway equipment. Situations with non-compatibility between coupling of airway equipment and endotracheal tube and urgent need for special adaptors to establish ventilation are thus prevented.

A conical tube connector may be arranged on the stylet part at the proximal stylet end to mate with the airway connector of the endotracheal tube, so that the endotracheal tube stay put and correct on the stylet part when the endotracheal tube inserting device is moved into the airways, initially by operating the ejecting mechanism. The conical shape of the tube connector allows the tube connector to fit together with airway connectors of different diameter. A large diameter tube connector is just moved closer upwards towards the handle part to couple around the conical tube connector than needed for a smaller diameter tube connector.

There are different lengths of endotracheal tubes and therefore the position of the conical tube connector on the stylet part may in some embodiments be made adjustable, e.g. by allowing the conical tube connector to slide on the elongate hollow guide member.

The endotracheal tube may or may not have a cuff which can be inflated to seal the lungs against the liquid secretions present in the upper airways, and seals distally to allow ventilation of the patient under controlled pressure and defined gas mixture. Use of an endotracheal tube with inflatable cuff is almost always used for adults whereas most pediatric tubes are uncuffed.

The endotracheal tube-inserting device of the present invention may be used with both an uncuffed endotracheal tube and a cuffed endotracheal tube. The size of the appropriate endotracheal tube depends on e.g. the patient's age and airway anatomy size. If a cuffed endotracheal tube is used the internal diameter in millimeters is typically calculated as 4+(Age/4). In case of a cuffed endotracheal tube the size of its internal diameter is typically calculated as 3.5+(Age/4). Such endotracheal tubes may however have standard airway connectors that allow the same endotracheal tube-inserting device to be used with several different endotracheal tubes.

Operation of the endotracheal tube inserting device according to the present invention is done with one and the same hand, without the hand needs to be taken off the handle part. Thus the endotracheal tube inserting device can easily be held steady and be operated without huge motions of the hand holding and operating it, and without the need to change the position of the hand on the handle part at any time during the endotracheal procedure.

The pivoting effect conferred to a lever body or to a pawl member by the force applied to an actuator can be utilized optimum. Optimum torques can be achieved at a limited space and without the operator needs to apply huge force and move his hand around on the handle part thus preserving a convenient size and shape of the handle part.

The housing can e.g. be a curved tubular body having a circumferential exterior wall that encases several of the components of the endotracheal tube-inserting device needed for its operation. The tubular body offers a good grip for holding on to the endotracheal tube-inserting device during it.

All components of the tip part operating member can be hidden inside an appropriate respective receptacle, whether it being a housing of the handle part, the tubular cover or the elongate hollow guide member, which makes the overall design very hygienic and simple to sterilize in case of being intended for reuse. The suspension body may function to suspend the lever bodies spaced apart from each other so that they can pivot smoothly without hitting each other.

So in the embodiment with a lever body, when a lever body is pivoted by depressing the corresponding actuator the end of the corresponding string operating lever arm, which is connected to the string-securing member, can pull or relax a string member without the string members get entangled, jam, or the lever bodies hit on each other.

The string-operating members may be adapted to provide a tactile feed-back to the operator in response to applying a force on and/or relieving said force from the string-operating members.

The invention will be explained in greater details below with reference to the drawing, which illustrates exemplary embodiments to disclose further advantageous and technical features and effects of the present invention.

Figure 2:
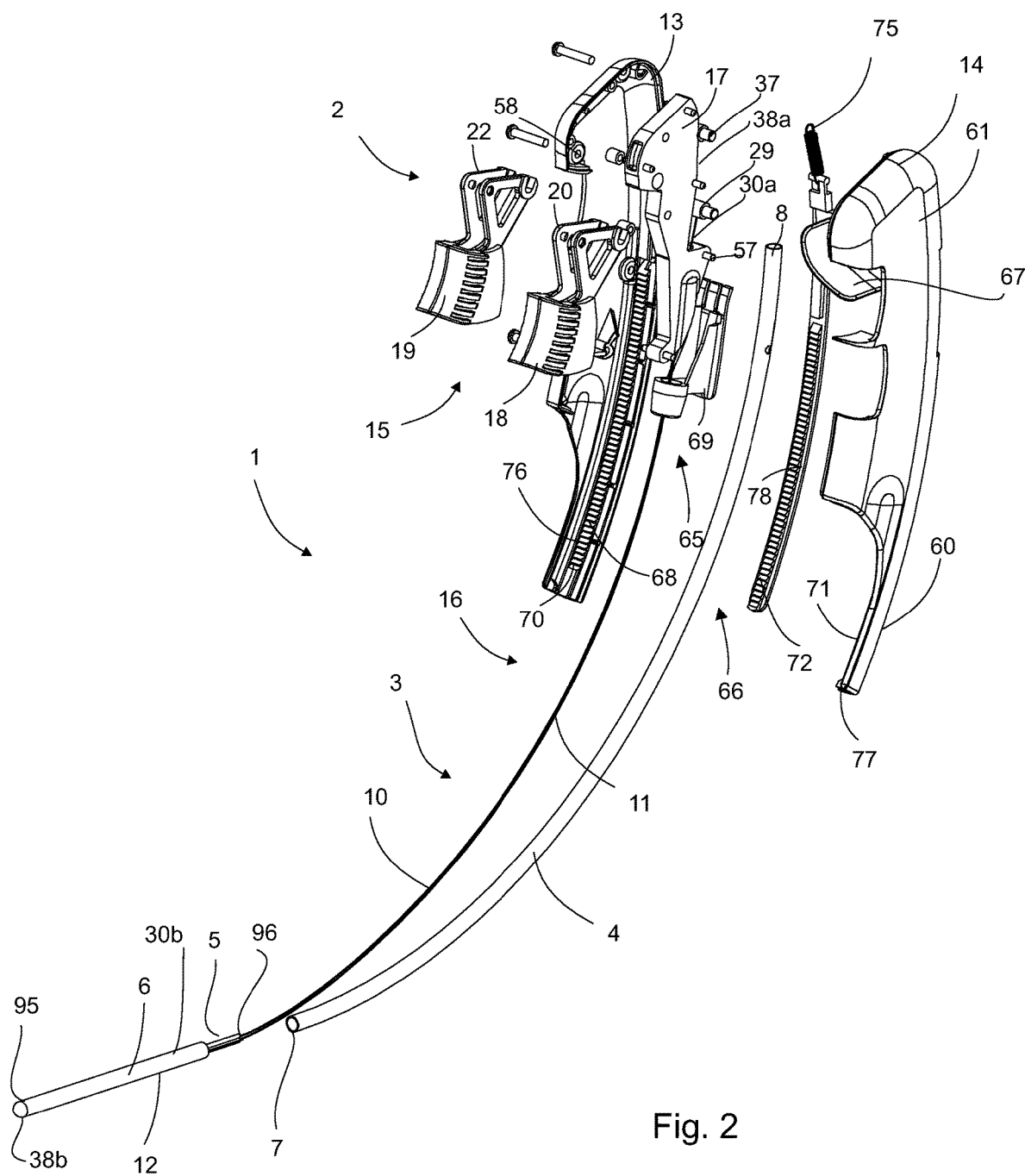
Figure 3:
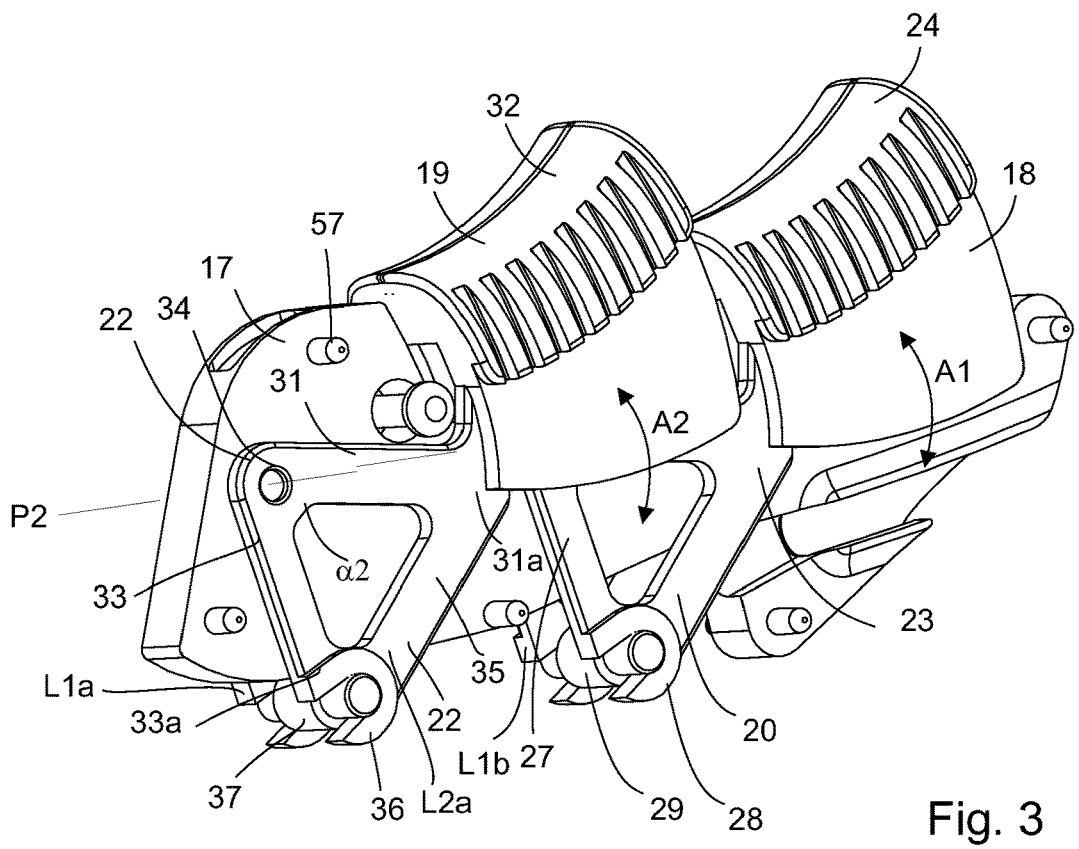
Figure 4:
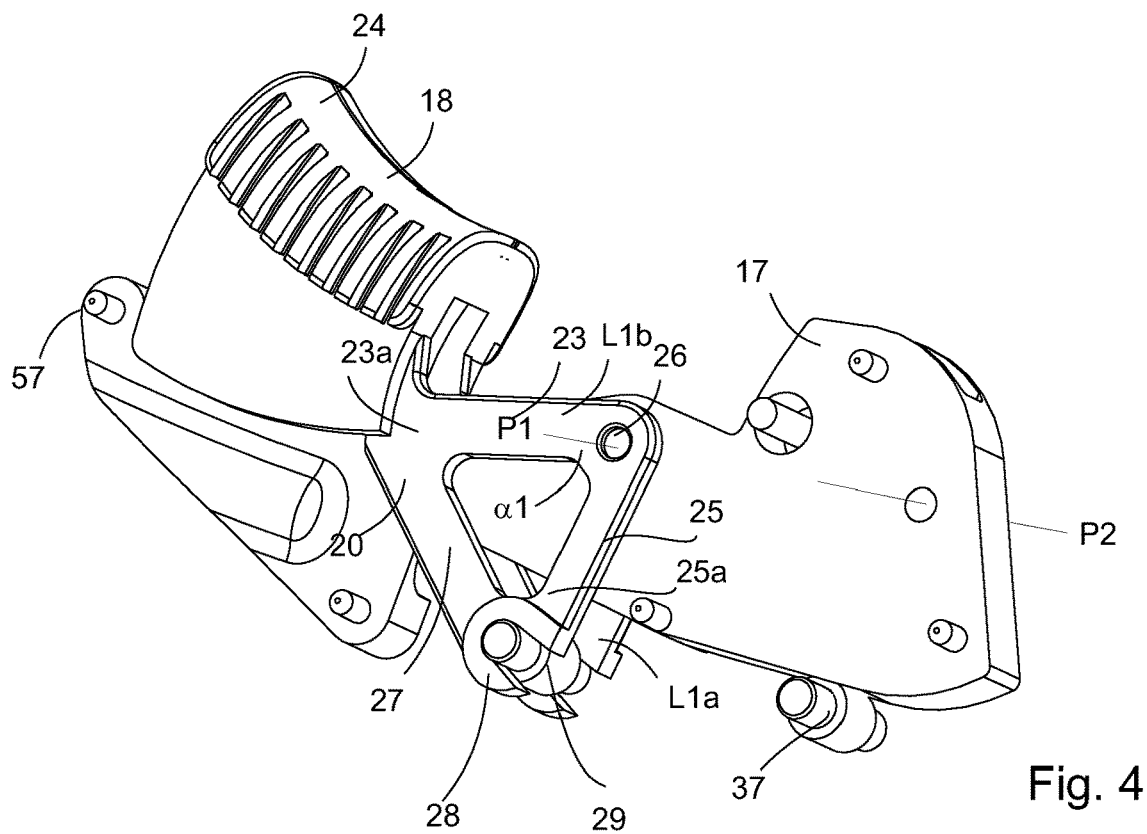
Figure 5:
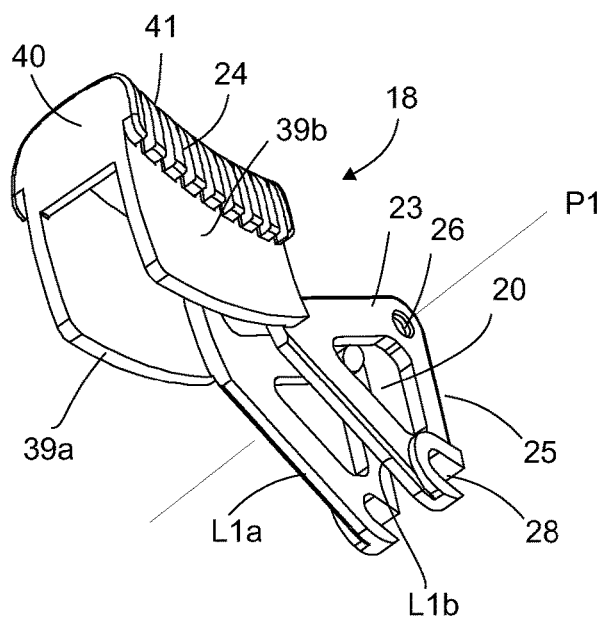
Figure 13:
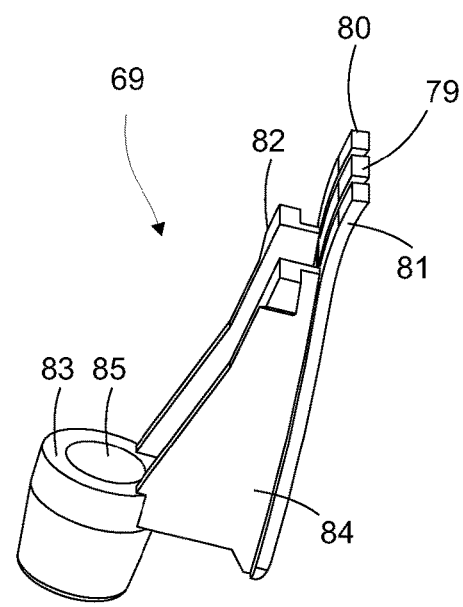
Figure 6:
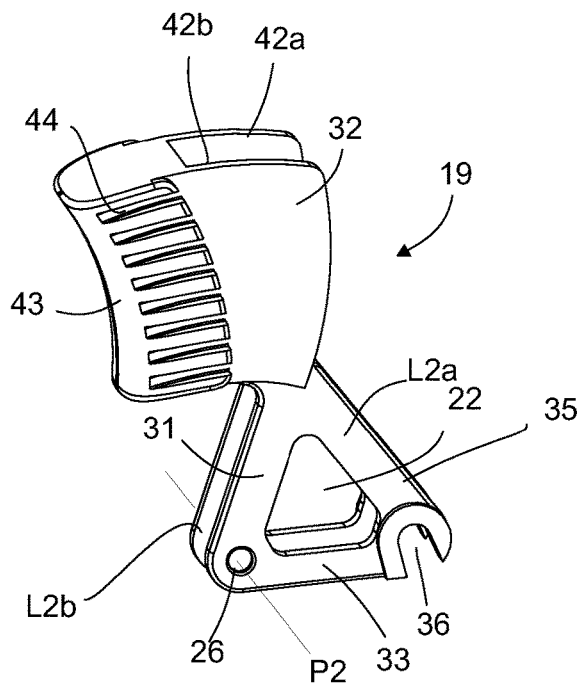
Figure 7:
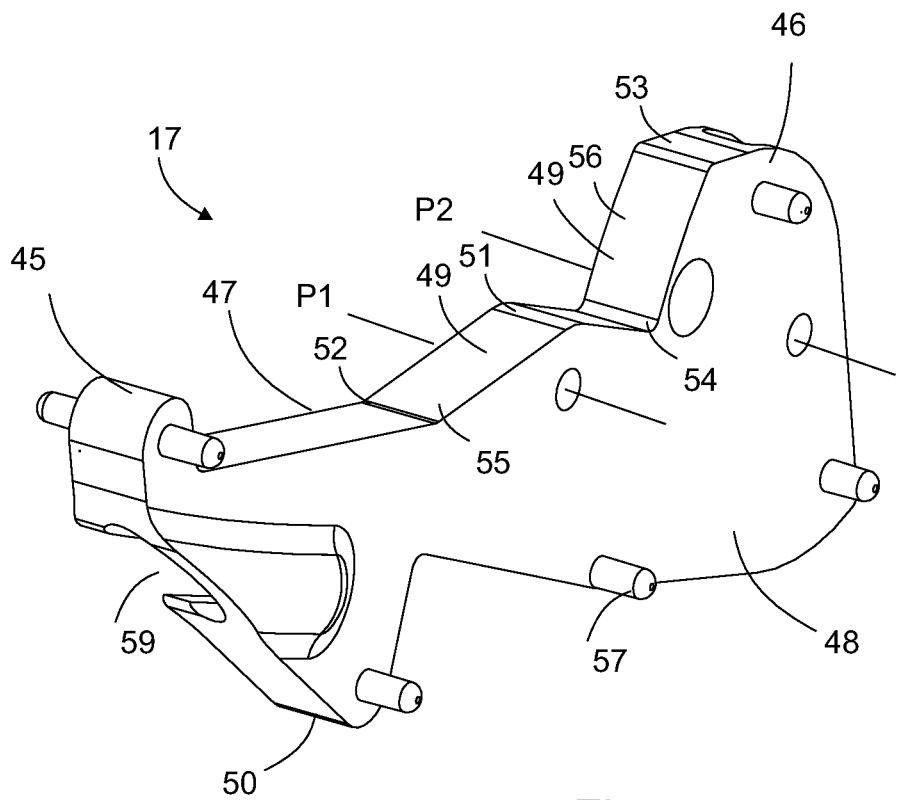
Figure 8:
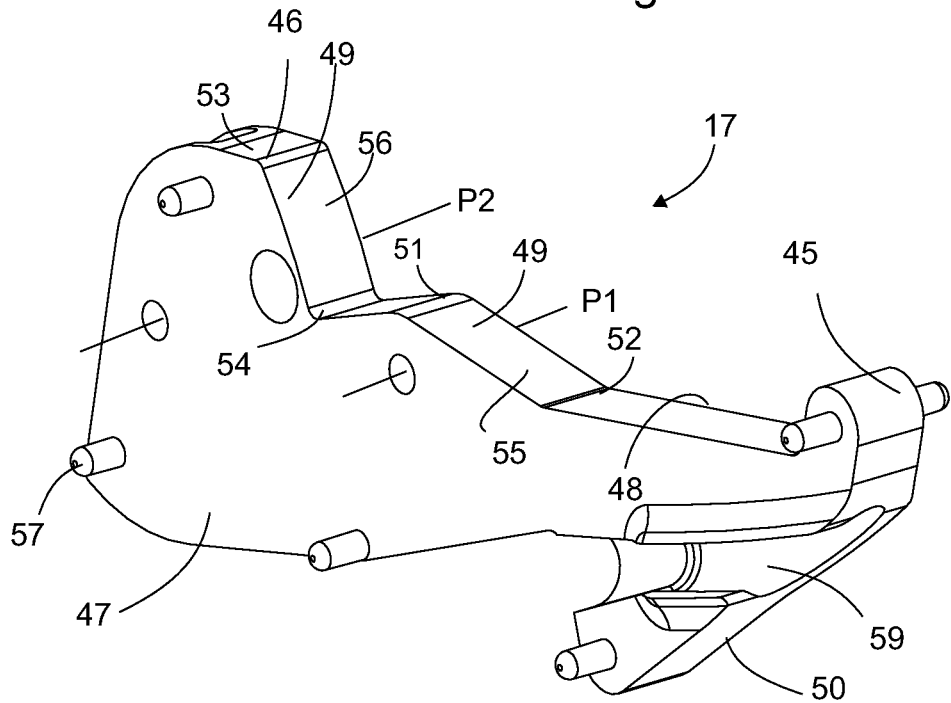
Figure 12:
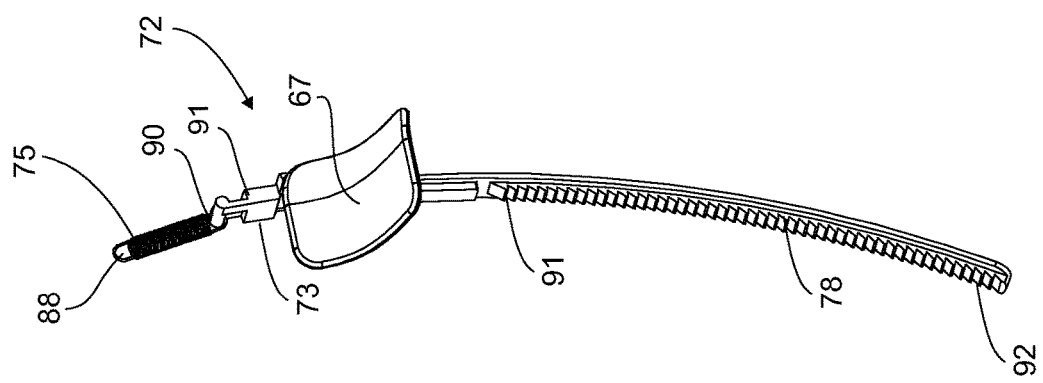
Figure 11:
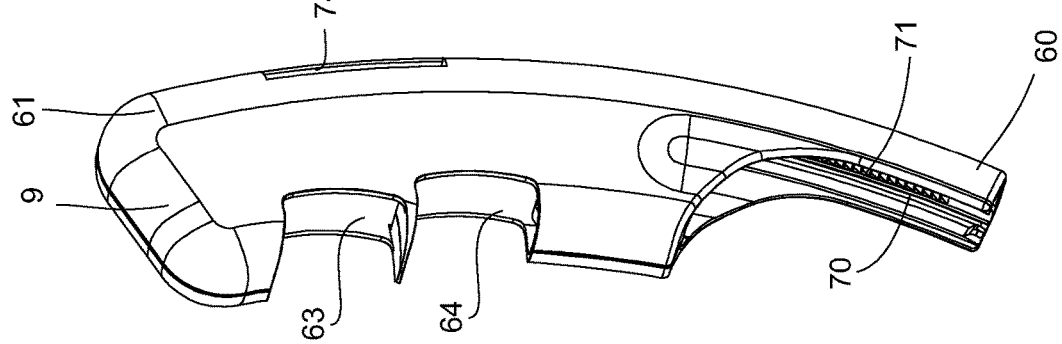
Figure 10:
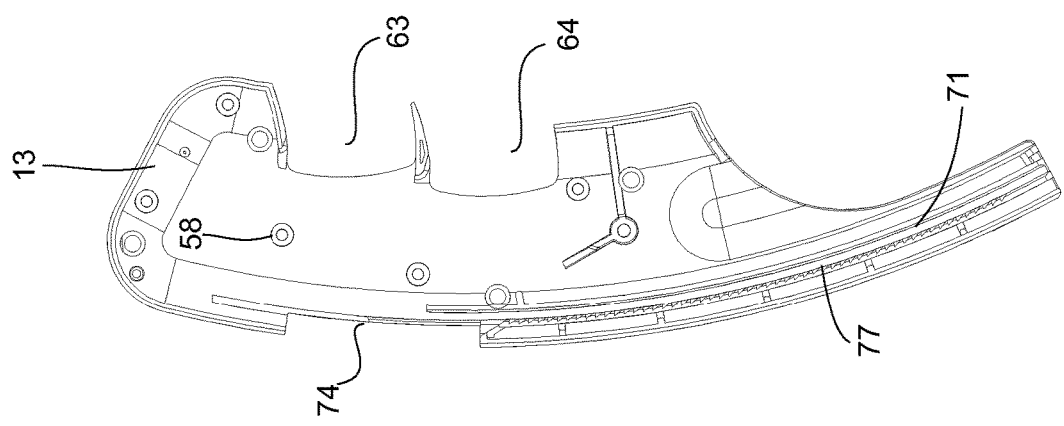
Figure 9:
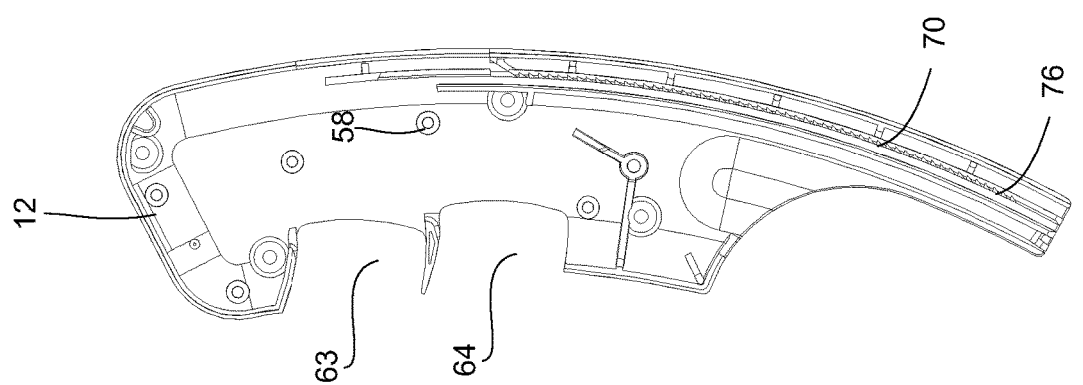
Figure 14:
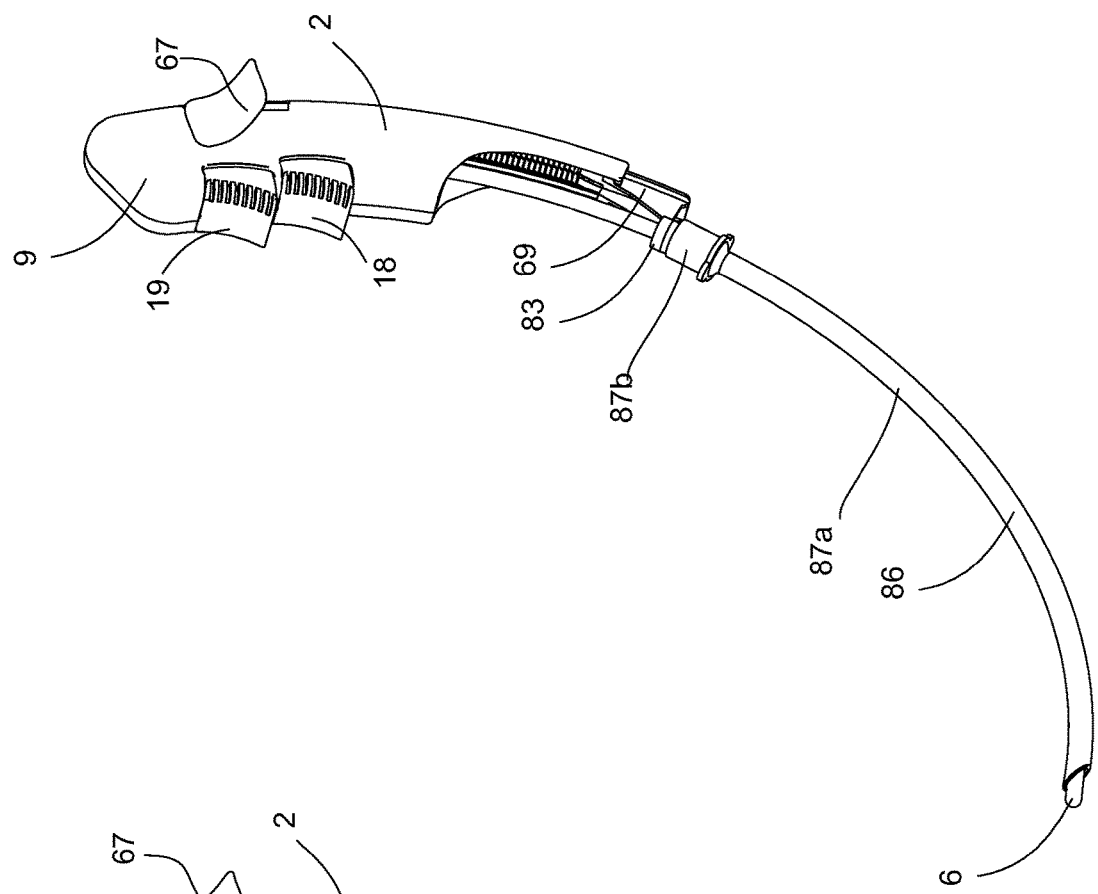
Figure 15:
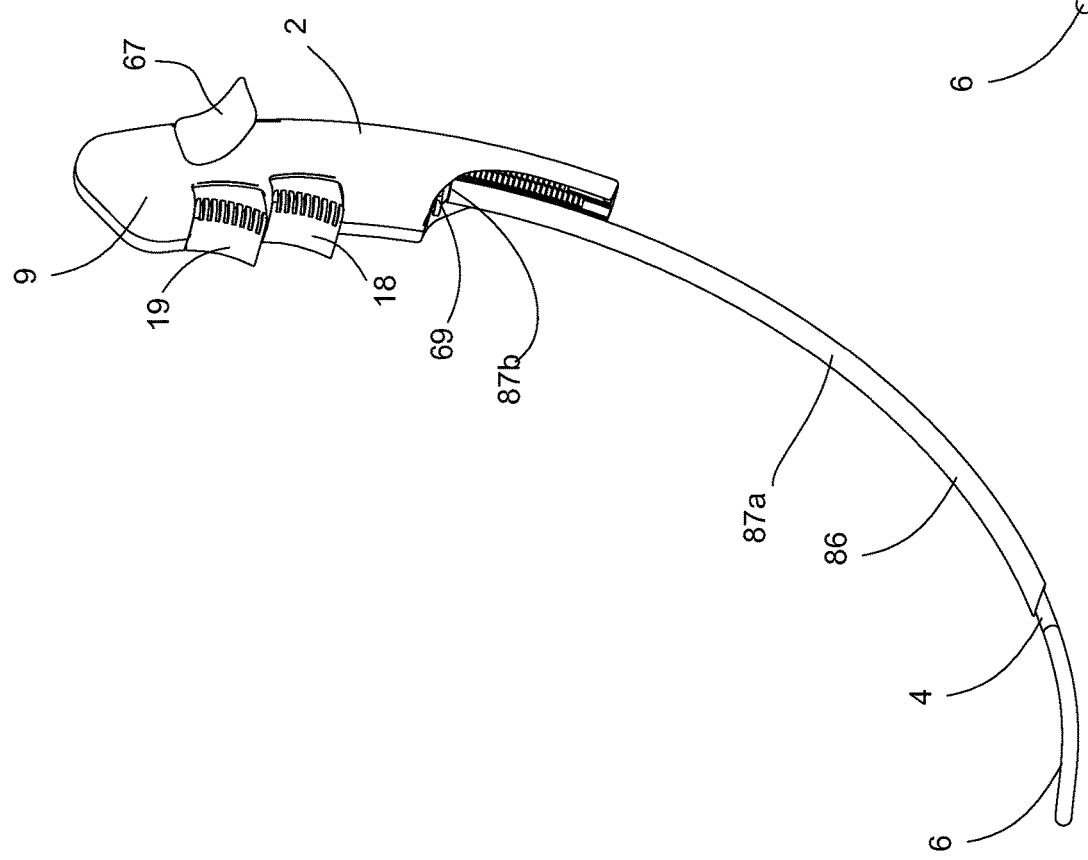
Figure 19:
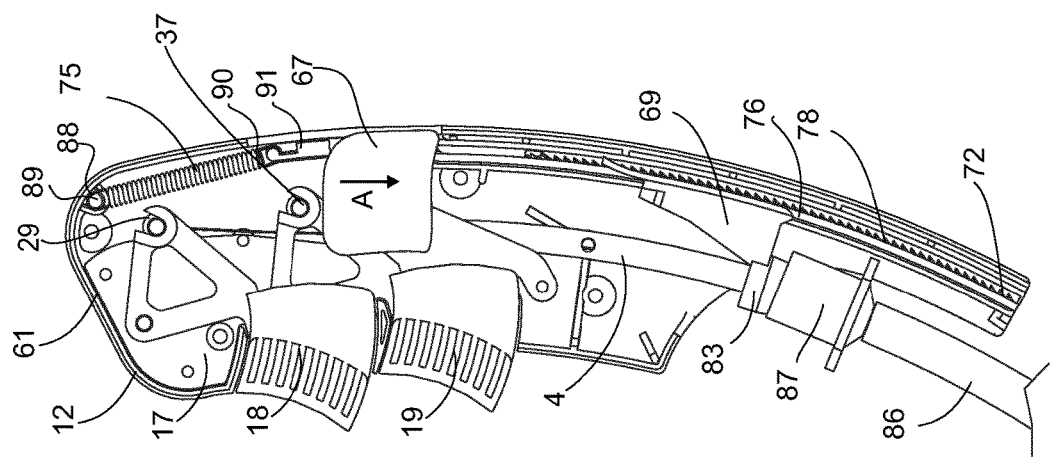
Figure 18:
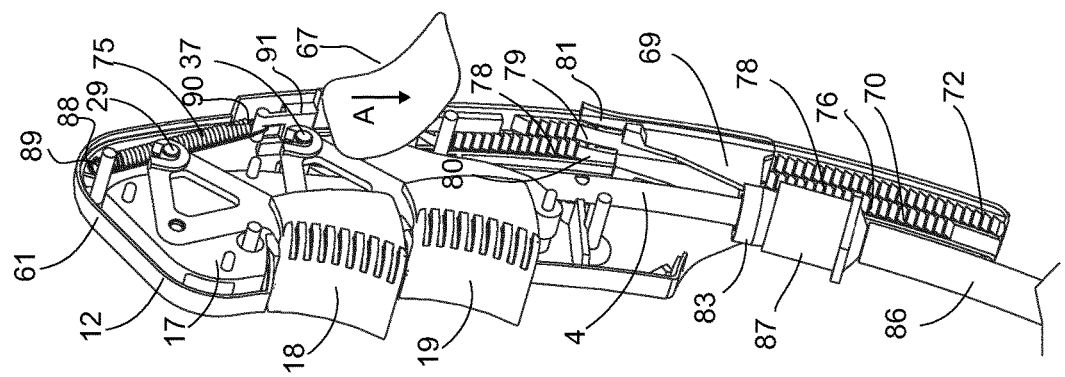
Figure 17:
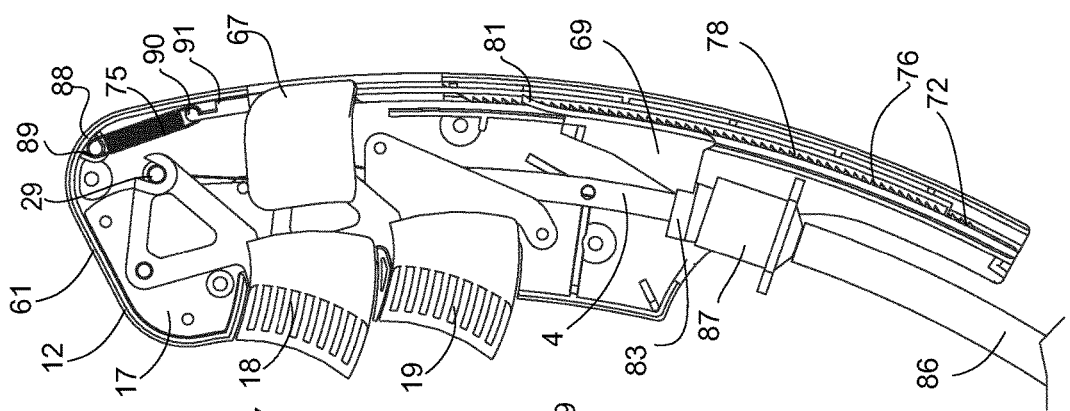
Figure 16:
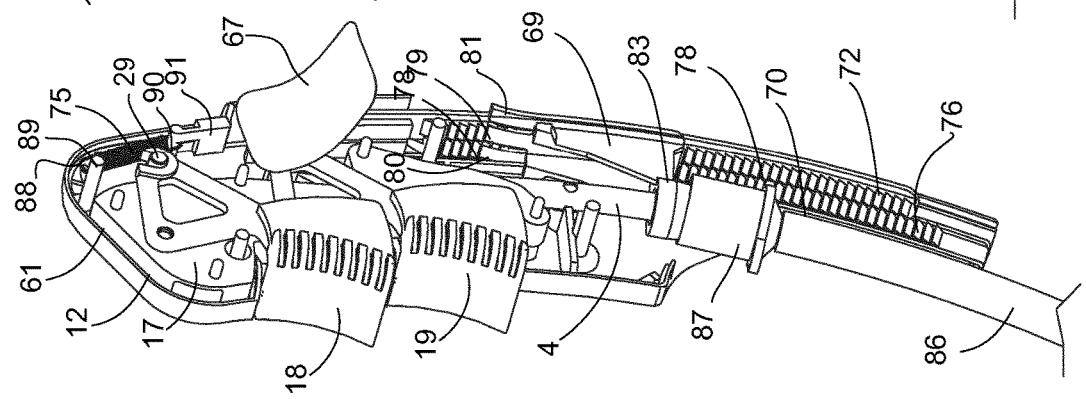
Figure 20:
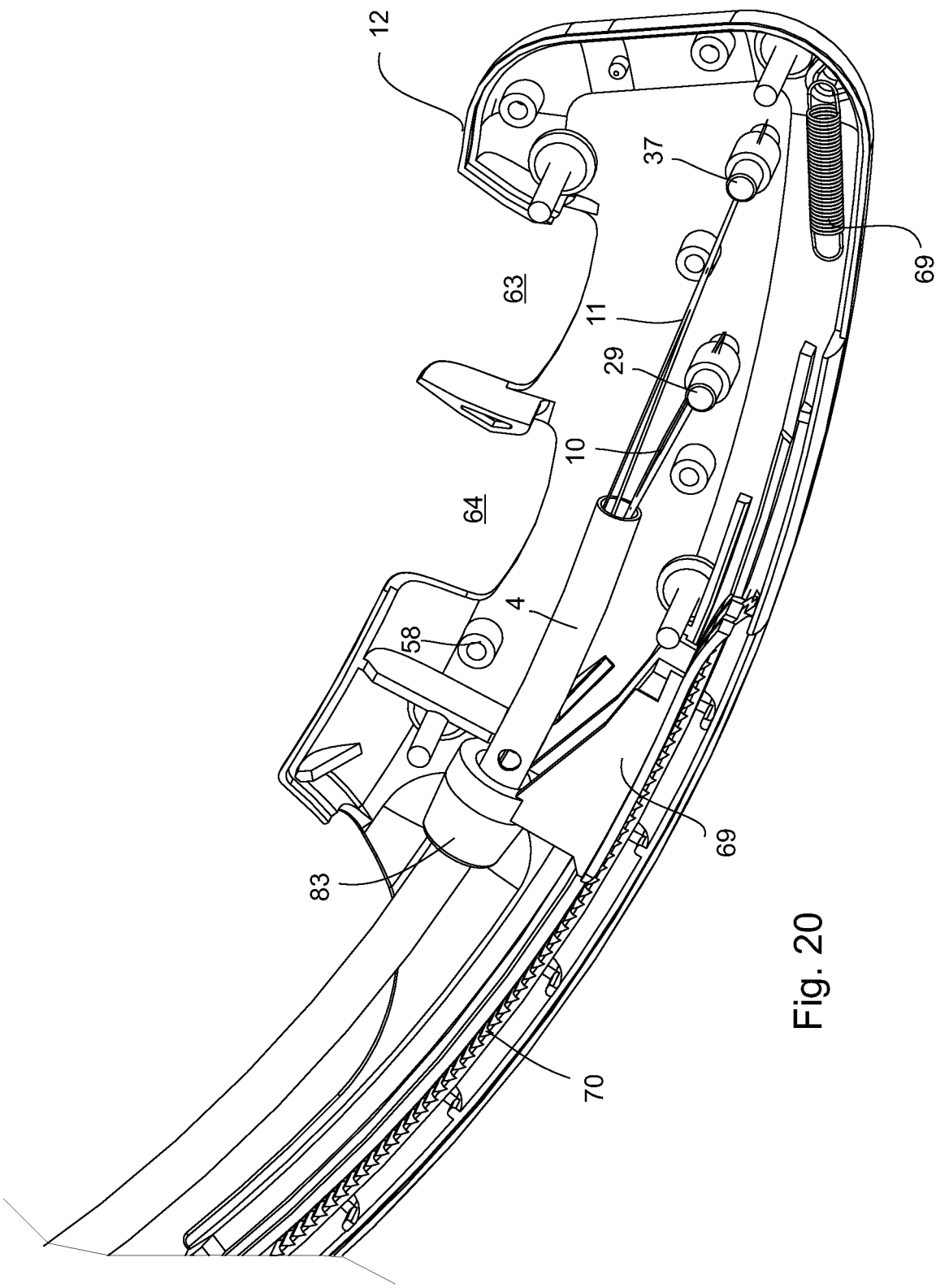
Figure 29:
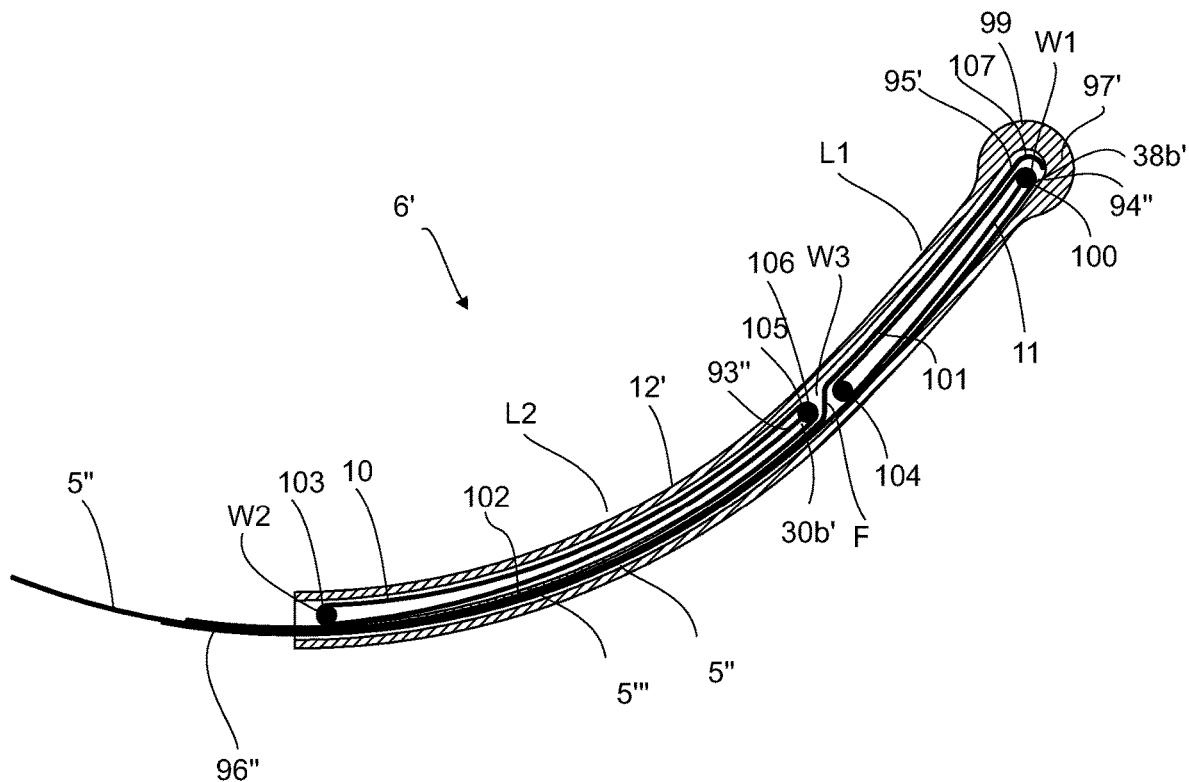
Figure 30:
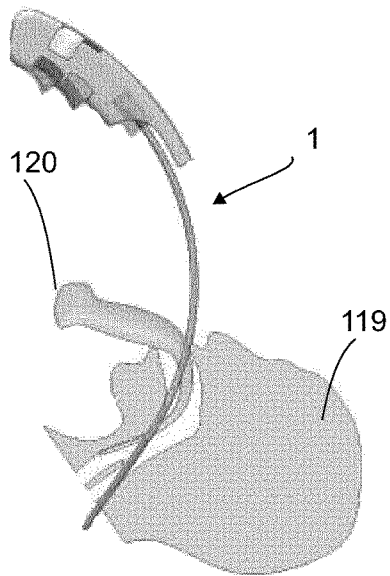
Figure 31:
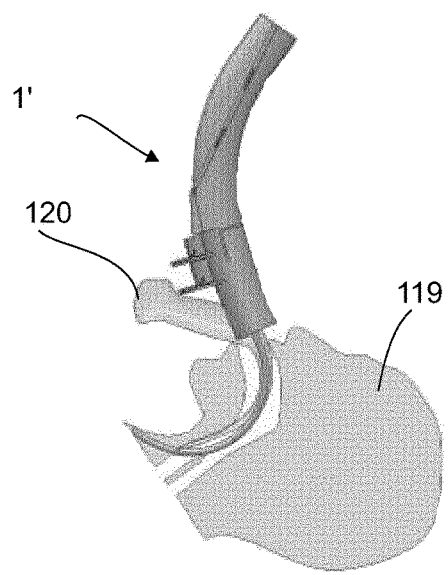
Figures 32A, 32B:
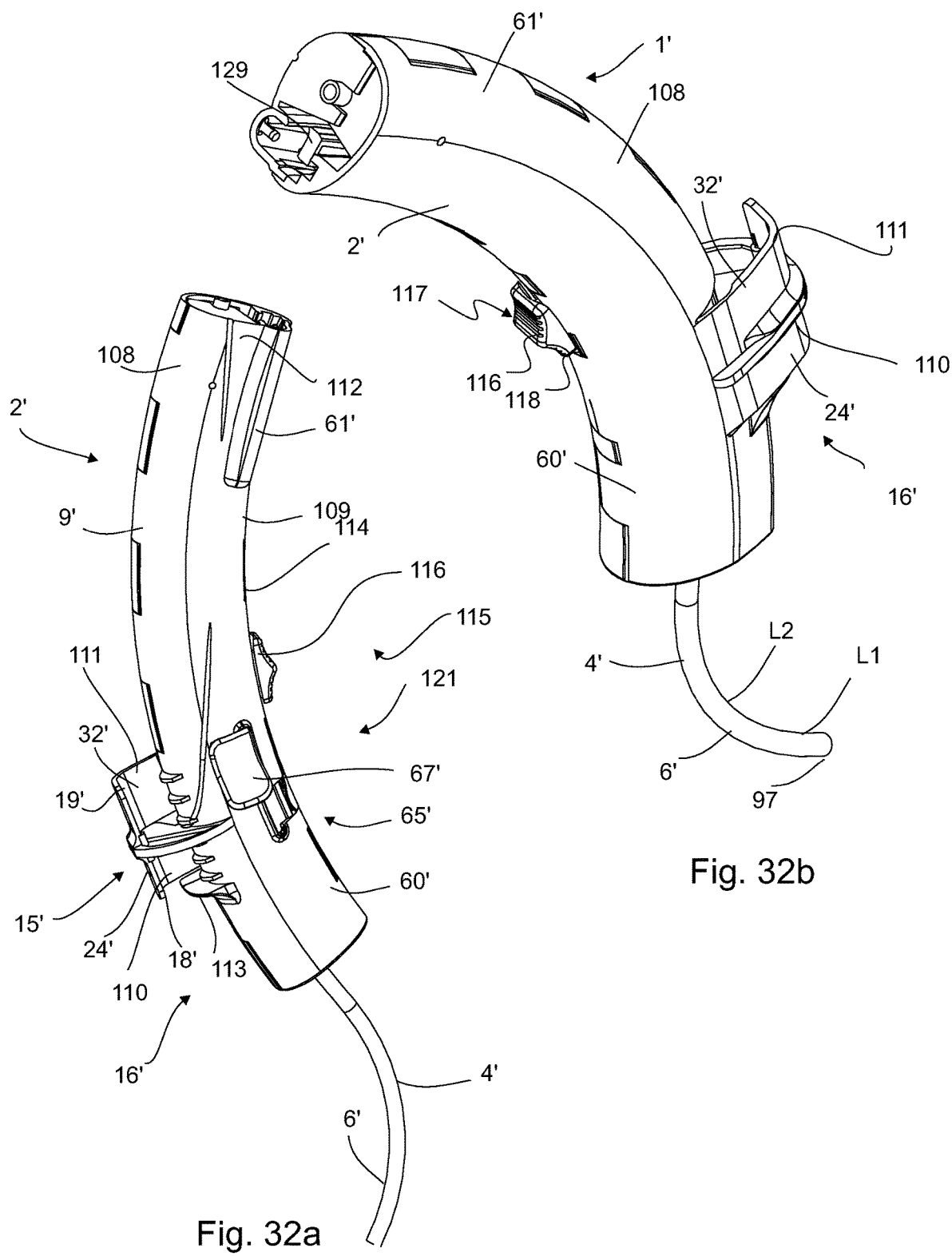
Figure 34:
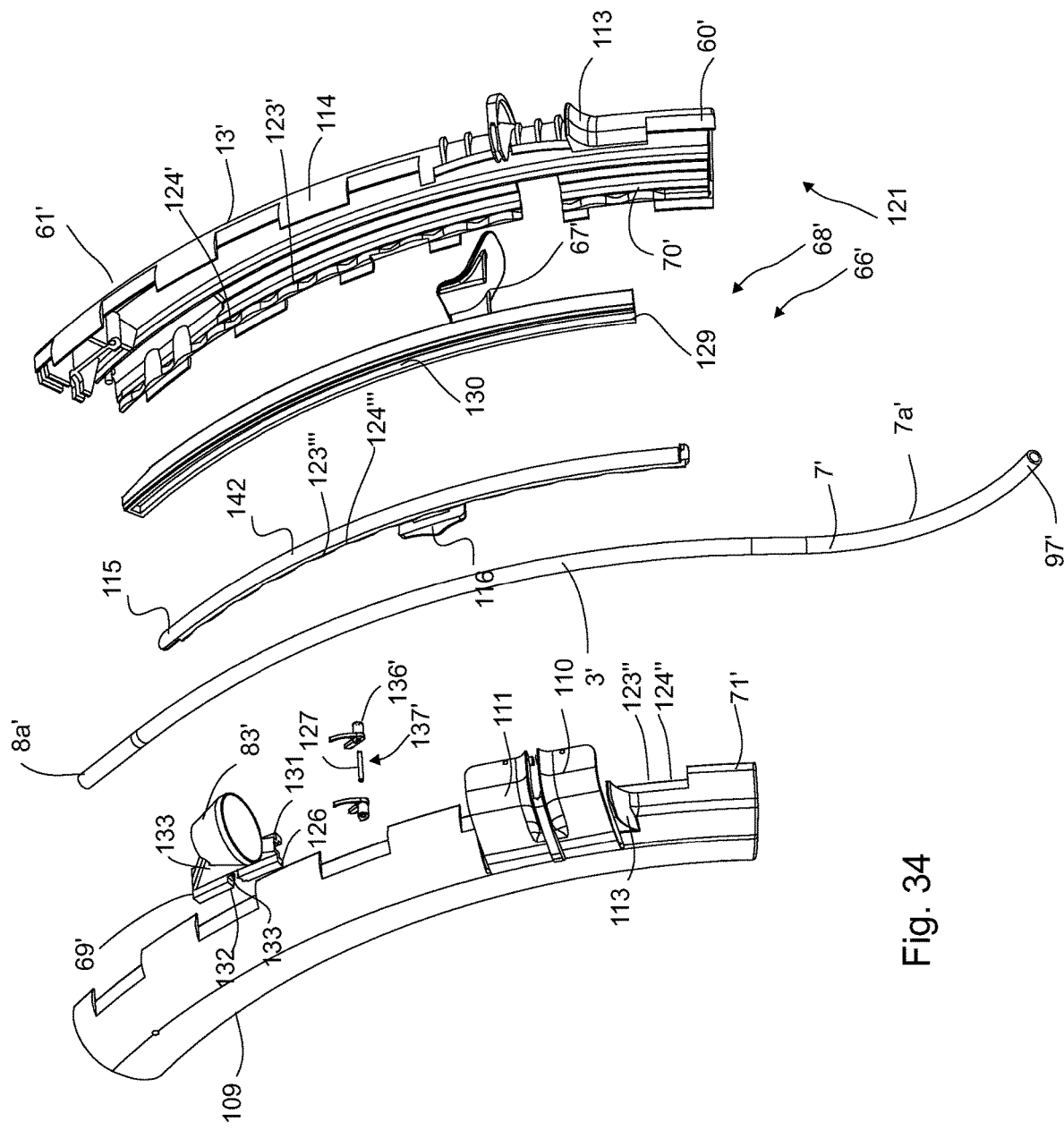
Figure 35:
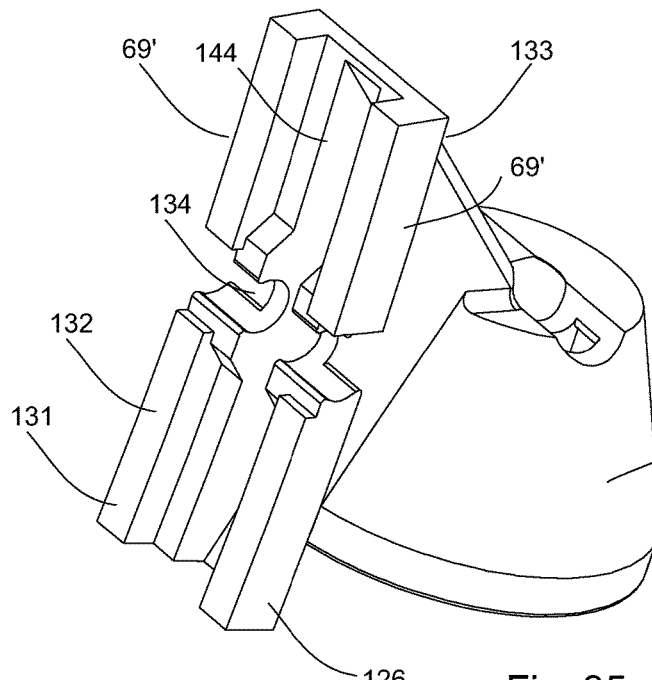
Figure 37:
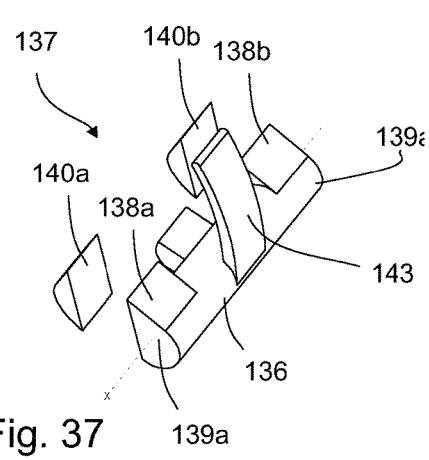
Figure 36:
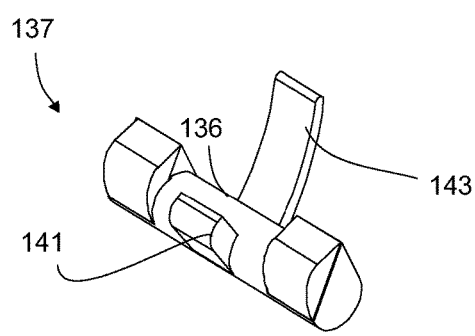
Figure 38:
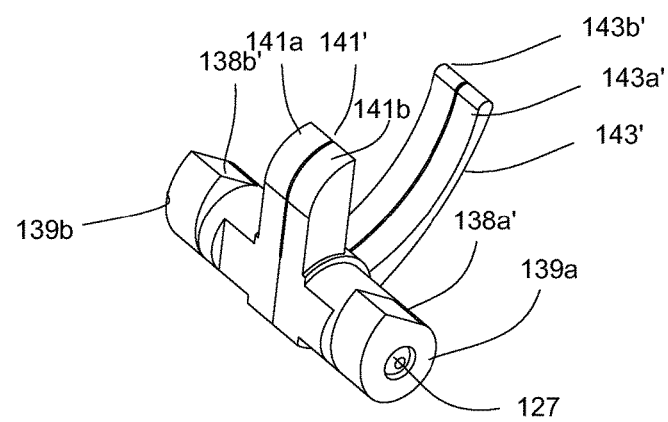
Figure 40:
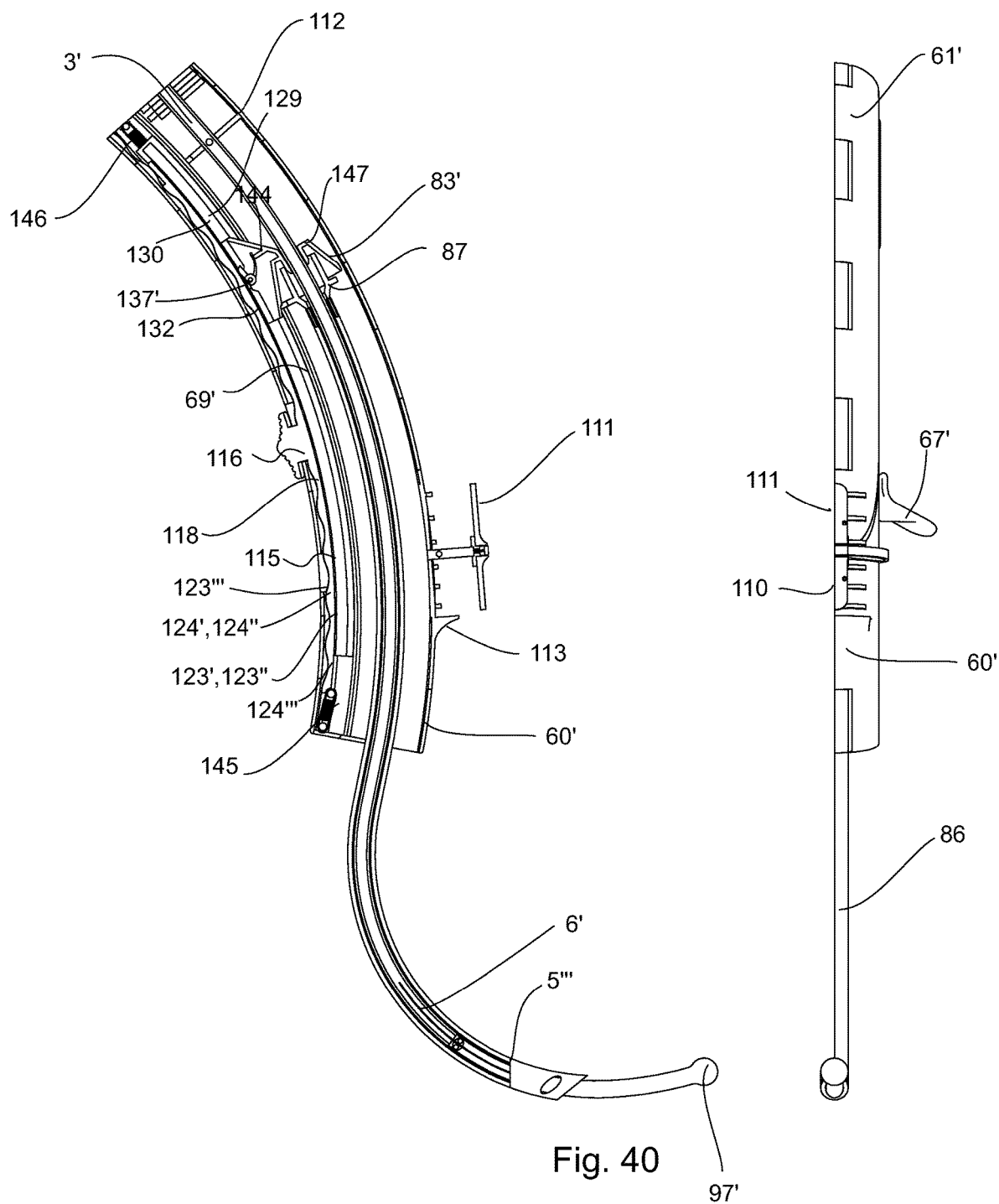
Figure 41:
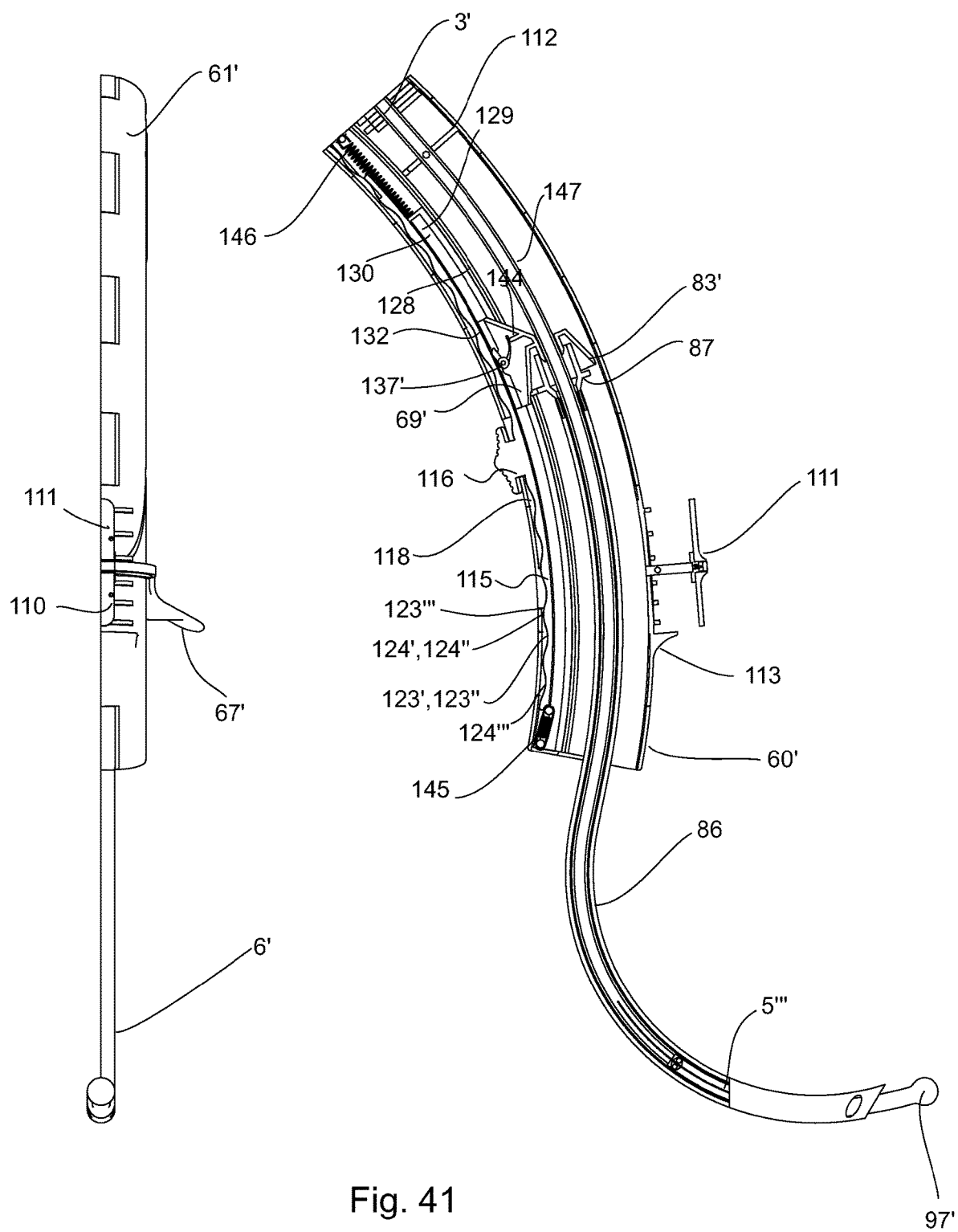
Figure 43A:
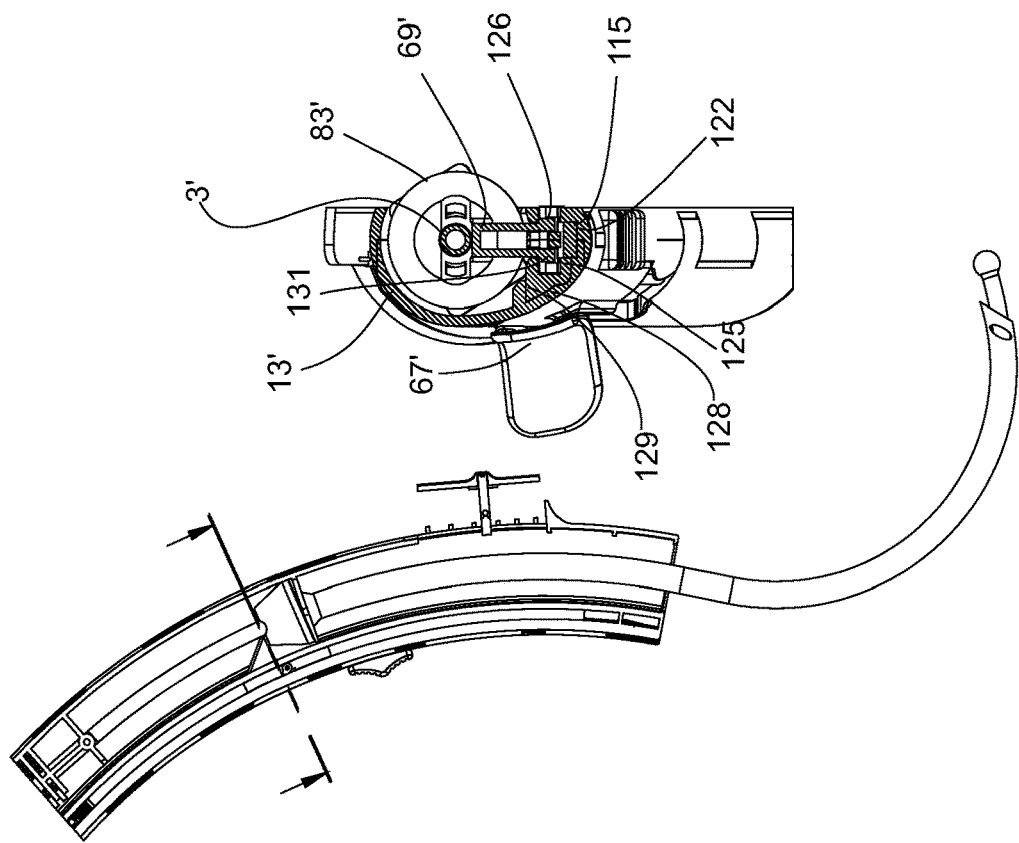
Figure 43B:
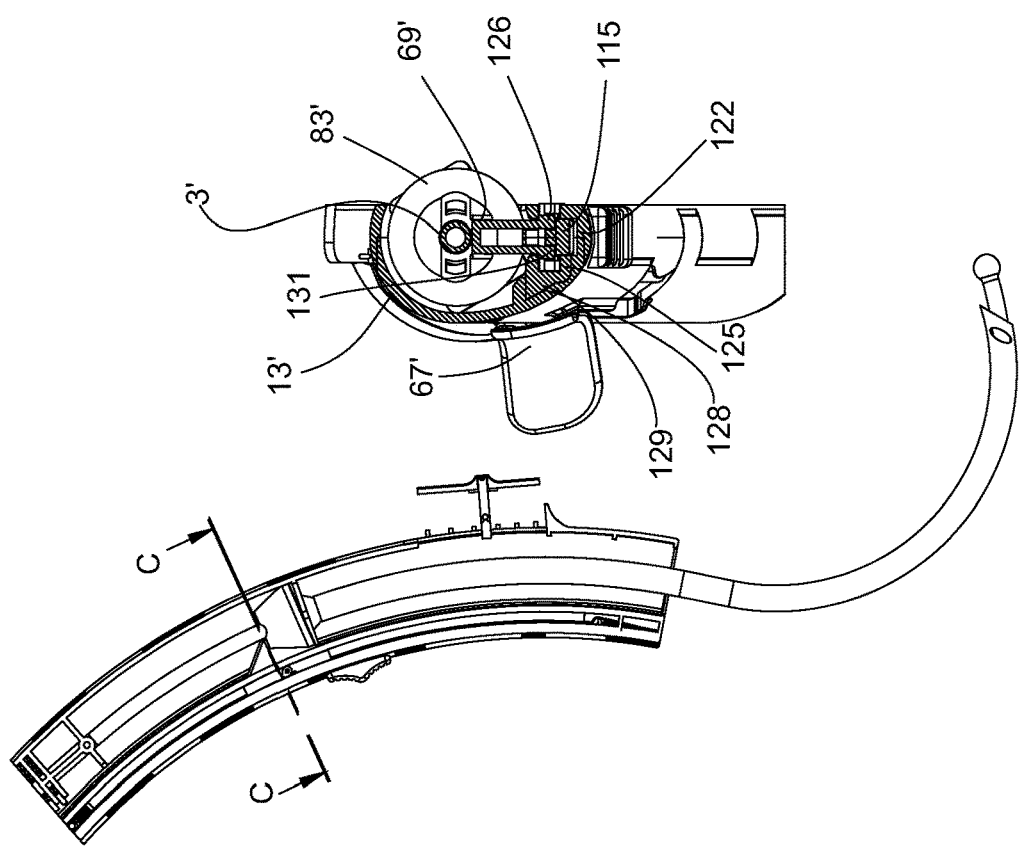
Figure 44A:
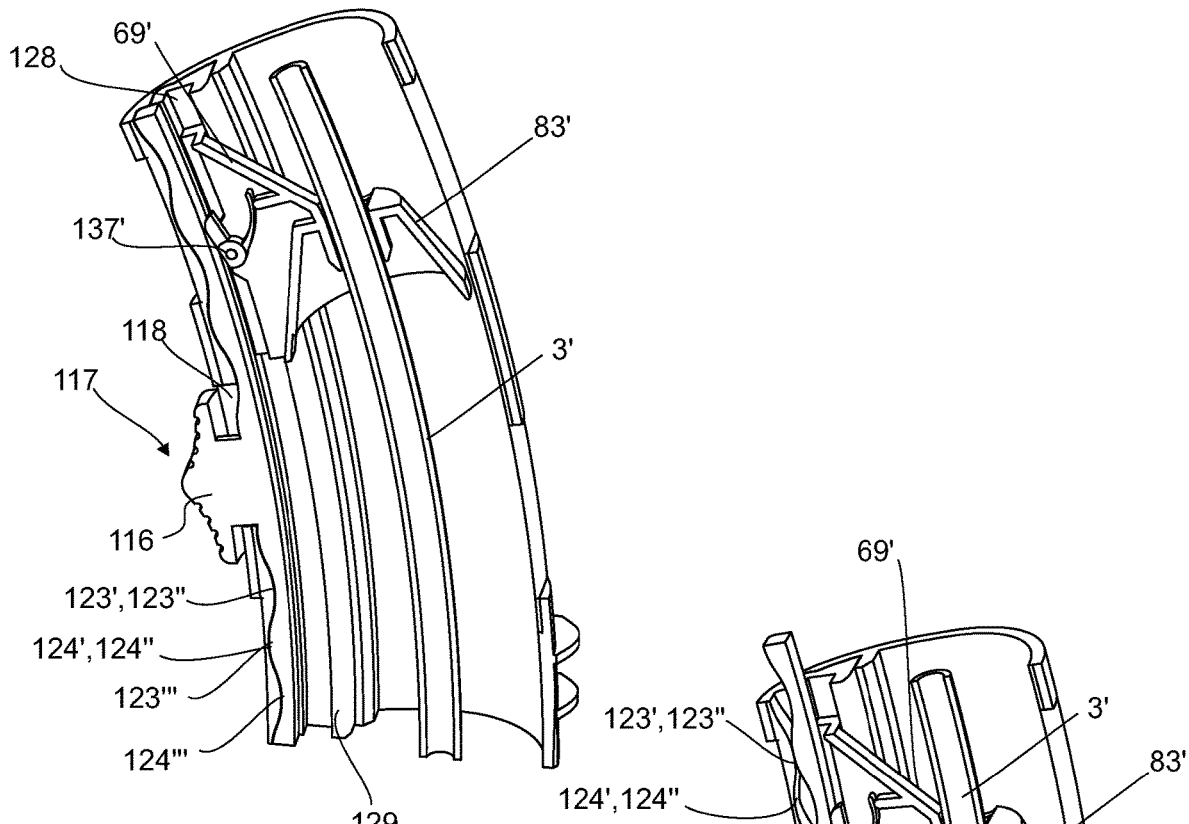
Figure 44B:
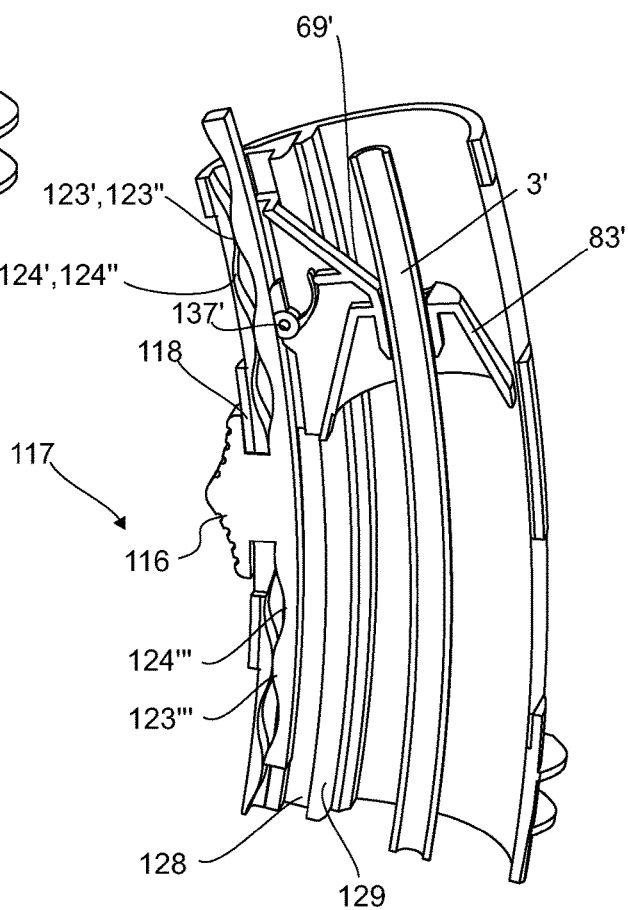

FIG. 1 is a perspective view of a first embodiment of an endotracheal tube inserting device of the present invention seen oblique form the side and from the actuators, FIG. 2 shows the same in an exploded view, FIG. 3 shows, in an enlarged scale, in perspective from the handle part towards the stylet part of the first embodiment of an endotracheal tube inserting device, the first string-operating member and the second string-operating member pivotably suspended on the suspension body, FIG. 4 shows the same without the second string-operating member, FIG. 5 is a perspective view of a first string-operating member for the first embodiment of an endotracheal tube inserting device, and seen from below, FIG. 6 is a side view of an associated second string-operating member, FIG. 7 is an enlarged perspective view of an associated suspension body seen from the proximal end, FIG. 8 shows the same seen from the opposite side, FIG. 9 is a side view inside the first shell part of the housing of the first embodiment of an endotracheal tube inserting device, FIG. 10 is a side view inside an associated second shell part, FIG. 11 is a perspective view of the shell parts in assembled state to achieve the housing of the first embodiment of an endotracheal tube inserting device, FIG. 12 is a perspective view of a moveable third rack part of a first embodiment of a tube ejecting mechanism, which moveable third rack part is seen from a third actuator, FIG. 13 is a perspective view seen from the tube connector of a wedge part of the first embodiment of a tube ejecting mechanism for use with the moveable third rack part, FIG. 14 is a perspective general side view of the first embodiment of an endotracheal tube inserting device having an endotracheal tube sheathed on the stylet part prior to use, FIG. 15 is a perspective general side view of the first embodiment of an endotracheal tube inserting device in an ejecting step of the endotracheal tube, FIG. 16 is an enlarged scale, perspective, fragmentary view of the handle part of the first embodiment of an endotracheal tube inserting device, without the second shell part, and where the proximal end of the stylet part is provided with an endotracheal tube positioned in the starting position prior to the endotracheal procedure, FIG. 17 shows the same seen from the side, FIG. 18 shows the same as FIG. 15 but in an ejecting state, FIG. 19 shows the same seen from the side, FIG. 20 is a view inside the first shell part of the first embodiment of an endotracheal tube inserting device, seen from the side, with the wedge part and the strings securing members exposed via the elongate guide member, however without endotracheal tube, and wherein the suspension body, the moveable third rack part and the string-operating members also have been left out, FIGS. 21-24 show bending steps and configurations of a first embodiment of a bendable tip part having both lateral and lengthwise offset first and second securing locations, FIG. 25 is an enlarged scale view of the tip-shaping member in the S-configuration seen in FIG. 23, FIG. 26 is an enlarged scale view of a modified bendable tip part in straight configuration, FIG. 27 is an enlarged scale view of a modified bendable tip part bend into C-shape, FIG. 28 is an enlarged scale view of the same bend into a J-shape, FIG. 29 is a lengthwise sectional view through a third embodiment of a bendable tip part, FIG. 30 illustrates the configuration of the first embodiment of an endotracheal tube inserting device in relaxed configuration next to a patient to be intubated, FIG. 31 illustrates the above configuration of the second embodiment of an endotracheal tube inserting device in relaxed configuration next to a patient to be intubated, FIGS. 32*a*, 32*b* and 32*c* are perspective views of a second embodiment of an endotracheal tube inserting device of the present invention seen form different sides, FIG. 33 is a longitudinal sectional view of FIG. 32*c* taken along line B-B, FIG. 34 is an exploded perspective view of the same, FIG. 35 is an enlarged scale perspective view of a second embodiment of a wedge part, FIGS. 36 and 37 are different perspective enlarged scale views of a first embodiment of a pawl member, FIG. 38 is a perspective enlarged scale view of a second embodiment of a pawl member, FIG. 39*a* is a perspective view seen from the first wedge face of the second embodiment of a wedge part with the second embodiment of a pawl member where the pawl member is in a first pivoted position protruding from the first wedge face, FIG. 39*b* shows the same seen from the side, FIGS. 39*c* and 39*d* correspond to FIGS. 39*a* and 39*b* but the pawl member is now in a second pivoted position substantially plane with the first wedge face, FIGS. 39*e* and 39*f* correspond 39*a* and 39*b* but to figs. the lateral pawl one of first member is now in the and the pivoted other lateral pawl member is position in the position substantially, second pivoted FIG. 40 is a lengthwise sectional view where third actuator is in its relaxed position ready to push the endotracheal tube-inserting device a stroke toward the distal stylet end, and where the distal end of the endotracheal tube and the distal end of the bendable tip part are shown in full line, FIG. 41 shows the same wherein the third actuator and the feeder component have performed said stroke towards the distal stylet end, FIG. 42 is a sectional view taken along line A-A in FIG. 32*c*, FIGS. 43*a* and 43*b* show the sliding flanges of the wedge part inside internal track in different positions of the fourth actuator, and FIGS. 44*a* and 44*b* are enlarged scale fragmentary vies of a step a retracting of an endotracheal tube by means of moveable fourth rack part.

A first embodiment of an endotracheal tube inserting device 1 is seen in perspective view in FIG. 1, and in a perspective exploded view in FIG. 2.

The endotracheal tube inserting device 1 comprises a handle part 2 and a stylet part 3. The stylet part 3 has an elongate guide member 4 that extends into a bendable tip part 6 at a distal stylet end 7 of a distal stylet end part 7*a*, and inside the handle part 2 at an opposite proximal stylet end part 8a that has a proximal stylet end 8.

The handle part 2 defines a receptacle in form of a housing 9 that accommodates at least a part of a mechanism to bend the bendable tip part 6, and at least a part of a mechanism to eject from said stylet part 3 an endotracheal tube (not shown) sheathed on the stylet part 3. In the present exemplary embodiment of an endotracheal tube inserting device 1 the elongate guide member 4 is shown to be a smoothly curved pipe, and the bendable tip part 6 is not transparent. The shown curvature of the elongate guide member 4 is an example and other curvatures, e.g. having larger or smaller radii, are foreseen within the scope of the present invention.

As seen best in FIG. 2 the mechanism to bend the bendable tip part 6 includes a first string member 10 and a second string member 11 extending inside the elongate guide member 4. The first string member 10 and the second string member 11 are both connected to a tip-shaping member 5 located at least partly inside a tubular cover 12 and having a first end 95 secured to the free distal tip 97 at the end 98 of the distal tip part 6 and an opposite second end 96 secured to the elongate guide member 4 or the stylet part 3. The tubular cover 12 and the tip-shaping member 5 are part of the bendable tip part 6.

The housing 9 has a first shell part 13 and an opposite second shell part 14 that, when assembled, provide a space for at least a part of an actuator means 15 for pulling and relaxing tensioning of the tip-shaping member 5 inside the tubular cover 12 by pulling and relaxing tensioning of the first string member 10 and the second string member 11, both of which are secured to said tip-shaping member 5 at different securing locations (not seen in FIG. 1 and FIG. 2) inside the tubular cover 12 of the bendable tip part 6.

A tip part operating member 16 thus includes at least the tip-shaping member 5, the first string member 10 and the second string member 11.

The actuator means 15 of the first embodiment of an endotracheal device 1 includes a suspension body 17, a first string-operating member 18, and a second string-operating member 19 pivotable suspended on the suspension body 17, as seen in more detail in the enlarged views of FIG. 3 and FIG. 4, in which FIGS. 3 and 4 other structural components of the endotracheal tube inserting device 1 have been left out to better visualize the pivoting "saddle"-arrangement of the string-operating members 18,19 on the suspension body 17.

As seen in FIGS. 3-6 a first string-operating member 18 of the actuator means 15 includes a first bifurcated lever body 20 having opposite first legs L1a,L1b arranged on opposite sides of the suspension body 17 about a first pivot axis P1 to allow the first lever body 20 to move up and down in relation to the suspension body 17, as indicated by double-pointed arrow A1. A second string-operating member 19 of the actuator means 15 includes a second bifurcated lever body 22 having opposite second legs L2a,L2b pivotably arranged about a second pivot axis P2 to allow the second lever body 22 to move up and down in relation to the suspension body 17, as indicated by double-pointed arrow A2.

The opposite first legs L1a,L1b have similar structures, which structures therefore are described in common with reference to a first leg L1b, as seen best in FIG. 4.

The first leg L1b of first lever body 20 has a first actuator lever arm 23 extending from the first pivot axis P1 to a first actuator 24. A first string-operating lever arm 25 extends opposite the first actuator lever arm 23 so that a first fulcrum 26 is established at the first pivot axis P1. A first angle a1 between the first actuator lever arm 23 and the first string-operating lever arm 25 are typically equal to or less than 90°, but a first angle a1 larger than 90° is not excluded. The first actuator lever arm 23 and the first string-operating lever arm 25 are connected to each other via a first intermediate arm 27 extending between the end 23a of the first actuator lever arm 23, at the transition of the first actuator lever arm 23 into the first actuator 18, and the end 25a of the first string-operating lever arm 25 opposite the first pivot axis P1 to confer structural strength to the first lever body 20. These three first arms, thus the first actuator lever arm 23, the first string-operating lever arm 25, and the first intermediate arm 27 together form an open triangular shape that makes the first lever body 20 lightweight and simple to mold, e.g. of a polymeric plastic material, such as a thermosetting material, without loosing the structural and dimensional strength needed for reliable and safe operation of the actuator means 15. The end 25a of the first string-operating lever arm 25 opposite the first pivot axis P1 has a first cavity or a first hook 28 for engaging a first string-securing member 29, to which a first proximal string end 30a of the first string member 10 is connected, so that actuating the first string-operating member 18 by applying a force to the first actuator 24 makes the first lever body 20 pivot about the first pivot axis P1 thereby moving the engaging first string-securing member 29 and first hook 28, or similar mating grasping means, lengthwise backwards inside the housing 9 to tension the first string member 10, which has a first distal string end 30b secured to the tip-shaping member 5, and pull the first string-securing location (not shown) at the tip-shaping member 5 away from the distal stylet end 7, thereby bending the tip-shaping member 5, and thus the tubular cover 12, that keeps movement of the first string member 10 and the tip-shaping member 5 under control, and prevents unintended lateral movement of any of the tip-shaping member 5 and the first string member 10 beyond the border of the tubular cover 12.

The opposite second legs L2a,L2b of the second lever body 22 have similar structure, which structure therefore is described in common with reference to a second leg L2a.

The second lever body 22 has a structure similar to the structure of the first lever body 20 and works in a similar manner. Accordingly, a second leg L2a of the second lever body 22 has a second actuator lever arm 31 extending from the second pivot axis P2 to a second actuator 32. A second string-operating lever arm 33 extends opposite the second actuator lever arm 31 so that a second fulcrum 34 is established at the second pivot axis P2. A second angle a2 between the second actuator lever arm 31 and the second string-operating lever arm 33 is outlined similarly to the first angle a1. The second actuator lever arm 31 and the second string-operating lever arm 33 are connected to each other via a second intermediate arm 35 extending between the end 31a of the second actuator lever arm 31, at the transition of the second actuator lever arm 31 into the second actuator 32, and the free end 33a of the second string-operating lever arm 33 opposite the second pivot axis P2, to confer structural strength to the second lever body 22. As for the first lever body 20 these three second arms, thus the second actuator lever arm 31, the second string-operating lever arm 33, and the second intermediate arm 34 together forms an open triangular shape. The end 33a of the second string-operating lever arm 33 opposite the second pivot axis P2 has a second cavity or a second hook 36 for engaging a second string-securing member 37, to which a second proximal string end 38a of the second string member 11 is connected. Actuating the second string-operating member 22 by applying a force to the second actuator 32 makes the second lever body 22 pivot about the second pivot axis P2 thereby moving the engaging second string-securing member 37 and second hook 36, or similar mating grasping means, simultaneously, lengthwise backwards inside the housing 9 to tension the second string member 11, which has a second distal string end 38b secured to the tip-shaping member 5, and pull the second string-securing location (not shown) at the tip-shaping member 5 away from the distal stylet end 7, thereby bending the tip-shaping member 5 by tensioning the second string-securing location. The second string-operating member 19 pulls at another string-securing location than the first string-securing location. In this manner it becomes possible to bend the bendable tip part 5 almost arbitrary and smoothly into any level of S-shape, mirror S-shape, C-shape or J-shape depending on the level of force applied to the respective actuators 24;32.

The bendable tip part 5 can thus be given a variety of bended shapes, and bending be customized for a certain airway anatomy by tensioning and relaxing tensioning of the respective string members 10,11 by operating the associated actuators, which considerably improves the ability of unobstructed passing of the stylet part 3 in between the vocal cords, even for difficult airways.

The first string-operating member 18 and the second string-operating member 19 have similar design and are disposed in spaced relationship along the length of the suspension body 17 to pivot individually at the same time or at different times without jamming.

As seen best in FIG. 5 the opposite first legs L1a,L1b of the first bifurcated lever body 20 extends into an U-shaped first actuator 24. The opposite first leg L1a,L1b extends into the first actuator legs 39a,39b of the U-shaped first actuator 24, which first actuator legs 39a,39b are connected by first bridging member 40 that has exterior ridges 41 for improved tactileness and increased friction when grasping the handle part 2 for operating and maneuvering the endotracheal tube inserting device 1.

The side view of FIG. 6 shows the second string-operating member 19 but since the first string-operating member 18 and the second string-operating member 19 in the present embodiment are identical, FIG. 6 could quite as well show the first string-operating member 18. The opposite second legs L2a,L2b of the second bifurcated lever body 22 extends into an U-shaped second actuator 32. The opposite second leg L2a,L2b extends into the second actuator legs 42a,42b of the U-shaped second actuator 32, which second actuator legs 42a,42b are connected by second bridging member 43 that has exterior ridges 44 for improved tactileness and increased friction when grasping the handle part 2 for operating and maneuvering the endotracheal tube inserting device 1.

An exemplary string-securing member 29;37 can e.g. be a freely suspended pin extending crosswise between the first shell part 13 and the second shell part 14 inside the housing 9. The pin is not connected to any of the shell parts 13,14 because it shall be able to move in response to pivoting the lever bodies 20,22. The engagement between the hook 28;36 and the string-securing member 29;37 however keeps the string member 10;11 under tension so that the string-securing member 29;37 not accidentally can disengage the hook 28:36 or cavity. Alternative ways of securing a string member to a lever body in a manner that allows the lever body to pull the string member backward when tensioned and move forward when tension is relieved is within the scope of the present invention. A string member can in the alternative simply be secured by a knot in an eye of the lever body.

FIGS. 7 and 8 are perspective views of the suspension body 17 that has a distal suspension body end 45 and an opposite proximal suspension body end 46, respectively. The suspension body 17 has opposite lengthwise extending first 47 and second side faces 48, an upper ridge 49 and a lower edge 50 extending lengthwise between said side faces 47,48. The upper ridge 49 is configured with alternating first crest 51 and first sag 52 at the distal suspension body end 45, and second crest 53 and second sag 54 at the proximal suspension body end 46. The alternating arrangement of crests 51,53 and sags 52,54 provides points of discontinuity along the curvature of the upper ridge 49 to define a first seat 55 for the first actuator 24 and a second seat 56 for the second actuator 32 when pivoted about respective pivot axis P1,P2.

Both the opposite first side face 47 and second side face 48 has a plurality of protruding securing pins 57 arranged to mate into corresponding female securing means 58 of the shell parts 13,14 of the housing 9 to secure the suspension body 17 in a manner inside the housing 9 wherein none of the suspension body 17, the securing pins 57 or the female securing means 58, e.g. bush mountings, can obstruct the operation of the actuator means 15 and the tube ejecting mechanism. For the present embodiments of an endotracheal tube inserting device 1 the securing pins 57 are arranged along or in the vicinity of the annular outer edge of the suspension body 17.

At the distal suspension body end 45 a groove 59 or recess in the first face 48 serves to receive, mount and align the proximal stylet end part 8a of the elongate guide member 4 for securing the elongate guide member 4 firmly to the suspension body 17. Securing can e.g. be achieved by gluing or by traverse pins.

In an alternative embodiment the protruding securing pins 57 can be provided at the shell parts 13,14 and the female securing means 58 be provided at the suspension body 17.

FIGS. 9, 10 and 11 show the shell parts 13,14 apart from each other and in assembled state to obtain the housing 9.

The proximal housing end 61 is closed, whereas the distal housing end 60 is open for passage of at least a length of the proximal stylet end part 8a of the stylet part 3. The upper lengthwise housing edge 62 has a proximal opening 63 for the pivotable passage of the first actuator 24 of the first string-operating member 18 and a distal opening 64 for the pivotable passage of the second actuator 32 of the second string-operating member 19. The first actuator 24 and the second actuator 32 constitute the buttons, which the operator uses to confer a desired curvature and shape to the distal tip part 6.

As seen in e.g. FIGS. 1 and 2 a first embodiment of a tube ejecting mechanism 65 to get the endotracheal tube (not shown) off the stylet part 3 includes a first embodiment of a ratchet mechanism 66 with a third actuator 67 that protrudes from the housing 9 opposite the proximal opening 63 and the distal opening 64.

The ratchet mechanism 66 has a rack part 68 and a wedge part 69, which wedge part 69 is seen in FIG. 13.

The rack part 68 is has an elongate first stationary rack part 70, an elongate second stationary rack part 71 and an elongate moveable third rack part 72, which elongate moveable third rack part 72 is shown in FIG. 12.

The elongate moveable third rack part 72 is, as shown in FIG. 2, disposed between the elongate first stationary rack part 70 and the elongate second stationary rack part 71. The three elongate rack parts 70,71,72 extend lengthwise from the proximal housing end 61 towards the distal housing end 60 inside the housing 9 opposite the proximal opening 63 and the distal opening 64.

The third actuator 67 of the elongate moveable third rack part 72 protrudes through an ejector slot 74 in the housing 9 towards the proximal housing end 61 opposite the proximal opening 63 and the distal opening 6 for pivotable passage of the actuators 24,32. Thus the third actuator 67 is provided at a proximal end 73 of the elongate moveable third rack part 72 to be accessible to move said elongate moveable third rack part 72 in a translatory movement that is restricted by the ejector slot 74 towards the bendable tip part 6.

The elongate moveable third rack part 72, which is shown in the separate view of FIG. 12, is suspended inside the housing 9 by means of a spring 75 or similar resilient means, such as an elastic strap. The spring 75 is stretched and tensioned when the elongate moveable third rack part 72 is moved lengthwise along the housing 9 upon a stroke of the third actuator 67 in order to displace the elongate moveable third rack part 72 forward between the elongate first stationary rack part 70 and elongate second stationary rack part 71.

The elongate first stationary rack part 70 has first teeth 76, the elongate second stationary rack part 71 has second teeth 77, and the elongate moveable third rack part 72 has third teeth 78.

As shown in the perspective view of FIG. 13, and in FIGS. 16-19 the wedge part 69 has a center wedge part 79 that engages between the third teeth 78 of the elongate moveable third rack part 72. The center wedge part 79 is located between a first lateral wedge part 80 to engage the first teeth 76 of the elongate first stationary rack part 7 and a second lateral wedge part 81 to engage the second teeth 77 of the elongate second stationary rack part 71. The center wedge part 79, the first lateral wedge part 80, and the second lateral wedge part 81 are provided at a proximal end 82 of the wedge part 69 and a tube connector 83 is provided at the distal wedge part 84. The tube connector 83 is a cylindrical tapering plug with a bore 85 for receiving the elongate guide member 4 to allow the wedge part 69 to be fitted in fixed position on said elongate guide member 4, or preferably to slide along said elongate guide member 4 in response to operating the third actuator 67 and thus the movable third elongate rack 72 to eject an endotracheal tube 86, as shown in general in FIGS. 14 and 15.

The endotracheal tube 86 has a tube part 87a and an airway connector 87b that mates around the tube connector 83 of the wedge part 69, to push the endotracheal tube 86 off the elongate guide member 4 when the third actuator 67 of the elongate moveable third rack part 72 displaces the wedge part 69 and thus the endotracheal tube 86 forward towards the distal stylet end 7.

The ejecting steps are seen more clearly in FIGS. 16-19. The state shown in FIGS. 16 and 17 corresponds to the state shown in FIG. 14, and the state shown in FIGS. 18 and 19 corresponds to the state shown in FIG. 15 where the endotracheal tube 86 has been moved closer to the distal tip part 6 by means of the tube ejecting mechanism 65.

In FIGS. 16 and 17 the second shell part 14 has been removed to illustrate the interior components and structures more or less accommodated by the handle part 2. The positions of the wedge part 69 in relation to the elongate stationary rack parts 70,71, the third actuator 67, and the elongate moveable third rack part 72 of the ratchet mechanism 66 inside the housing 9 is shown in the starting position ready for the endotracheal procedure. The elongate moveable third rack part 72 is in retracted position in the housing 9, and the spring 75, that has one spring end 88 secured at a spring securing location 89 inside the proximal housing end 61 of the housing 9, and an opposite end 90 secured to the proximal end 91 of the elongate moveable third rack part 72, is in relaxed state. An endotracheal tube 86 is sheathed on the elongate guide member 4, and the airway connector 87 of the endotracheal tube 86 mates around the tube connector 83 of the wedge part 69.

When the third actuator 73 is depressed in the direction of the bendable tip part 6 by application of a force, as indicated by arrow A in FIGS. 18 and 19, the engaging center wedge part 79 and third teeth 78 of elongate moveable third rack part 72 travel along. During a stroke of the third actuator 67 the engaging tube connector 83 and airway connector 87 of the endotracheal tube 86, and thus also said endotracheal tube 86, are moved a stroke length closer to the bendable tip part 6. At the end of the travel of the stroke, the first 80 and second lateral wedge parts 81 engage the adjacent first teeth 76 and the second teeth 77 so that the wedge part 69 cannot return towards the proximal housing end 61 when the elongate moveable third rack part 72 returns to the proximal housing end 61 to repeat the stroke. When the elongate moveable third rack part 72 has returned to the relaxed condition of the spring 75, another third tooth or section of third teeth 78 closer to the distal end 92 of the elongate moveable third rack part 72 is made available and exposed for further displacing the wedge part 69 yet a stroke forward by its engagement with the center wedge part 79. Strokes can be repeated as long as the length of the elongate moveable third rack part 72 is available for engagement with the center wedge part 79. When the wedge part 69 reaches or is close to the distal end 92 of the elongate moveable third rack part 72 further strokes cannot move the wedge part 69 further forward. The tube connector 83 may not automatically or immediately be released from the airway connector 87 to leave the endotracheal tube 86 in trachea for subsequent connection to appropriate ventilation equipment upon retraction of the stylet part 3. Instead the operator may chose to set the endotracheal tube 86 free before the wedge part 69 reaches the distal end 92 of the elongate moveable third rack part 72. Accordingly, the operator may choose to separate the endotracheal tube 86 and the endotracheal tube inserting device 1 at any convenient stage during the endotracheal procedure.

As seen in FIG. 20 the first string member 10, e.g. a metal wire, is secured to the first string-securing member 29, e.g. a cross pin, freely floating in the housing or being supported again the shell walls. Similarly the second string member 10, e.g. a metal wire, is secured to the second string-securing member 37, e.g. a cross pin, lengthwise offset the first string member 10. The string-securing members 29;37 are grasped by the first string-operating member 18, and the second string-operating member 19, respectively, as described above, to pull the string members 10,11, simultaneously or independently, to same or different extent, in and out of the elongate hollow member 4 a distance corresponding to up to the maximum length achievable by a full depression and pivoting of a string-operating member.

This novel and inventive configuration and design of an endotracheal tube inserting device 1 provides a multitude of options and a huge degree of freedom for configuring the shape of the bendable tip part 6 to adopt a shape suited for maneuvering in almost any imaginable airway anatomy.

Various examples of curvatures and shapes that can be given to the bendable tip part 6 by operating the tip part operating member 16 using the actuator means 15 is shown in the subsequent FIGS. 21 24. The endotracheal tube inserting device 1 shown in FIGS. 21 24 is shown with transparent elongate guide member 4 and transparent tubular cover 12 to illustrate that the first string member 10 and the second string member 11 extend along the length of said elongate guide member 4 and further inside the tubular cover 12, inside which the tip-shaping member 5 is located. The first string member 10 is secured at a first string-securing location 93 retracted from the first end 95 of the tip-shaping member 5, in the present case on top of a tip-shaping member 5 in form of a plate spring, to be operated by means of the first actuator 24, as indicated by curved arrow A1. The second string member 11 is secured to the tip-shaping member 5 at the bottom of the tip-shaping member 5 at a second string-securing location 94 downstream the first string-securing location 93 to be operated by means of the second actuator 32, as indicated by curved arrow A2. Thus the first string-securing location 93 is both lateral and lengthwise offset the second string-securing location 94 and closer to the handle part 2, as seen more clearly in the associated FIG. 24, which is an enlarged scale view of the bendable tip part 6 seen in FIG. 23.

In FIG. 21 neither the first string-operating member 18 nor the second string-operating member 19 are pivoted and the bendable tip part 6 are straight without any bending(s). Neither the first string-securing location 93 nor the second string-securing location 94 has been activated.

In the situation shown in FIG. 22 only the second string-operating member 19 has been actuated by depressing the second actuator 32, as indicated by arrow A2. Pressing on the second actuator 32 moves the second string-securing member 37 back inside the housing 9 whereby the second string-securing location 94 is pulled closer to the handle part 2, to provide the bendable tip part 6 with a C-shape wherein the free distal tip 97 of the bendable tip part 6 has been turned upwards, referring to the orientation seen FIG. 22.

In the situation shown in FIG. 23 only the first string-operating member 18 has been actuated by depressing the first actuator 24, as indicated by arrow A1. Pressing on the first actuator 24 moves the first string-securing member 29 back inside the housing 9 whereby the first string-securing location 93 is pulled closer to the handle part 2, to provide the bendable tip part 6 with a J-shape, wherein the distal free distal tip 97 of the bendable tip part 6 has been turned downwards, using the orientation of FIG. 23.

In the situation shown in FIG. 24 both the first string-operating member 18 and the second string-operating member 19 have been actuated by depressing the first actuator 24, as indicated by arrow A1, and the second actuator 32, as indicated by arrow A2. Pressing on both the actuators 24,32 move both string-securing members 29,37 back inside the housing 9 whereby both string-securing locations 93,94 are pulled closer to the handle part 2, to provide the bendable tip part 6 with an S-shape.

Because the tip-shaping member 5 is confined inside the tubular cover 12, any possible movement by the tip-shaping member 5 in response to operation of the actuators 24,32 are also controlled and confined by the presence of said tubular cover 12 that restricts lateral movement of the plate spring 5a beyond the border of the tubular cover 12, but permits at least lengthwise bending because of flexibility of the tubular cover 12 of the bendable tip part 6.

Various levels of force applied to the actuators 24,32 facilitate the provision of even further shapes than the shapes shown in FIGS. 21-24.

FIG. 25 is an enlarged scale view of the first embodiment of a tip-shaping member 5 in the S-configuration seen in FIG. 24.

A second embodiment of a tip-shaping member 5' is seen in FIGS. 26, 27 and 28. The shapes and configuration of the bendable tip part 6 shown in FIGS. 21, 22 and 23 can also be obtained by implementation of the second embodiment of a tip-shaping member 5', which second embodiment of a tip-shaping member 5' has laterally offset first string-securing location 93' and second string-securing location 94'. Thus for the second embodiment of a tip-shaping member 5' the string-securing locations 93', 94' are not lengthwise offset. Using the orientation shown in FIGS. 26, 27, and 28 the first string-securing location 93' is on top side of the tip-shaping member 5', e.g. a plate spring member 5", and the second string-securing location 94' is on the bottom side of the tip-shaping member 5', using the orientation seen in FIGS. 26, 27 and 28.

In FIG. 26 the second embodiment of a tip-shaping member 5' is in a relaxed condition corresponding to the condition shown in FIG. 21 for the first embodiment of a tip-shaping member 5.

In FIG. 27 the second embodiment of a tip-shaping member 5' is in same C-shaped configuration as in FIG. 22, and in FIG. 28 the second embodiment of a tip-shaping member 5' is in a J-shaped configuration similar to the configuration shown in FIG. 23.

FIG. 29 is a lengthwise sectional view through a third embodiment of a bendable tip part 6' having a third embodiment of a tip-shaping member 5''' in form of a flat plate spring member 5" of spring steel with pulley wheels arranged inside a tubular cover 12'. The first end 95" of the tubular cover 12' is configured with a flexible resilient tip 99, the function of which will be described in further details in relation to FIGS. 29-34. The first string-securing location and the second string-securing location are defined substantially as for the first embodiment of a bendable tip part 6 shown in FIG. 25 and for like part same reference numerals are used.

The bendable tip part 6' has a distal pulley wheel 100 provided on a bottom side 101 of the plate spring member 5" at a first pulley wheel location W1 at the free distal tip 97' of the distal tip part 6', a proximal pulley wheel 103 is provided on a top side 102 of the at least one plate spring member 5" opposite the first side 101 at a second pulley wheel location W2 spaced apart from the first pulley wheel location W1, using the orientation shown in FIG. 29. A distal intermediate pulley wheel 104 and a proximal intermediate pulley wheel 105 are provided adjacent each other on opposite sides 101,102 of the plate spring member 5" at an intermediate pulley wheel location W3 between the first pulley wheel location W1 and the second pulley wheel location W2. The plate spring member 5" passes between the distal intermediate pulley wheel 104 and the proximal intermediate pulley wheel 105 so that the distal intermediate pulley wheel 104 is provided on the bottom side 1 O l of the plate spring member 5" and the proximal intermediate pulley wheel 105 is provided on the top side 102 of the plate spring member 5", and so that the arrangement of the intermediate pulley wheels 104,105 establishes, as indicated by reference numeral F, a fixed pivot point or fixed pivot location.

The first string member 10 is secured at a first string-securing location 93" to the proximal intermediate pulley wheel 105 at the intermediate pulley wheel location W3, e.g. to an axle (not shown) of the proximal intermediate pulley wheel 105 or to the plate spring member 5" at a similar suitable location.

The second string member 11 is secured at a second string-securing location 94" to the distal pulley wheel 100 at the first pulley wheel location W1, e.g. secured to an axle (not shown) of the distal pulley wheel 100 or to the plate spring member 5" at a similar suitable location.

The plate spring member 5" has a pre-shaped curvature and a Z-bending 106 is present at the fixed pivot location at the intermediate pulley wheel location W3. The Z-bending allows the plate spring member 5" to pass between the intermediate pulley wheels 104,105 when the plate spring member 5" is in its curved configuration and so that the pulley wheels can act on the respective side of plate spring member 5". The Z-shaped bending 106 can be fully straightened, e.g. if needed to insert the bendable tip part into the endotracheal tube that should be guided in place inside trachea.

The Z-shaped bending 106 of the curved bendable tip part 6' can offset the lengths of the plate spring member 5" on opposite sides of the intermediate pulley wheel location W3 to different degree, although the degree of offset between the parallel legs of the Z-shape is restricted by the internal diameter of the tubular cover 12', and by the fact that the string members 10,11 shall be able to be pulled and operated easily by the string-operating members.

The first end 95' of the tip-shaping member 5''' has a C-shaped bending 107 that passes around the distal pulley wheel 100. Such a C-shaped bending 17 is optional.

The first distal string end 30b' of the first string member 10 is secured to the proximal intermediate pulley wheel 105 wherefrom the first string member 10 runs around the proximal pulley wheel 103 back to the proximal intermediate pulley wheel 105 and around said proximal intermediate pulley wheel 105 back beyond the proximal pulley wheel 103 for having a first proximal string end 30a' operatively secured to a corresponding first string-operating member associated with the handle part. The second distal string end 38b' is secured to the distal pulley wheel 100 wherefrom the second string member 11 runs around the distal intermediate pulley wheel 104 back to the distal pulley wheel 100 and around said distal pulley wheel 100 and back beyond the distal intermediate pulley wheel 104 and further on beyond the proximal pulley wheel 103 for having a second proximal string end 38a' operatively secured to a corresponding second string-operating member associated with the handle part.

The proximal length, which faces the patient and which is the portion of the bendable distal tip part 6' between the proximal pulley wheel 103 and the proximal intermediate pulley wheel 105, is indicated by reference numeral L2. The distal length of the bendable distal tip part 6' between the distal intermediate pulley wheel 104 and the distal pulley wheel 100 is indicated by reference numeral L2, which distal length L1 is the portion of the bendable distal tip part 6' in extension of the proximal length and end in the free distal tip 97'.

FIG. 30 and FIG. 31 illustrate in general the configuration of the first embodiment of an endotracheal tube inserting device 1 and the second embodiment of an endotracheal tube inserting device 1' in relaxed configuration next to a patient 119 to be intubated in an intubation procedure monitored using a video laryngoscope 120. The endotracheal tube inserting device 1,1' has not been put in place inside trachea yet.

Emphasis is made that although the first lever body and the second lever body of the first embodiment of an endotracheal tube inserting device are described as a triangle with a center hole, other lever body designs are within the scope of the present invention. The triangular structure can e.g. be replaced by a solid triangular plate, in which case the edge areas of the triangle are equivalent to the arms of the triangular structure and is utilized and functions in a similar manner. Other shapes than triangular, such as oval, polygonal and circular are also possible within the scope of the present invention. The outline of the first actuator and of the second actuator is curved, preferably having similar curvature as defined by the pivot radius.

In the above first embodiment of an endotracheal tube inserting device the first lever body and the second lever body where both designed with pivotable lever arms. Alternative embodiments of actuators may include alternatives to such lever bodies. Thus axial displacing the first distal securing location and the second distal securing location may in the alternative be provided by connecting the first proximal string end of the corresponding first string member and the second proximal string end of the corresponding second proximal string member, respectively, to e.g. a toggle mechanism, an articulated mechanism, a rotating mechanism, or even a gear transmission. These alternatives are however more space-demanding, which makes the handle part larger and less handy. These alternatives are also more complex structures that make the endotracheal tube inserting device more expensive and more vulnerable to malfunction.

FIGS. 32a, 32b and 32c are perspective views of a second embodiment of an endotracheal tube inserting device 1' of the present invention seen from different sides. The second embodiment of an endotracheal tube inserting device 1' may utilize any of the bendable tip parts 6,6' and the same or different mechanism as the first embodiment of an endotracheal tube inserting device 1 to eject the endotracheal tube 86 off the stylet part 3'. FIG. 33 is a longitudinal sectional view of FIG. 32c, where the part of the housing 9' having the third actuator has been removed.

The second embodiment of an endotracheal tube inserting device 1' differs from the first embodiment of an endotracheal tube inserting device 1 in the configuration of the housing of the handle part, the configuration and position of the string-operating members and thus the paths of the string members, by the configuration and position of the first actuator and the second actuator, and in the tube ejecting mechanism, however for like parts same reference numerals are used, Similar part having same function are indicated by same reference numeral and an apostrophe where feasible. Only different features are specifically described below. The string members are not shown.

The housing 9' is a curved tubular body 108 delimited by an exterior tubular wall 109 within which the proximal stylet end part 8a' is at least partly located. The elongate guide member 4' has, using e.g. the orientation of FIG. 33, an S-shape, thus the distal stylet end part 7a' and the proximal stylet end part 8a' curves in opposite directions. The housing 9' follows the curvature of at least a length of the proximal stylet end part 8a'. The bendable tip part 6' in its pre-shaped relaxed condition continues to curve in extension of the distal stylet end part 7a'. This configuration of curvatures avails the operator of the endotracheal tube inserting device with good working posture and good working conditions to the benefit of the patient, and the intubation can be done carefully and considerate. The second embodiment of an endotracheal tube inserting device 1' has the handle part 2' to bend backwards thereby providing for good clearance to the patient when inserting the bendable tip part 6' via the mouth into trachea while also preserving good control of the device 1'.

The first string member and the second string member pass inside the hollow elongate stylet part 3' close to the proximal stylet end 8' of the proximal stylet end part 8a', whereas the distal housing end 60' allows exit of the stylet part 3'. The first string member and the second string member may enter the housing 9' and pass over various guide means (not shown) to avoid kinking of said string members and to provide for an unobstructed and a smooth pulling and relaxing of said string members upon operating the first actuator 24' of the first string-operating member 18' and the second actuator 32' of the second string-operating member 19'.

The first actuator 24' of the first string-operating member 18' is constituted by a first curved flap 110 and the second actuator 32' of the second string-operating member 19' is constituted by a second curved flap 111. The curved flaps 110,111 constitute the buttons, which the operator uses to confer a desired curvature and shape to the distal tip part 6' during intubating a patient 119 using e.g. the index finger on the first curved flap 110 and the long finger one the second curved flap 111 below the first curved flap 110.

Although not visible in FIGS. 32a, 32b, 32c and 33 the first string member has a first proximal string end secured to the first curved flap 110 and an opposite first distal string end secured at a first string-securing location at the bendable tip part 6'. The first string member runs from the bendable tip part 6' through the stylet part 3' out of the proximal stylet end 8' and through and/or along the exterior tubular wall 109 at an proximal housing end 61' of the housing 9'. The first string member continues along the exterior face 114 of the exterior tubular wall 109 guided on said exterior tubular wall 109 or inside the housing 9' for having the first proximal string end securely and operatively connected to the first curved flap 110.

In a similar manner the second string member has a second proximal string end connected to the second curved flap 111 and an opposite second distal string end secured at a second string-securing location at the bendable tip part 6'. The second string member runs from the bendable tip part 6' through the stylet part 3' out of the proximal stylet end 8' and through the exterior tubular wall 109 at the proximal housing end 61' of the housing 9'. The second string member continues along the exterior face 114 of the exterior tubular wall 109 guided on said exterior tubular wall 109 or inside the housing 9' for having the second proximal string end securely and operatively connected to the second curved flap 111.

The proximal stylet end part 8a' may be kept fixed, optionally centered inside the lumen of the tubular body 109 at the proximal housing end 61' by means of a centering body 112 located in relation to the housing 9'.

The curved flaps 110,111 are hinged to the exterior wall 109 of the tubular body 108 in a manner that allow the curved flaps 110,111 to be released from a forced position close to the tubular exterior wall 109 by an elastic force and jump back to a released and relaxed position farther away from said exterior tubular wall 109. Thus the curved flaps 110,111 are hinged to the tubular body 108 in a manner that provide them with a certain degree of springiness and substantial spring-property.

In the second embodiment of an endotracheal tube inserting device 1' seen in FIG. 32a, 32b, 32c and FIG. 33 the string members can run inside guide tubes (not shown) arranged inside or outside the tubular body 109 to be kept out of the way of the tube ejecting mechanism, run in tracks or in any other way.

Instead of being curved flaps the actuators of the string-operating members can be two rocker arms to which the string members have been secured, in same, similar or different manners as described for the first embodiment of an endotracheal tube inserting device 1 or second embodiment of an endotracheal tube inserting device 1', Opposite the proximal housing end 61' of the housing 9', said housing 9' has an distal housing end 60' where the stylet part 3' exit the housing 9'. The exterior tubular wall 109 of the distal housing end 60' has finger location means 113 on one or both of the sides of the curved flaps 110,111 farthest from each other, thus the side of the curved flaps 110,111 not immediate adjacent each other. The finger location means 113 helps the operator to grasp around the tubular body 108 in the correct manner for use of the endotracheal tube inserting device 1' to operate the actuators 24'32'.

An endotracheal tube 86 can be mounted on and secured along the stylet part 3' as described for the first embodiment of an endotracheal tube inserting device 1, and the endotracheal tube inserting device 1' can also have a mechanism 121 to eject the endotracheal tube off the stylet part 3' as well as a mechanism 117 to return the endotracheal tube to its start position closest to the upper housing end 61'.

FIG. 34 is an exploded perspective view of the second embodiment of an endotracheal tube inserting device 1', seen in FIGS. 32a, 32b, 32c and 33, and illustrating the main components of the second embodiment of a tube ejecting mechanism 121 and a tube retracting mechanism 117.

The tube ejecting mechanism 121 comprises a wedge part 69' with a tube connector 83', and a ratchet mechanism 66'. The ratchet mechanism 66' has a rack part 68' that includes an elongate first stationary rack part 70', which is integral with the first shell part 13', an elongate second stationary rack part 71' which is integral with the second shell part 14', and an elongate feeder component 129 that is moveable in relation to the stationary rack parts 70';71'. The elongate first stationary rack part 70' of the first shell part 13' and the elongate second stationary rack part 71' of the second shell part 14' combine into an elongate rack part groove 122 of the tubular housing 9'. The elongate rack part groove 122 has alternating teeth, provided by aligned first teeth 123' of the elongate first stationary rack part 70' and second teeth 123" provided by the elongate second stationary rack part 71'. Preferably the aligned first teeth 123' and second teeth 123" are not pointed but constituted by alternating first 123' crests and first troughs 124' of the elongate first stationary rack part 70' and alternating second crests 123" and second troughs 124" of the elongate second stationary rack part 71', as also seen in FIGS. 43a and 43b.

The tube connector 83' of the wedge part 69' carries the airway connector 87 of the endotracheal tube 86. The tube connector 83' has a central bore 147 for being slidable mounted on the stylet part 3'.

The third actuator 67' is provided on an elongate feeder component 129 to move the wedge part 69' in response to a stroke performed by the feeder component 129 upon application of a force to the third actuator 67' towards the distal end of the stylet part 3'.

As seen in FIG. 35 a shaft bearing 134 extends, crosswise the first wedge face 132 of the wedge part 69' and serves to receive a main body 136 of a first embodiment of a pawl member 137 seen in FIGS. 36 and 37, or the main body 136' of the second embodiment of a pawl member 137' seen in FIG. 38. The wedge part has a first sliding flange 126 and an opposite second sliding flange 131. The shaft bearing 134 extends into an indent, recess, groove or stop 144.

The first embodiment of a pawl member 137 seen in enlarged scale views in FIGS. 36 and 37 has lateral wedge parts in form of lateral pawl members 138a,138b that protrudes perpendicular to the longitudinal axis X of the main body 136 at the free ends 139a,139b of said main body

136. The lateral pawl members 138*a*,138*b* have respective friction pads 140*a*,140*b* to increase friction if and when the main body 136 moves inside any of a first internal track 125 or second internal track 128 of the housing 9', or inside or a third internal track of the feeder component 129, or when the moveable fourth rack part 115 moves along the rack part groove 122. The lateral pawl members 138*a*,138*b* are shown as being rather rounded, but can within the scope of the present invention have any other cross-sections. The term "lateral pawl members" used in context with the pawl member should not be construed as limiting for the shape of the element that mate inside an internal track provided the element allows the "lateral pawl member" of the main body to pivot inside an internal track to slide the wedge part 69' towards the distal stylet end or slide the moveable fourth rack part 115 towards the proximal stylet end.

The amount of friction between a lateral pawl member and an internal track depends amongst other on the force applied to the third actuator 67' and the lengthwise displaced position of the feeder component 129.

A center pawl member 141, which is provided between the lateral pawl members 138*a*,138*b* and being angular offset counter-clockwise said lateral pawl members 138*a*, 138*b*, using the orientation of FIG. 36, can pivot into frictional contact with a back side 142 of the elongate moveable fourth rack part 115 to drive the wedge part 69' in the direction back to the proximal stylet end.

A spring arm 143 protrudes angular offset clockwise said lateral pawl members. The spring arm 143 can be located resilient and pivotable in the indent 144 arranged in extension of the shaft bearing 134 of the wedge part 69' to act as a compression spring to increase the pressure of the center pawl member 141 on the back side 142 of the elongate moveable fourth rack part 115, and thus enforcing the driving force induced by moving the feeder component 129 when actuating the third actuator 67'. The opposite lateral pawl members 138*a*,138*b* may remain fully or partly inside their respective internal tracks upon a stroke of the third actuator 67'.

FIG. 38 is a perspective view of a second embodiment of a pawl member 137'. The second embodiment of a pawl member 137' differs from the first embodiment of a pawl member 137 in being a two part assembly.

As illustrated in FIGS. 39*a* 39*f* the pawl member 137' is pivotably arranged in the shaft bearing 134. Although FIG. 39*a*-39*f* show the second embodiment of a pawl member, the first embodiment of a pawl member 137 can also be used.

The second embodiment of a pawl member 137' is composed of a first lateral pawl member 138*a*' and a second lateral pawl member 138*b*' which can pivot about the shaft 127 independent of each other in response to moving of the wedge part 69'. The first lateral pawl member 138*a*' and the second lateral pawl member 138*b*' is pivotable and slidable arranged in the first internal track 125 of the housing 9' and the third internal track 130 of the feeder component 129 opposite each other, respectively.

The center pawl member 141' is composed of a first center pawl member 141*a* integral with the first lateral pawl member 138*a*' and a second lateral pawl member 141*b* integral with the second pawl member 141*b*, so that the first and second center pawl member are able to pivot together with the corresponding lateral pawl member.

Similarly the spring arm 143' for the second embodiment of a pawl member 137' is a two part member where a first spring arm 143*a* is provided on the first lateral pawl member 138*a*' angular offset the first center pawl member 141*a*, and the second spring arm 143*b* is provided on the second lateral pawl member 138*b*' angular offset the second center pawl member 141*b*. The angular offset between the center pawl members 141*a*,141*b* and the spring arms 143*a*,143*b* decides the pressure force that the center pawl member 141*a*,141*b* applies to the back side 142 of the fourth moveable rack part 115 to return the wedge part 69' to the proximal stylet end and optionally also the force that the lateral pawl members 138*a*',138*b*' apply on the internal tracks to move the wedge part 69' towards the distal stylet end.

In the situation in FIG. 40 the wedge part has already been displaced somewhat forward during a stroke of the feeder component 129 or may be in its start position depending on how far inside the housing 9' the wedge part 69' is initially positioned. During a stroke the lateral pawl members 138*a*', 138*b*' pivot inside the opposite first internal track 125 and second internal track 130, so that at least a lateral pawl member can engage with its free tip inside the third internal track 130, to an extent that allows the feeder component 129 to carry the wedge part 69' along in the direction of the stroke performed by the third actuator 67', which is not visible in FIGS. 40 and 41. The lateral pawl members 138*a*',138*b*' are asymmetrical about the shaft 127 and have a respective tapered free end orientated towards the proximal stylet end. Optionally at least the lateral pawl members inside the second internal track is put under slight pressure by the corresponding spring arms, whereby said lateral pawl member take hold of the feeder component 129 to be brought along together with the wedge apart and the endotracheal tube. Optionally both lateral pawl members are put under pressure during a stroke of the feeder component. The feeder component 129 has been retracted by the second resilient and/or elastic member 146 and is ready for a new stroke.

The length of the actuator slot 118 for the third actuator 67' defines the maximum length that the wedge part 69' can be displaced during a stroke.

In the situation of FIG. 40 the feeder component 129 the second resilient and/or elastic member 146 is not tensioned and is ready for a new stroke to advance the wedge part, which stroke is shown performed in the situation seen in FIG. 41 wherein the endotracheal tube is moved closer to the distal tip 97'.

It may be preferred that when a force is applied to the third actuator 67' the feeder component 129 is displaced in the second internal track 128 of the housing 9', which forces the lateral pawl member that protrudes together with the second sliding flange of the wedge part inside the second internal track of the feeder component, to pivot in the main bearing to pick up the sliding feeder component and slide along due to the tapering of the lateral wedge part facing towards the proximal stylet end. The opposite first lateral pawl member slides in the opposite first internal track of the housing to provide for a stable sliding that does not make the sliding wedge part 69' skew. The central pawl member 141' is in this position free of the back side 141 of the fourth moveable rack part 115, or at least in minimum contact, so that the downwards moving of the wedge part 69' is not obstructed or only obstructed inferiorly.

The first 125, second 128 and third 130 internal tracks are seen best in the cross-sectional views of FIG. 42 and in FIGS. 43*a* and 43*b*. The interior of the housing is configured with the first internal track 125 for receiving the first sliding flange 126 of the wedge part 69', and the second internal track 128 for slidingly receiving the feeder component 129. The feeder component 129 has the third internal track 130 for receiving the second sliding flange 131 of the wedge part 69'. The wedge part 69' has a first wedge face 132 arranged facing the elongate rack parts 70', 71', 129 and an opposite second wedge face 133 wherefrom the tube connector 83' protrudes.

The tube retracting mechanism 117 includes a moveable fourth rack part 115 with a fourth actuator 116. The moveable fourth rack part 115 is arranged to be lengthwise and stepwise displaced in the elongate rack part groove 122. To that aspect the fourth actuator 116 protrudes through an actuator slot 118 in the tubular housing 9' to be moved up and down in a restricted manner. The moveable fourth rack part 115 has alternating third crests 123''' and troughs 124'''. The third crests 123''' and third troughs 124''' mate the first and second crests 123';123" and first and second troughs 124';124" of the rack part groove 122 to displace the wedge part 69' for moving the wedge part 69' with the endotracheal tube 86 back to the proximal stylet end 8' should the need arise to reposition the endotracheal tube on the stylet part while the distal tip is still inside the patient.

The tube retracting mechanism 117 includes a first resilient and/or elastic member 145 at the distal housing end 60' and the tube ejecting mechanism includes a second resilient and/or elastic member 146 at the proximal housing end 61'.

The tube retracting mechanism 117 further includes the fourth moveable rack part that is arranged to be automatically, at least partly, retracted towards the distal housing end 60' and the wedge part 69', thus be at least partly returned to its start position at the proximal housing end 61' by means of the first resilient and/or elastic member 145. Similarly the feeder component 129 may be automatically retracted by means of the second resilient and/or elastic member 146 at the proximal housing end 61' towards the proximal housing end 61' after the wedge part 69' has been at least partly displaced to its advanced position on the stylet part to repeat a stroke.

The function of the elongate moveable fourth rack part 115 and its co-operation with the pawl member is seen in the sectional fragmentary views of FIGS. 44*a* and 44*b*.

When the fourth actuator 116 is pressed towards the proximal housing end 61' from the position seen in FIG. 43, the elongate moveable fourth rack part 115 is lifted up from the rack part groove 122 to be able to move lengthwise in the rack part groove 122, as shown in FIG. 44, whereby one third crest 123''' of the elongate moveable fourth rack part 115 moves on top of the adjacently facing first 123' and second crest 123" of the first and second rack part inside the rack part groove 122 thereby applying pressure to the pivotable pawl member 137'. The pressure on the center pawl member 141' of the pivotable pawl member 137' also tensions the spring arm 143', so that the wedge part can be forced back one step after the other per stroke of the fourth actuator to the proximal housing end 61'.

The above described second embodiment of an endotracheal tube inserting device can be configured with the actuator flaps and the third actuator positioned for use by right hand or left hand. Due to the actuator flaps being positioned on the side of the housing the index finger will inherently be placed on the second flap and the middle finger be placed on the first body while the other fingers grasp around the housing, so that the thumb can be used to operate the third actuator of the tube ejecting mechanism.

Although the above first embodiment of an endotracheal tube inserting device has actuators protruding from a short edge towards the center of curvature of the stylet part the third actuator is reachable by the thumb from a side of the housing and usable by right-handed or left-handed operators depending on from which side the third actuator protrude.

Within the scope of the present invention a string member can e.g. be any kind of elongate thin pulling means that can fit inside the elongate guide member and having a sufficient strength to pull the tip-shaping member without accidentally rupturing when tensioned. Suitable string members include but are not limited to a metal wire, a nylon wire, e.g. a fish line, or similar means that can tension the tip-shaping member in response to application of a force onto a string-operating member.

Examples of tip-shaping members adapted to be operatively accommodated inside the tubular cover include but are not limited to one or more flat springs, e.g. a thin strip of spring steel, or a tension spring, e.g. a coiled spring, or combinations of those.

The tip-shaping member preferably has springiness that provides for the backstroke on the string-operating members.

Above the first embodiment of the endotracheal tube inserting device of the present invention includes a suspension body to amongst other suspend the string-operating members, and control the orientation and pivoting of said string-operating members. For example the suspension body is designed and arranged to restrict and stop downwards movement of an actuator. The suspension body further facilitates the correct functional and mechanical assembling of the relevant components of the mechanism to bend the bendable tip part, and the relevant components of the mechanism to eject the endotracheal tube off the stylet part.

In an alternative first embodiment the endotracheal tube inserting device may however be designed without suspension body and the string-operating members be pivotable suspended directly to e.g. a pin crosswise the shell part of the housing. Stops for preventing the actuators from been depressed too far into the housing can simply protrude from a shell part inside the space delimited by said shell parts.

The second embodiment of an endotracheal tube inserting device is yet an alternative embodiment that can have flaps or rockers as actuators.

The present invention has a minimum of structural components, which makes productions costs low and the risk that a structural components fails is at an absolute minimum.

Moreover since the structural components to be accommodated inside the housing are small and few, and can be combined at minimum space, the handle part of the endotracheal tube inserting device of the present invention has a very ergonomic design.

The elongate guide member can advantageously be made of metal, such as malleable aluminium, which allows the stylet part to be easily adapted to any desired anatomy and use, but plastic is an alternative.

Accordingly, the advantages of the endotracheal tube inserting device and endotracheal procedure and methods described herein further include, without limitation, the ability to control the shape of the distal tip part of an endotracheal tube, the ability to respond to unique anatomical differences in tracheal location and shape. The entire endotracheal tube inserting device may be disposable in its entirety, or the stylet part may be a separate disposable unit for one time use and the handle part be for reuse. So the stylet part can be a disposable stylet part while continuing use of the handle part is within the scope of the present invention.

So the endotracheal tube inserting device can be a kit of parts, which parts e.g. may include a reusable handle part and a selection of stylet parts and endotracheal tubes to go with the stylet part. Alternative compositions of the kits of parts are within the scope of the present invention.

Emphasis is made that the first embodiment of an endotracheal tube inserting device 1 and the second embodiment of an endotracheal tube inserting device 1' can implement and combine any of the bendable tip parts 6,6' e.g. shown and described in relation to FIGS. 21-24, as well as the various options for actuation means, tip part operating means, handle parts, housings and tube ejecting mechanisms described above can be used and mixed and combined to the extent desired and possible thereby arriving to even further embodiments within the scope of the appended claims.

Above the housing of the handle part is composed of assembled shell part. Within the scope of the present invention the housing can be molded as an integral unit and the first internal track and second internal track be made in same molding procedure.

Combinations of the features of the different embodiments, including modifications of and deviations from the curvatures mentioned above are within the scope of the present invention. The different embodiment of tube ejecting mechanisms can be used with any of the actuation means and with any of the tip part operating means.

The invention claimed is:

1. An endotracheal tube inserting device comprising:
   a stylet part, which has a proximal stylet end part with a proximal stylet end and an opposite distal stylet end part with a distal stylet end;
   a handle part, wherein the proximal stylet end part is stationary in relation to the handle part; and
   an endotracheal tube on the stylet part,
   wherein the endotracheal tube inserting device has a tube ejecting mechanism adapted for displacing the endotracheal tube along the stylet part in a direction of moving a distal end of the endotracheal tube towards the distal stylet end of the stylet part,
   wherein the tube ejecting mechanism comprises a ratchet mechanism, which ratchet mechanism comprises a rack part extending along at least a length of the handle part and being arranged opposite a wedge part associated with the stylet part in order to engage the rack part,
   wherein the tube ejecting mechanism comprises a reciprocating third actuator for operating the ratchet mechanism, and
   wherein the rack part has a first stationary rack part, a second stationary rack part, and a moveable third rack part or a feeder component arranged lengthwise between the first stationary rack part and the second stationary rack part.

2. The endotracheal tube inserting device according to claim 1, wherein the wedge part has a tube connector associated with the stylet part.

3. The endotracheal tube inserting device according to claim 2, wherein the tube connector is configured to mate an airway connector of the endotracheal tube.

4. The endotracheal tube inserting device according to claim 2, wherein the wedge part is provided with opposite lateral wedge parts and a center wedge part located between said lateral wedge parts.

5. The endotracheal tube inserting device according to claim 4, wherein the lateral wedge parts and the center wedge part are provided at the wedge part at a proximal end of the wedge part, optionally the tube connector is provided at an opposite distal end of the wedge part.

6. The endotracheal tube inserting device according to claim 4, wherein the lateral wedge parts and the center wedge part are provided at the wedge part between a proximal end of the wedge part and a distal end of the wedge part, optionally the tube connector is provided at the proximal end of the wedge part.

7. The endotracheal tube inserting device according to claim 2, wherein the first stationary rack part has first teeth, and the second stationary rack part has second teeth, optionally the moveable third rack part has a third teeth.

8. The endotracheal tube inserting device according to claim 7, wherein the opposite lateral wedge parts can engage the first teeth and the second teeth.

9. The endotracheal tube inserting device according to claim 7, wherein any of the first teeth, second teeth, and third teeth are tapering.

10. The endotracheal tube inserting device according to claim 7, wherein the first teeth and the second teeth are formed integral with the handle part on an interior face of the handle part.

11. The endotracheal tube inserting device according to claim 1, wherein the moveable third rack part has the third actuator arranged to protrude from the handle part, optionally from a housing of the handle part.

12. The endotracheal tube inserting device according to claim 1, wherein the stationary rack parts are integrally formed with the handle part, optionally with a housing of the handle part.

13. The endotracheal tube inserting device according to claim 1, wherein the moveable third rack part or the feeder component is configured to displace the wedge part towards the distal stylet end and is resiliently suspended inside the handle part by means of a retraction means or a resilient means.

14. The endotracheal tube inserting device according to claim 1, wherein the ratchet mechanism comprises that
   a. the feeder component is configured with the third actuator,
   b. the wedge part is slidably received by the feeder component and slidable mounted on the stylet part,
   c. the wedge part has a shaft bearing that extends crosswise between a first wedge face facing the stationary rack parts and an opposite second wedge face,
   d. the shaft bearing is configured for pivotably receiving a pivoting pawl member,
   e. which pivoting pawl member has means to engage at least the feeder component to drive the wedge part towards the distal stylet end.

15. The endotracheal tube inserting device according to claim 14, wherein the pivoting pawl member is suspended on a shaft.

16. The endotracheal tube inserting device according to claim 15, wherein the pivoting pawl member includes
   a. a first lateral pawl member, which is pivotably and slidable arranged in a first internal track for slidingly receiving a first sliding flange of the wedge part, and
   b. an opposite second lateral pawl member, which is pivotably and slidably arranged in a third internal track for receiving a second sliding flange of the wedge part.

17. The endotracheal tube inserting device according to claim 16, wherein the opposite first and second lateral pawl members protrude from respective opposite free ends of a main body of the pivoting pawl member substantially perpendicular to an axis (X) of said main body.

18. The endotracheal tube inserting device according to claim 16, wherein the opposite first and second lateral pawl members are independently pivotable.

19. The endotracheal tube inserting device according to claim 16, wherein a center pawl member protrudes substantially perpendicular to an axis (X) of a main body of the pivoting pawl member between said first and second lateral pawl members angularly displaced on the main body from said first and second lateral pawl members.

20. The endotracheal tube inserting device according to claim 19, wherein the center pawl member has a first center pawl member integral with the first lateral pawl member and a second center pawl member integral with the second lateral pawl member.

21. The endotracheal tube inserting device according to claim 20, wherein the tube ejecting mechanism has means for returning an endotracheal tube that has been displaced towards the distal stylet end back in the direction towards the proximal stylet end.

22. The endotracheal tube inserting device according to claim 21, wherein the means for returning an endotracheal tube that has been displaced towards the distal stylet end back in the direction towards the proximal stylet end includes first teeth of the first stationary rack part and second teeth of the second stationary rack part that together define an elongate rack part groove for receiving and engaging fourth teeth of an elongate moveable fourth rack part that faces the first teeth and second teeth, which moveable fourth rack part optionally has a fourth actuator protruding outside a housing of the handle part for, upon actuation, returning a wedge part towards the proximal stylet end.

23. The endotracheal tube inserting device according to claim 22, wherein the center pawl member is pivotable and slidable arranged on the main body of the pivoting pawl member between opposite first and second lateral pawl members above a back side of the moveable fourth rack part located in said elongate rack part groove, which back side of the elongate moveable fourth rack part is the side opposite the fourth teeth.

24. The endotracheal tube inserting device according to claim 19, wherein the first wedge face has an indent or stop associated with the shaft bearing, which indent or stop is adapted for accommodating and restraining a spring arm protruding from the main body of the pivoting pawl member, which spring arm protrudes angularly displaced from both the first and the second lateral pawl members and from the center pawl member in an angular direction opposite to the center pawl member, optionally in substantially the same plane as the center pawl member.

25. The endotracheal tube inserting device according to claim 24, wherein the indent or stop is a recess branching from a main bearing part of the shaft bearing.

26. The endotracheal tube inserting device according to claim 16, wherein at least one of the opposite lateral pawl members is provided with a friction increasing pad to increase friction when the lateral pawl members move in the first internal track and the third internal track of the housing and/or of the feeder component, respectively.

27. The endotracheal tube inserting device according to claim 1, wherein an interior of a housing of the handle part is configured with a first internal track for slidingly receiving a first sliding flange of the wedge part, and a second internal track for slidingly receiving the feeder component, which feeder component has a third internal track for receiving a second sliding flange of the wedge part.

28. The endotracheal tube inserting device according to claim 1, wherein the handle part is adapted for operating the stylet part and the tube ejecting mechanism and further comprises one or more of:
the proximal stylet end is situated at the handle part, and the distal stylet end has an extension in form of a bendable tip part with a free distal end,
a tip part operating member includes at least a first string member and a second string member arranged along the length of at least a length of the stylet part,
the handle part has an actuator means for operating at least the tip part operating member,
the first string member has a first proximal string end connected to a first string operating member of the actuator means and an opposite first distal string end secured at a first string-securing location at the bendable tip part,
the second string member has a second proximal string end connected to a second string operating member of the actuator means and an opposite second distal string end secured at a second string-securing location at the bendable tip part, which second string-securing location is different from the first string-securing location, and
the stylet part comprises an elongate guide member that extends into the bendable tip part, which elongate guide member and bendable tip part lengthwise encases, supports or guides at least a part of the first string member and at least a part of the second string member.

29. The endotracheal tube inserting device according to claim 28, wherein the elongate guide member is a curved pipe.

30. The endotracheal tube inserting device according to claim 28, wherein the bendable tip part includes a tubular cover that accommodates a tip-shaping member to which the first distal string end and the second distal string end are individually attached at the respective first string-securing location and second string-securing location.

31. The endotracheal tube inserting device according to claim 28, wherein the first string operating member of the actuator means includes a first lever body arranged about a first pivot axis (P1), and the second string operating member of the actuator means includes a second lever body pivotably arranged about a second pivot axis (P2),
a. said first lever body has at least one first actuator lever arm extending from the first pivot axis (P1) to a first actuator, and at least one opposite first string operating lever arm at which the first proximal string end is operatively connected to change the position of the first distal string end relative to at least the distal stylet end in response to actuating the first actuator,
b. said second lever body has at least one second actuator lever arm extending from the second pivot axis to a second actuator, and at least one opposite second string operating lever arm to which the second proximal string end is operatively connected to change the position of the second distal string end relative to at least the distal stylet end in response to actuating the second actuator.

32. The endotracheal tube inserting device according to claim 31, wherein a housing of the handle part accommodates at least the first lever body and the second lever body, which housing has a first opening for making the first actuator accessible to pivot the first lever body from outside the housing, and a second opening for making the second actuator accessible to pivot the second lever body from outside the housing.

33. The endotracheal tube inserting device according to claim 31, wherein the first lever body is pivotably suspended to move a first string-securing member of the housing and the second lever body is pivotably suspended to move a second string-securing member of the housing, and wherein the first string-securing member is arranged spaced from the first pivot axis (P1), and the second string-securing member is arranged spaced from the second pivot axis (P2).

34. The endotracheal tube inserting device according to claim 1, wherein a housing of the handle part is a curved tubular body.

\* \* \* \* \*